US008221999B2

(12) United States Patent
Kaufmann et al.

(10) Patent No.: US 8,221,999 B2
(45) Date of Patent: Jul. 17, 2012

(54) PROTEIN PRODUCTION

(75) Inventors: Hitto Kaufmann, Ulm (DE); Lore Florin, Biberach (DE); Eric Becker, Hochdorf (DE); Monilola Olayioye, Ulm (DE); Angelika Hausser, Stuttgart (DE); Tim Fugmann, Zurich (CH)

(73) Assignee: Boehringer Ingelheim Pharma GmbH & Co. KG, Ingelheim (DE)

(*) Notice: Subject to any disclaimer, the term of this patent is extended or adjusted under 35 U.S.C. 154(b) by 36 days.

(21) Appl. No.: 12/040,198

(22) Filed: Feb. 29, 2008

(65) Prior Publication Data

US 2008/0300207 A1 Dec. 4, 2008

Related U.S. Application Data

(60) Provisional application No. 60/893,025, filed on Mar. 5, 2007.

(30) Foreign Application Priority Data

| | | |
|---|---|---|
| Mar. 2, 2007 | (EP) | 07103406 |
| Mar. 15, 2007 | (EP) | 07104226 |
| Sep. 13, 2007 | (EP) | 07116358 |

(51) Int. Cl.
*C12P 21/06* (2006.01)

(52) U.S. Cl. ........ 435/69.1

(58) Field of Classification Search ........ None
See application file for complete search history.

(56) References Cited

U.S. PATENT DOCUMENTS

| | | | | |
|---|---|---|---|---|
| 5,521,297 | A * | 5/1996 | Daggett et al. | 536/23.5 |
| 5,869,250 | A * | 2/1999 | Cheng et al. | 435/6.11 |
| 7,326,768 | B2 | 2/2008 | Saus et al. | |
| 2003/0190319 | A1 | 10/2003 | Adolf et al. | |
| 2004/0175758 | A1 * | 9/2004 | Saus et al. | 435/7.1 |
| 2005/0255487 | A1 | 11/2005 | Khvorova et al. | |
| 2008/0113351 | A1 | 5/2008 | Naito et al. | |
| 2009/0018099 | A1 | 1/2009 | Kaufmann et al. | |

FOREIGN PATENT DOCUMENTS

| | | | |
|---|---|---|---|
| EP | 1 652 530 | A | 5/2006 |
| WO | WO 2007/001851 | A2 | 1/2007 |
| WO | WO 2008/107388 | A1 | 9/2008 |
| WO | 2010/128032 | A1 | 11/2010 |

OTHER PUBLICATIONS

BLAST of SEQ ID No. 17 [online], 2010 [retrieved on Dec. 15, 2010]. Retrieved from the Internet< URL: http://blast.ncbi.nlm.hig.gov/Blast.cgi>, pp. 1-5.*

BLAST, alignment of SEQ ID Nos. 17 and 19, [online], 2010 [retrieved on Dec. 15, 2010]. Retrieved from the Internet< URL: http://blast.ncbi.nlm.hig.gov/Blast.cgi>, pp. 1-3.*

Raya et al., 2000, The Journal of Biological Chemistry, 275: 40392-40399.*

Visintin et al., 1999, PNAS, USA, 96: 11723-11728.*

Mohamed Al-Rubeai, et al; Apoptosis in Cell Culture; Current Opinion in Biotechnology (1998) vol. 9 pp. 152-156.

Fabien Alpy, et al; Give Lipids a START: The StAR-Related Lipid Transfer (START) Domain in Mammals; Journal of Cell Science (2005) vol. 118 pp. 2791-2801.

Stephen F. Altschul, et al; Basic Local Alignment Search Tool; Journal Molecular Biology (1990) vol. 215 pp. 403-410.

Alberto Marcelo Diaz Anel, et al; PKCeta is Required for Beta 1 Gamma2/Beta3Gamma2- and PKD-Medicated Transport to the Cell Surface and the Organization of the Golgi Apparatus; Journal Cell Biology (2005) vol. 169 No. 1 pp. 83-91.

Frederic Bard, et al; Functional Genomics Reveals Genes Involved in Protein Secretion and Golgi Organization; Nature (2006) vol. 439 No. 2 pp. 604-607.

Louise M. Barnes, et al; Molecular Analysis of Successful Cell Line Selection in Transfected GS-NSO Myeloma Cells; Biotechnology and Bioengineering (2007) vol. 96 No. 2 pp. 337-348.

Louise M. Barnes, et al; Mammalian Cell Factories for Efficient and Stable Protein Expression; Current Opinion in Biotechnology (2006) vol. 17 pp. 381-386.

Carole L. Baron, et al; Role on Dyacylglycerol in PKD Recruitment to the TGN and Protein Transport to the Plasma Membrane; Science (2002) vol. 295 pp. 325-328.

Carl P. Blobel; Adams: Key Components in EGFR Signaling and Development; Nature Ter. Molecular Cell Biology (2005) vol. 6 pp. 32-43.

Nicole Borth, et al; Effect on Increased Expression of Protein Disulfide Isomerase and Heavy Chain Binding Protein on Antibody Secretion in a Recombinant CHO Cell Line; Biotechnology Prog. (2005) vol. 21 pp. 106-111.

Joseph W. Brewer, et al; Building an Antibody Factory: A Job for the Unfolded Protein Response; Nature Immunology (2005) vol. 6 No. 1 pp. 23-29.

Selina Chen-Kiang; Cell-Cycle Control of Plasma Cell Differentiation and Tumorigenesis; Immunological Reviews (2003) vol. 194 pp. 39-47.

Gisela G. Chiang, et al; Bcl-xl Mediated Increased Production of Humanized Monoclonal Antibodies in Chinese Hamster Ovary Cells; Biotechnology and Bioengineering (2005) vol. 91 pp. 779-792.

(Continued)

*Primary Examiner* — Joanne Hama

(74) *Attorney, Agent, or Firm* — Michael P. Morris; Edouard G. Lebel; Mary-Ellen M. Devlin

(57) ABSTRACT

The invention concerns the field of protein production and cell culture technology. CERT is identified as a novel in vivo PKD substrate. Phosphorylation on serine 132 by PKD decreases the affinity of CERT towards its lipid target phosphatidylinositol 4-phosphate at Golgi membranes and reduces ceramide transfer activity, identifying PKD as a regulator of lipid homeostasis. The present invention shows that CERT in turn is critical for PKD activation and PKD dependent protein cargo transport to the plasma membrane. The interdependence of PKD and CERT is thus a key to the maintenance of Golgi membrane integrity and secretory transport.

32 Claims, 16 Drawing Sheets

OTHER PUBLICATIONS

Raymond Davis, et al; Effect of PDI Overexpression on Recombinant Protein Secretion in CHO Cells; Biotechnology Prog. (2000) vol. 16 pp. 736-743.
Mikala Egeblad, et al; New Functions for the Matrix Metalloproteinases in Cancer Progression; Nature Review Cancer (2002) vol. 2 pp. 161-174.
Takuya Fukunaga, et al; Implications of Sphingolipid Metabolism in the Stability of the Golgi Apparatus; Journal of Cell Science (2000) vol. 113 pp. 3299-3307.
Kentaro Hanada; Discovery of the Molecular Machinery CERT for Endoplasmic Reticulum-to-Golgi Trafficking of Ceramide; Molecular and Cellular Biochemistry (2006) vol. 286 pp. 23-31.
Kentaro Hanada, et al; Molecular Machinery for Non-Vesicular Trafficking of Ceramide; Nature (2003) vol. 426 pp. 803-809.
Douglas Hanahan, et al; The Hallmarks of Cancer; Cell (2000) vol. 100 pp. 57-70.
Angelika Hausser, et al; Protein Kinase D Regulates Vesicular Transport by Phosphorylating and Activating Phosphatidylinositol-4 Kinase IIIβ at the Golgi Complex; Nature Cell Biology (2005) vol. 7 No. 9 pp. 880-886.
Andrew D. Hooker, et al; Constraints on the Transport and Glycosylation of Recombinant IFN-γ in Chinese Hamster Ovary and Insect Cells; Biotechnology and Bioengineering (1999) vol. 63 pp. 559-572.
Shi-Zhen Hu, et al; Minibody: A Novel Engineered Anti-Carcinoembryonic Antigen Antibody Fragment (Single-Chain Fv-Ch3) Which exhibits Rapid, High-Level targeting of Xenografts; Cancer Research (1996) vol. 56 pp. 3055-3061.
James S. Huston, et al; Protein Engineering of Antibody Binding Sites: Recovery of Specific Activity in an Anti-Digoxin Single-Chain Fv Analogue Produced in *Escherichia coli*; Proc. Natl. Acad. Sci. USA. (1988) vol. 85 pp. 5879-5883.
Neal N. Iwakoshi, et al; The X-Box Binding Protein-1 Transcription Factor is Required for Plasma Cell Differentiation and the unfolded Protein Response; Immunological Reviews (2003) vol. 194 pp. 29-38.
Meena Jaggi, et al; E-Cadherin Phosphorylation by Protein Kinase Dl/Protein Kinase Cμ is Associated with Altered Cellular Aggregation and Motility in Prostate Cancer; Cancer Research (2005) vol. 65 No. 2 pp. 483-492.
Teresa Iglesias, et al; Identification and Cloning of Kidins220, a Novel Neuronal Substrate of Protein Kinase D; The Journal of Biological Chemistry (2000) vol. 275 No. 51 pp. 40048-40056.
Miyuki Kawano, et al; Efficient trafficking of Ceramide from the Endoplasmic Reticulum to the Golgi Apparatus Requires a Vamp-Associated Protein-Interacting FFAT Motif of Cert; Journal of Biological Chemistry (2006) vol. 281 No. 40 pp. 30279-30288.
Alexander A. Kortt, et al; Single-Chain Fv Fragments of Anti-Neuraminidase Antibody NC10 Containing Five and Ten-Residue Linkers Form Dimers and with Zero-Residue Linker a Trimer; Protein Engineering (1997) vol. 10 No. 4 pp. 423-433.
Tim Levine; et al; Inter-Organelle Membrane Contact Sited; through a Glass, Darkly; Current Opinion in Cell Biology (2006) vol. 18 pp. 371-378.
Timothy P. Levine, et al; Targeting of Golgi-Specific Pleckstrin Homology Domains Involves Both Ptdlns 4-Kinase-Dependent and -Independent Components; Current Biology (2002) vol. 12 pp. 695-704.
Monika Liljedahl, et al; Protein Kinase D Regulates the Fission of Cell Surface Destined Transport Carriers from the Trans-Golgi Network; Cell (2001) vol. 104 pp. 409-420.
Vladimir Litvak, et al; Maintenance of the Diacylglycerol Level in the Golgi Apparatus by the Nir2 Protein is Critical for Golgi Secretory Function; Nature Cell Biology (2005) vol. 7 No. 3 pp. 225-234.
Chritopher J.R. Loewen, et al; A Conserved ER Targeting Motif in three Families of Lipid Binding Proteins and in Opilp Binds VAP; The EMBO Journal (2003) vol. 22 No. 9 pp. 2025-2035.
Brett Lovejoy, et al; Crystal Structure of a Synthetic Triple-Stranded α-Helical Bundle; Science (1993) vol. 259 pp. 1288-1293.
Thomas L. Madden, et al; Applications of Network BLAST Server; Methods of Enzymology (1996) vol. 266 pp. 131-141.
Yusuke Maeda, et al; Recruitment of Protein Kinase D to the Trans-Golgi Network Via the First Cysteine-Rich Domain; The EMBO Journal (2001) vol. 20 No. 21 pp. 5982-5990.
Monilola A. Olayioye, et al; StarD10, a START Domain Protein Overexpresses in Breast Cancer, Functions as a Phospholipid Transfer Protein; The Journal of Biological Chemistry (2005) vol. 280 No. 29 pp. 27436-27442.
Christopher M. Overall, et al; Validating Matrix Metalloproteinases as Drug Targets and Anti-Targets Targets for Cancer Therapy; Nature Reviews (2006) vol. 6 pp. 227-239.
Peter Pack, et al; Tetravalent Miniantibodies with High Avidity Assembling in *Escherichia coli*; Journal Molecular Biology (1995) vol. 246 pp. 28-34.
Olga Perisic, et al; Crystal Structure of a Diabody, a Bivalent Antibody Fragment; Structure (1994) vol. 2 pp. 1217-1226.
Angel Raya, et al; Goodpasture Antigen-Binding Protein, the Kinase That Phosphorylates the Goodpasture Antigen, is an alternatively Spliced Variant Implicated in Autoimmune Pathogenesis; The Journal of Biological Chemistry (2000) vol. 275 No. 51 pp. 40392-40399.
An Rykx, et al; Protein Kinase D: A Family Affair; FEBS Letters (2003) vol. 546 pp. 81-86.
A.L. Shaffer, et al; XBP1, Downstream of Blimp-1, Expands the Secretory Apparatus and Other Organelles, and Increases Protein Synthesis in Plasma Cell Differentiation; Immunity (2004) vol. 21 pp. 81-93.
Raymond E. Soccio, et al; StAR-Related Lipid Transfer (START) Proteins: Mediators of intracellular Lipid Metabolism; The Journal of Biological Chemistry (2003) vol. 278 No. 25 pp. 22183-22186.
Pentti Somerharju; Pyrene-Labeled Lipids as Tools in Membrane Biophysics and Cell Biology; Chemistry and Physics of Lipids (2002) vol. 116 pp. 57-74.
Balazs Toth, et al; Phosphatidylinositol 4-Kinase IIIβ Regulates the Transport of Ceramide Between the Endoplasmic Reticulum and Golgi; The Journal of Biological Chemistry (2006) vol. 281 No. 47 pp. 36369-36377.
Gail Urlaub, et al; Deletion of the Diploid Dihydrofolate Reductase Locus from Cultured Mammalian Cells; Cell (1983) vol. 33 pp. 405-412.
Rick B. Vega, et al; Protein Kinases C and D Mediate Agonist-Dependent Cardiac Hypertrophy through Nuclear Export of Histone Deacetylase 5; Mollecular and Cellular Biology (2004) vol. 24 No. 19 pp. 8374-8385.
Qiming J. Wang, et al; PKD at the Crossroads of DAG and PKC Signaling; Trends and Pharmacological Sciences (2006) vol. 27 No. 6 pp. 317-323.
Ying Wang, et al; The RAS Effector RIN1 Directly Competes with RAF and is regulated by 14-3-3 Proteins; Mollecular and Cellular Biology (2002) vol. 22 No. 3 pp. 916-926.
Roberto Weigert, et al; CtBP/BARS Induces Fission of Golgi Membranes by Acylating Lysophosphatidic Acid; Nature (1999) vol. 402 pp. 429-433.
Rolf G. Werner, et al; Economic Aspects of Commercial Manufacture of Biopharmaceuticals; Journal of Biotechnology (2004) vol. 113 pp. 171-182.
Karel W.A. Wirtz, et al; Phospholipid Transfer Proteins in Perspective; FEBS Letters (2006) vol. 580 pp. 5436-5441.
Florian M. Wurm; Production of Recombinant Protein Therapeutics in Cultivated Mammalian Cells; Nature Biotechnology (2004) vol. 22 No. 11 pp. 1393-1398.
Charles Yeaman, et al; Protein Kinase D Regulates Basolateral Membrane Protein Exit from Trans-Golgi Network; Nature Cell Biology (2004) vol. 6 No. 2 pp. 106-112.
Heike Dopplers, et al; A Phosphorylation State-Specific Antibody Recognizes Hsp27, a Novel Substrate of Protein Kinase D; The Journal of Biological Chemistry (2005) vol. 280 No. 15 pp. 15013-15019.
Marcel Tigges, et al; Xbpl-Based Engineering of Secretory Capacity Enhances the Productivity of Chinese Hamster Ovary Cells; Metabolic Engineering (2006) vol. 8 pp. 264-272.
Yosuke Tsujishita, et al; Structure and Lipid Transport Mechanism of a StAR-Related Domain; Nature Structural Biology (2000) vol. 7 No. 5 pp. 408-414.

Jinghui Zhang, et al; PowerBLAST: A Network BLAST Application for Interactive or Automated Sequence Analysis and Annotation; Genome Research (1997) vol. 7 pp. 649-656.

Gargi Seth, et al; Engineering Cells for Cell Culture Bioprocessing-Physiological Fundamentals; Adv Biochem Engin/BioTechnology (2006) vol. 101 pp. 119-164.

Andrew J. Dorner, et al; The Levels of Endoplasmic Reticulum Proteins and ATP Affect Folding and Secretion of Selective Proteins; Biologicals (1994) vol. 22 pp. 103-112.

S.C.O. Pak, et al; Super-CHO—A Cell Line Capable of Autocrine Growth under Fully Defined Protein-Free Conditions; Cytotechnology (1996) vol. 22 pp. 139-146.

Robert K. Scopes; Classical and Modern Techniques in Protein Purification; Protein Purification: Micro to Macro (1987) pp. 1-15 Alan R. Liss, Inc.

Ryan J. Perry, et al; Molecular Mechanisms and Regulation of Ceramide Transport; Biochimica et Biophysica Acta (2005) vol. 1734 pp. 220-234.

Peter Pack, et al; Improved Bivalent Miniantibodies, with Identical Avidity as Whole Antibodies, Produced by High Cell Density Fermentation of *Escherichia coli*; Bio/Technology (1993) vol. 11 pp. 1271-1277.

Hitto Kaufmann, et al; Metabolic Engineering of Mammalian Cells for Higher Protein Yield; Gene Transfer and Expression in Mammalian Cells (2003) chapter 15 pp. 457-469, Elsevier Science B.V.

Marin Schroder; The Unfolded Protein Response; Molecular Biotechnology (2006) vol. 34 pp. 279-290.

Hausser, Angelika et al; Protein Kinase D Regulates Vesicular Transport by Phosphorylating and Activating Phosphatidylinositol-4 Kinase IIIβ at the Golgi Complex; Nature Cell Biology (2005) vol. 7 No. 9 pp. 880-886.

International Search Report PCT/EP2008/052493 mailed Aug. 20, 2008.

U.S. Appl. No. 12/528,828, filed Aug. 27, 2009. Inventor Hitto Kauffmann.

Hausser, Angelika, et al. Structural requirements for ocalization and activation of protein kinance C μ (PKC μ) at the Golgi compartment. The Rockerfeller University Press, The Journal of Cell Biology, V 156 No. 1, Jan. 7, 2002, pp. 65-74.

www.ncbi.nlm.nih.gov/nuccore/5031716 NCBI Reference Sequence: NM 0057131.1. Jun. 1, 2008 and Sequence Alignment Data.

Florin, Lore, et al., Heterologous expression of the lipid transfer protein CERT increases therapeutic protein productivity of mammalian cells; Journal of Biotechnology (2009), vol. 141, No. 1-2, pp. 84-90.

Fugmann, Tim, et al., Regulation of secretory transport by protein kinase D-mediated phosphorylation of the ceramide transfer protein; Journal of Cell Biology (2007), vol. 178, No. 1, pp. 15-22.

Hanada, Kentaro, et al., CERT and intracellular trafficking of ceramide; Biochimica et Biophysica Acta (2007), 1771, pp. 644-653.

Parkin, Edward, et al., Dual Mechanisms for Shedding of the Cellular Prion Protein; The Journal of Biological Chemistry (2004), vol. 279, No. 1, pp. 1170-1178.

U.S. Appl. No. 13/318,509, filed Jan. 13, 2012, with first-named inventor Lore Florin.

* cited by examiner

The START domain protein family

FIGURE 3
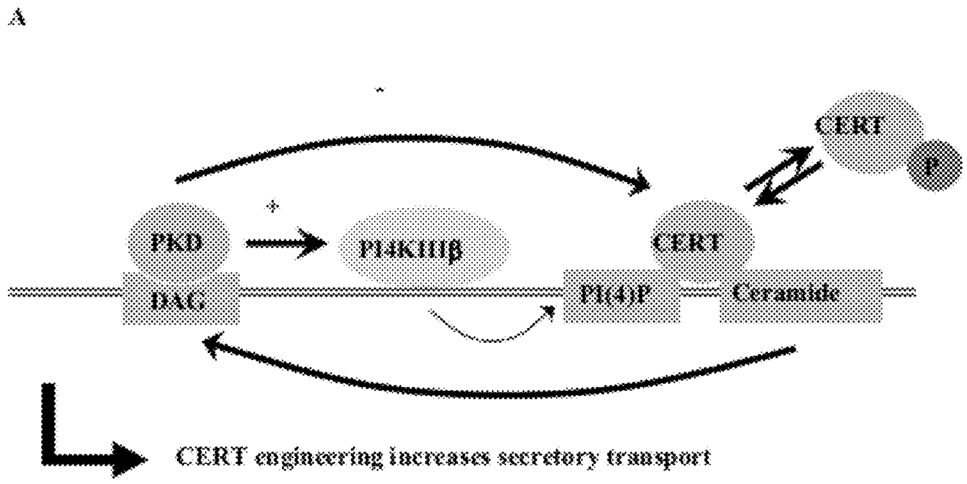
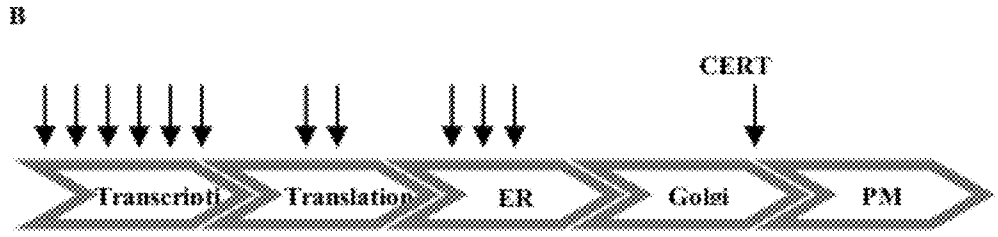

B

A

B

FIGURE 8
A
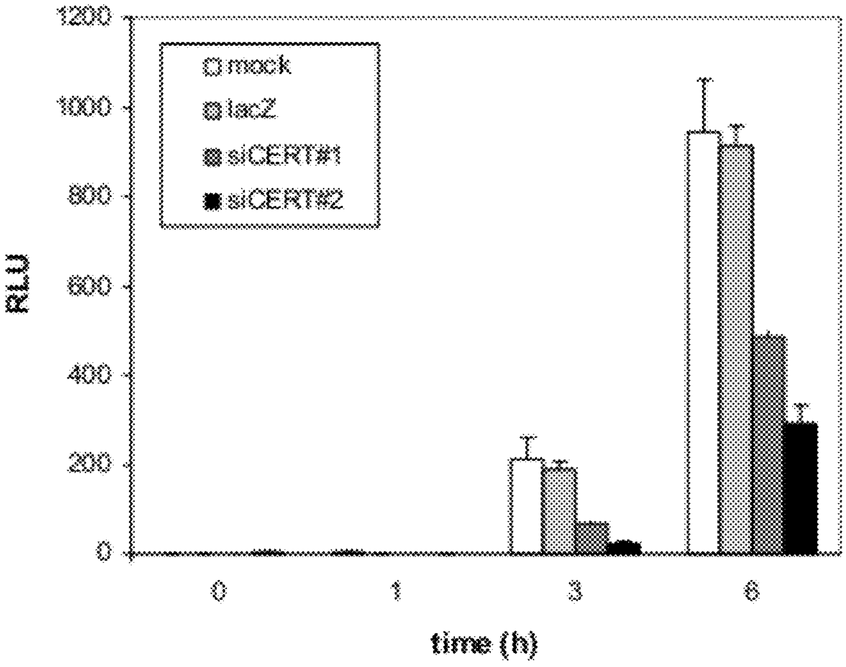
B
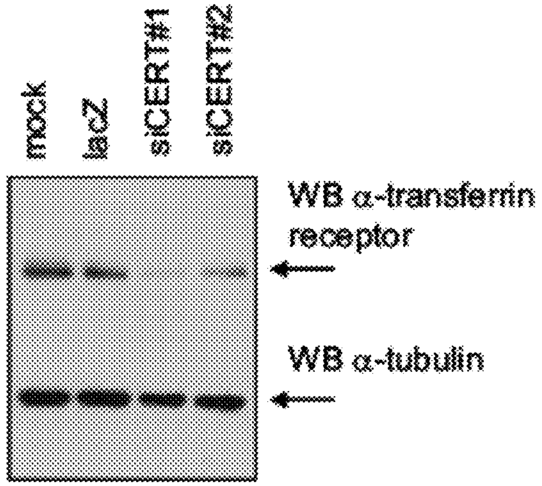

[illegible]

[illegible]

[illegible]

[illegible]

B

```
rhogap_rat/1-20   HFLQDCVDGLFKEVKEKFKGWVSYP-----TSEQAELSYKKVS-------------EGPP
CONSENSUS/80%     .h..t...t.ht.hh.t...W...................hhth..................
CONSENSUS/65%     .httpsttthhphhtsstttWhh..........ptttshpth..............tsps
CONSENSUS/50%     phpscsspshlppsssspcsWspss......ptcstpcshpphsss..........sucs

rhogap_rat/1-20   LRLWRATIEVPA--APKEIIKRLLKEQHLWDVDLL------------DSKVIEILDSQ---
CONSENSUS/80%     .+h.thh.......h...hh.t......tWpp.h.............hthlp.ht.s...
CONSENSUS/65%     h+hhahl.tss...hhtplhpsh....pWcpsht...........tspslctlsss...
CONSENSUS/50%     hRatulVsssss.plsp-lhccsth.hhcWDcshs...........pspll-slsss...

rhogap_rat/1-20   ----TEIYQYVQNSMA--PHPA-RDYVVLRTWRTN-------LPRGACALLFTSVDHDRA
CONSENSUS/80%     ....a.l.h...t..h...h.s.R-hh.lR.hp.....  .....tt.hhlh..ohp..t.
CONSENSUS/65%     ....sslhhhhsphhh..slss.R-hlhlRhh+p....  ....spsshslsstSlsp.pt
CONSENSUS/50%     ....uslpahssssss.sPlsP.RDsVhVRpp+p....  ....sccsallllssSlspsss

rhogap_rat/1-20   P------VAGVRVNVLLSRYLIEPCGSGK------------SKLTYMCRADLRGHMP----
CONSENSUS/80%     ........thhRsphh.shhhhp..tts............sphhhl..h-hts.......
CONSENSUS/65%     s.......shlRschhsothhlpspsss............splsal.ps-lputh.....
CONSENSUS/50%     ss....psuhlRucphPSGhlIcssusGh...........o+lsalppsDLcGpsP....

rhogap_rat/1-20   EWYTKSFGHLCAAEVVKIRDSFSNQSTESED
CONSENSUS/80%     p.hhp.hht.th..hhp....htthpt.t.p
CONSENSUS/65%     phhhcshhppshh.hhct..hhstlpptstp
CONSENSUS/50%     ctll+slhssuhspss+p..phAsLpcssp+
```

Figure 10
A Specific mAB productivity in serial cultures
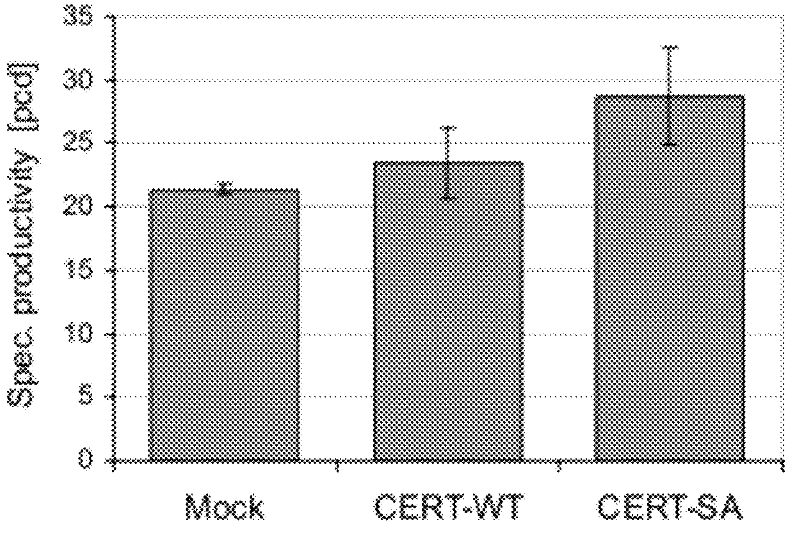
B Specific productivity in fed-batch processes
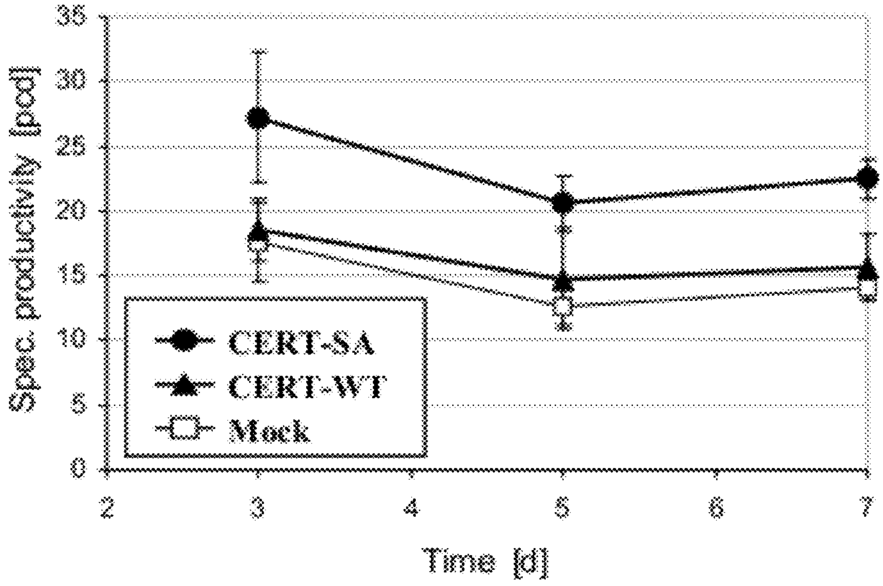

FIGURE 11
A HSA titer and specific productivity
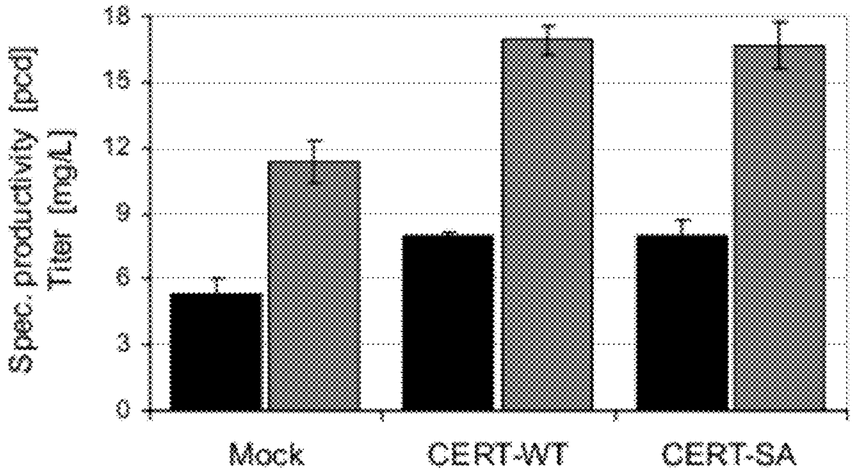
B Specific productivity in fed-batch processes
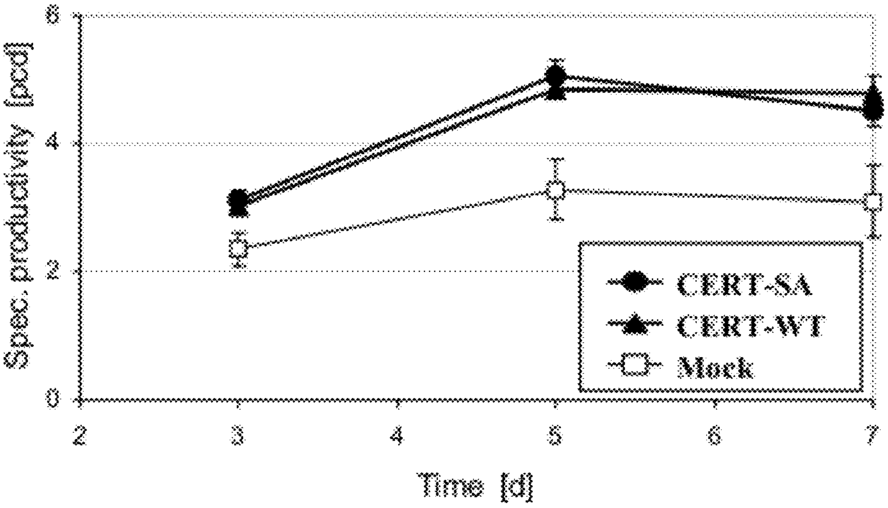

C Titer in fed-batch processes

SEQUENCE LISTING

```
<160> NUMBER OF SEQ ID NOS: 30

<210> SEQ ID NO 1
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1

cgtcgacatg gcgcaatggt gtccctgg                                        28


<210> SEQ ID NO 2
<211> LENGTH: 28
```

<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccagggacac cattgcgcca tgtcgacg 28

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggttaaacgt gaggacgcct ggcagaagag actgg 35

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccagtctctt ctgccaggcg tcctcacgtt taacc 35

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ggtgtccctg gtgtcttgag caagtggcta ctc 33

<210> SEQ ID NO 6
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gagtagccac ttgctcaaga caccagggac acc 33

<210> SEQ ID NO 7
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
ccacaugacu uacucauuat t 21

<210> SEQ ID NO 8

<211> LENGTH: 21
<212> TYPE: DNA
<213> ORGANISM: Artificial Sequence
<220> FEATURE:
<223> OTHER INFORMATION: Description of Combined DNA/RNA Molecule:
Synthetic oligonucleotide
<220> FEATURE:
<223> OTHER INFORMATION: Description of Artificial Sequence: Synthetic
oligonucleotide

<400> SEQUENCE: 8
gaacagagga agcauauaat t 21

<210> SEQ ID NO 9
<211> LENGTH: 21
<212> TYPE: DNA
<213> ORGANISM: Artificial Sequence
<220> FEATURE:
<223> OTHER INFORMATION: Description of Combined DNA/RNA Molecule:
Synthetic oligonucleotide
<220> FEATURE:
<223> OTHER INFORMATION: Description of Artificial Sequence: Synthetic
oligonucleotide

<400> SEQUENCE: 9
gcggcugccg gaauuuacct t 21

<210> SEQ ID NO 10
<211> LENGTH: 1797
<212> TYPE: DNA
<213> ORGANISM: Homo sapiens
<220> FEATURE:
<223> OTHER INFORMATION: CERT cDNA

<400> SEQUENCE: 10
atgtcggata atcagagctg gaactcgtcg ggctcggagg aggatccaga gacggagtct 60
gggccgcctg tggagcgctg cggggtcctc agtaagtgga caaactacat tcatgggtgg 120
caggatcgtt gggtagtttt gaaaaataat gctctgagtt actacaaatc tgaagatgaa 180
acagagtatg gctgcagagg atccatctgt cttagcaagg ctgtcatcac acctcacgat 240
tttgatgaat gtcgatttga tattagtgta aatgatagtg tttggtatct tcgtgctcag 300
gatccagatc atagacagca atggatagat gccattgaac agcacaagac tgaatctgga 360
tatggatctg aatccagctt gcgtcgacat ggctcaatgg tgtccctggt gtctggagca 420
agtggctact ctgcaacatc cacctcttca ttcaagaaag gccacagttt acgtgagaag 480
ttggctgaaa tggaaacatt tagagacatc ttatgtagac aagttgacac gctacagaag 540
tactttgatg cctgtgctga tgctgtctct aaggatgaac ttcaaaggga taaagtggta 600
gaagatgatg aagatgactt tcctacaacg cgttctgatg gtgacttctt gcatagtacc 660
aacggcaata aagaaaagtt atttccacat gtgacaccaa aaggaattaa tggtatagac 720
tttaaagggg aagcgataac ttttaaagca actactgctg gaatccttgc aacactttct 780
cattgtattg aactaatggt taaacgtgag gacagctggc agaagagact ggataaggaa 840
actgagaaga aaagaagaac agaggaagca tataaaaatg caatgacaga acttaagaaa 900
aaatcccact ttggaggacc agattatgaa gaaggcccta acagtctgat taatgaagaa 960
gagttctttg atgctgttga agctgctctt gacagacaag ataaaataga agaacagtca 1020
cagagtgaaa aggtgagatt acattggcct acatccttgc cctctggaga tgccttttct 1080
tctgtgggga cacatagatt tgtccaaaag gttgaagaga tggtgcagaa ccacatgact 1140
tactcattac aggatgtagg cggagatgcc aattggcagt tggttgtaga agaaggagaa 1200

-continued atgaaggtat acagaagaga agtagaagaa aatgggattg ttctggatcc tttaaaagct 1260
acccatgcag ttaaaggcgt cacaggacat gaagtctgca attatttctg gaatgttgac 1320
gttcgcaatg actgggaaac aactatagaa aactttcatg tggtggaaac attagctgat 1380
aatgcaatca tcatttatca aacacacaag agggtgtggc ctgcttctca gcgagacgta 1440
ttatatcttt ctgtcattcg aaagatacca gccttgactg aaaatgaccc tgaaacttgg 1500
atagtttgta atttttctgt ggatcatgac agtgctcctc taaacaaccg atgtgtccgt 1560
gccaaaataa atgttgctat gatttgtcaa accttggtaa gcccaccaga gggaaaccag 1620
gaaattagca gggacaacat tctatgcaag attacatatg tagctaatgt gaaccctgga 1680
ggatgggcac cagcctcagt gttaagggca gtggcaaagc gagagtatcc taaatttcta 1740
aaacgtttta cttcttacgt ccaagaaaaa actgcaggaa agcctatttt gttctag 1797

<210> SEQ ID NO 11
<211> LENGTH: 598
<212> TYPE: PRT
<213> ORGANISM: Homo sapiens
<220> FEATURE:
<223> OTHER INFORMATION: CERT protein

<400> SEQUENCE: 11

Met Ser Asp Asn Gln Ser Trp Asn Ser Ser Gly Ser Glu Glu Asp Pro
1               5                   10                  15

Glu Thr Glu Ser Gly Pro Pro Val Glu Arg Cys Gly Val Leu Ser Lys
            20                  25                  30

Trp Thr Asn Tyr Ile His Gly Trp Gln Asp Arg Trp Val Val Leu Lys
        35                  40                  45

Asn Asn Ala Leu Ser Tyr Tyr Lys Ser Glu Asp Glu Thr Glu Tyr Gly
    50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
        115                 120                 125

Arg His Gly Ser Met Val Ser Leu Val Ser Gly Ala Ser Gly Tyr Ser
    130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
            180                 185                 190

Glu Leu Gln Arg Asp Lys Val Val Glu Asp Asp Glu Asp Asp Phe Pro
        195                 200                 205

Thr Thr Arg Ser Asp Gly Asp Phe Leu His Ser Thr Asn Gly Asn Lys
    210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

```
Trp Gln Lys Arg Leu Asp Lys Glu Thr Glu Lys Lys Arg Arg Thr Glu
        275                 280                 285

Glu Ala Tyr Lys Asn Ala Met Thr Glu Leu Lys Lys Lys Ser His Phe
    290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
            340                 345                 350

Leu Pro Ser Gly Asp Ala Phe Ser Ser Val Gly Thr His Arg Phe Val
        355                 360                 365

Gln Lys Val Glu Glu Met Val Gln Asn His Met Thr Tyr Ser Leu Gln
    370                 375                 380

Asp Val Gly Gly Asp Ala Asn Trp Gln Leu Val Val Glu Glu Gly Glu
385                 390                 395                 400

Met Lys Val Tyr Arg Arg Glu Val Glu Glu Asn Gly Ile Val Leu Asp
                405                 410                 415

Pro Leu Lys Ala Thr His Ala Val Lys Gly Val Thr Gly His Glu Val
            420                 425                 430

Cys Asn Tyr Phe Trp Asn Val Asp Val Arg Asn Asp Trp Glu Thr Thr
        435                 440                 445

Ile Glu Asn Phe His Val Val Glu Thr Leu Ala Asp Asn Ala Ile Ile
    450                 455                 460

Ile Tyr Gln Thr His Lys Arg Val Trp Pro Ala Ser Gln Arg Asp Val
465                 470                 475                 480

Leu Tyr Leu Ser Val Ile Arg Lys Ile Pro Ala Leu Thr Glu Asn Asp
                485                 490                 495

Pro Glu Thr Trp Ile Val Cys Asn Phe Ser Val Asp His Asp Ser Ala
            500                 505                 510

Pro Leu Asn Asn Arg Cys Val Arg Ala Lys Ile Asn Val Ala Met Ile
        515                 520                 525

Cys Gln Thr Leu Val Ser Pro Pro Glu Gly Asn Gln Glu Ile Ser Arg
    530                 535                 540

Asp Asn Ile Leu Cys Lys Ile Thr Tyr Val Ala Asn Val Asn Pro Gly
545                 550                 555                 560

Gly Trp Ala Pro Ala Ser Val Leu Arg Ala Val Ala Lys Arg Glu Tyr
                565                 570                 575

Pro Lys Phe Leu Lys Arg Phe Thr Ser Tyr Val Gln Glu Lys Thr Ala
            580                 585                 590

Gly Lys Pro Ile Leu Phe
        595
```

<210> SEQ ID NO 12
<211> LENGTH: 2389
<212> TYPE: DNA
<213> ORGANISM: Homo sapiens
<220> FEATURE:
<223> OTHER INFORMATION: CERT L cDNA

<400> SEQUENCE: 12

```
gcaggaagat ggcggcggta gcggaggtgt gagtggacgc gggactcagc ggccggattt      60

tctcttccct tcttttccct tttccttccc tatttgaaat tggcatcgag ggggctaagt     120

tcgggtggca gcgccgggcg caacgcaggg gtcacggcga cggcggcggc ggctgacggc     180
```

-continued

```
tggaagggta ggcttcattc accgctcgtc ctccttcctc gctccgctcg gtgtcaggcg    240

cggcggcggc gcggcgggcg gacttcgtcc ctcctcctgc tcccccccac accggagcgg    300

gcactcttcg cttcgccatc ccccgaccct tcaccccgag gactgggcgc ctcctccggc    360

gcagctgagg gagcgggggc cggtctcctg ctcggttgtc gagcctccat gtcggataat    420

cagagctgga actcgtcggg ctcggaggag gatccagaga cggagtctgg gccgcctgtg    480

gagcgctgcg ggtcctcag taagtggaca aactacattc atgggtggca ggatcgttgg    540

gtagttttga aaaataatgc tctgagttac tacaaatctg aagatgaaac agagtatggc    600

tgcagaggat ccatctgtct tagcaaggct gtcatcacac ctcacgattt tgatgaatgt    660

cgatttgata ttagtgtaaa tgatagtgtt tggtatcttc gtgctcagga tccagatcat    720

agacagcaat ggatagatgc cattgaacag cacaagactg aatctggata tggatctgaa    780

tccagcttgc gtcgacatgg ctcaatggtg tccctggtgt ctggagcaag tggctactct    840

gcaacatcca cctcttcatt caagaaaggc cacagtttac gtgagaagtt ggctgaaatg    900

gaaacattta gagacatctt atgtagacaa gttgacacgc tacagaagta ctttgatgcc    960

tgtgctgatg ctgtctctaa ggatgaactt caaagggata aagtggtaga agatgatgaa   1020

gatgactttc ctacaacgcg ttctgatggt gacttcttgc atagtaccaa cggcaataaa   1080

gaaaagttat ttccacatgt gacaccaaaa ggaattaatg gtatagactt taaaggggaa   1140

gcgataactt ttaaagcaac tactgctgga atccttgcaa cactttctca ttgtattgaa   1200

ctaatggtta aacgtgagga cagctggcag aagagactgg ataaggaaac tgagaagaaa   1260

agaagaacag aggaagcata taaaaatgca atgacagaac ttaagaaaaa atcccacttt   1320

ggaggaccag attatgaaga aggccctaac agtctgatta atgaagaaga gttctttgat   1380

gctgttgaag ctgctcttga cagacaagat aaaatagaag aacagtcaca gagtgaaaag   1440

gtgagattac attggcctac atccttgccc tctggagatg ccttttcttc tgtggggaca   1500

catagatttg tccaaaagcc ctatagtcgc tcttcctcca tgtcttccat tgatctagtc   1560

agtgcctctg atgatgttca cagattcagc tcccaggttg aagagatggt gcagaaccac   1620

atgacttact cattacagga tgtaggcgga gatgccaatt ggcagttggt tgtagaagaa   1680

ggagaaatga aggtatacag aagagaagta gaagaaaatg ggattgttct ggatccttta   1740

aaagctaccc atgcagttaa aggcgtcaca ggacatgaag tctgcaatta tttctggaat   1800

gttgacgttc gcaatgactg ggaaacaact atagaaaact ttcatgtggt ggaaacatta   1860

gctgataatg caatcatcat ttatcaaaca cacaagaggg tgtggcctgc ttctcagcga   1920

gacgtattat atctttctgt cattcgaaag ataccagcct tgactgaaaa tgaccctgaa   1980

acttggatag tttgtaattt ttctgtggat catgacagtg ctcctctaaa caaccgatgt   2040

gtccgtgcca aaataaatgt tgctatgatt tgtcaaacct tggtaagccc accagaggga   2100

aaccaggaaa ttagcaggga caacattcta tgcaagatta catatgtagc taatgtgaac   2160

cctggaggat gggcaccagc ctcagtgtta agggcagtgg caaagcgaga gtatcctaaa   2220

tttctaaaac gttttacttc ttacgtccaa gaaaaaactg caggaaagcc tattttgttc   2280

tagtattaac aggtactaga agatatgttt tatctttttt taactttatt tgactaatat   2340

gactgtcaat actaaaattt agttgttgaa agtatttact atgtttttt              2389
```

<210> SEQ ID NO 13
<211> LENGTH: 624
<212> TYPE: PRT
<213> ORGANISM: Homo sapiens
<220> FEATURE:

<223> OTHER INFORMATION: CERT L protein

<400> SEQUENCE: 13

```
Met Ser Asp Asn Gln Ser Trp Asn Ser Ser Gly Ser Glu Glu Asp Pro
1               5                   10                  15

Glu Thr Glu Ser Gly Pro Pro Val Glu Arg Cys Gly Val Leu Ser Lys
            20                  25                  30

Trp Thr Asn Tyr Ile His Gly Trp Gln Asp Arg Trp Val Val Leu Lys
        35                  40                  45

Asn Asn Ala Leu Ser Tyr Tyr Lys Ser Glu Asp Glu Thr Glu Tyr Gly
    50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
        115                 120                 125

Arg His Gly Ser Met Val Ser Leu Val Ser Gly Ala Ser Gly Tyr Ser
    130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
            180                 185                 190

Glu Leu Gln Arg Asp Lys Val Val Glu Asp Asp Glu Asp Asp Phe Pro
        195                 200                 205

Thr Thr Arg Ser Asp Gly Asp Phe Leu His Ser Thr Asn Gly Asn Lys
    210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

Trp Gln Lys Arg Leu Asp Lys Glu Thr Glu Lys Lys Arg Arg Thr Glu
        275                 280                 285

Glu Ala Tyr Lys Asn Ala Met Thr Glu Leu Lys Lys Lys Ser His Phe
    290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
            340                 345                 350

Leu Pro Ser Gly Asp Ala Phe Ser Ser Val Gly Thr His Arg Phe Val
        355                 360                 365

Gln Lys Pro Tyr Ser Arg Ser Ser Ser Met Ser Ser Ile Asp Leu Val
    370                 375                 380

Ser Ala Ser Asp Asp Val His Arg Phe Ser Ser Gln Val Glu Glu Met
385                 390                 395                 400

Val Gln Asn His Met Thr Tyr Ser Leu Gln Asp Val Gly Gly Asp Ala
```

```
                405                 410                 415

Asn Trp Gln Leu Val Val Glu Glu Gly Glu Met Lys Val Tyr Arg Arg
            420                 425                 430

Glu Val Glu Glu Asn Gly Ile Val Leu Asp Pro Leu Lys Ala Thr His
        435                 440                 445

Ala Val Lys Gly Val Thr Gly His Glu Val Cys Asn Tyr Phe Trp Asn
    450                 455                 460

Val Asp Val Arg Asn Asp Trp Glu Thr Thr Ile Glu Asn Phe His Val
465                 470                 475                 480

Val Glu Thr Leu Ala Asp Asn Ala Ile Ile Ile Tyr Gln Thr His Lys
                485                 490                 495

Arg Val Trp Pro Ala Ser Gln Arg Asp Val Leu Tyr Leu Ser Val Ile
            500                 505                 510

Arg Lys Ile Pro Ala Leu Thr Glu Asn Asp Pro Glu Thr Trp Ile Val
        515                 520                 525

Cys Asn Phe Ser Val Asp His Asp Ser Ala Pro Leu Asn Asn Arg Cys
    530                 535                 540

Val Arg Ala Lys Ile Asn Val Ala Met Ile Cys Gln Thr Leu Val Ser
545                 550                 555                 560

Pro Pro Glu Gly Asn Gln Glu Ile Ser Arg Asp Asn Ile Leu Cys Lys
                565                 570                 575

Ile Thr Tyr Val Ala Asn Val Asn Pro Gly Gly Trp Ala Pro Ala Ser
            580                 585                 590

Val Leu Arg Ala Val Ala Lys Arg Glu Tyr Pro Lys Phe Leu Lys Arg
        595                 600                 605

Phe Thr Ser Tyr Val Gln Glu Lys Thr Ala Gly Lys Pro Ile Leu Phe
    610                 615                 620


<210> SEQ ID NO 14
<211> LENGTH: 1797
<212> TYPE: DNA
<213> ORGANISM: Homo sapiens
<220> FEATURE:
<223> OTHER INFORMATION: CERT S132A cDNA

<400> SEQUENCE: 14

atgtcggata atcagagctg gaactcgtcg ggctcggagg aggatccaga gacggagtct      60

gggccgcctg tggagcgctg cggggtcctc agtaagtgga caaactacat tcatgggtgg     120

caggatcgtt gggtagtttt gaaaaataat gctctgagtt actacaaatc tgaagatgaa     180

acagagtatg gctgcagagg atccatctgt cttagcaagg ctgtcatcac acctcacgat     240

tttgatgaat gtcgatttga tattagtgta aatgatagtg tttggtatct tcgtgctcag     300

gatccagatc atagacagca atggatagat gccattgaac agcacaagac tgaatctgga     360

tatggatctg aatccagctt gcgtcgacat ggcgcaatgg tgtccctggt gtctggagca     420

agtggctact ctgcaacatc cacctcttca ttcaagaaag gccacagttt acgtgagaag     480

ttggctgaaa tggaaacatt tagagacatc ttatgtagac aagttgacac gctacagaag     540

tactttgatg cctgtgctga tgctgtctct aaggatgaac ttcaaaggga taaagtggta     600

gaagatgatg aagatgactt tcctacaacg cgttctgatg gtgacttctt gcatagtacc     660

aacggcaata aagaaaagtt atttccacat gtgacaccaa aaggaattaa tggtatagac     720

tttaaagggg aagcgataac ttttaaagca actactgctg gaatccttgc aacactttct     780

cattgtattg aactaatggt taaacgtgag gacagctggc agaagagact ggataaggaa     840

actgagaaga aaagaagaac agaggaagca tataaaaatg caatgacaga acttaagaaa     900
```

-continued

```
aaatcccact ttggaggacc agattatgaa gaaggcccta acagtctgat taatgaagaa    960

gagttctttg atgctgttga agctgctctt gacagacaag ataaaataga agaacagtca   1020

cagagtgaaa aggtgagatt acattggcct acatccttgc cctctggaga tgccttttct   1080

tctgtgggga cacatagatt tgtccaaaag gttgaagaga tggtgcagaa ccacatgact   1140

tactcattac aggatgtagg cggagatgcc aattggcagt tggttgtaga agaaggagaa   1200

atgaaggtat acagaagaga agtagaagaa aatgggattg ttctggatcc tttaaaagct   1260

acccatgcag ttaaaggcgt cacaggacat gaagtctgca attatttctg gaatgttgac   1320

gttcgcaatg actgggaaac aactatagaa aactttcatg tggtggaaac attagctgat   1380

aatgcaatca tcatttatca aacacacaag agggtgtggc ctgcttctca gcgagacgta   1440

ttatatcttt ctgtcattcg aaagatacca gccttgactg aaaatgaccc tgaaacttgg   1500

atagtttgta atttttctgt ggatcatgac agtgctcctc taaacaaccg atgtgtccgt   1560

gccaaaataa atgttgctat gatttgtcaa accttggtaa gcccaccaga gggaaaccag   1620

gaaattagca gggacaacat tctatgcaag attacatatg tagctaatgt gaaccctgga   1680

ggatgggcac cagcctcagt gttaagggca gtggcaaagc gagagtatcc taaatttcta   1740

aaacgtttta cttcttacgt ccaagaaaaa actgcaggaa agcctatttt gttctag      1797
```

<210> SEQ ID NO 15
<211> LENGTH: 598
<212> TYPE: PRT
<213> ORGANISM: Homo sapiens
<220> FEATURE:
<223> OTHER INFORMATION: CERT S132A protein

<400> SEQUENCE: 15

```
Met Ser Asp Asn Gln Ser Trp Asn Ser Ser Gly Ser Glu Glu Asp Pro
1               5                   10                  15

Glu Thr Glu Ser Gly Pro Pro Val Glu Arg Cys Gly Val Leu Ser Lys
            20                  25                  30

Trp Thr Asn Tyr Ile His Gly Trp Gln Asp Arg Trp Val Val Leu Lys
        35                  40                  45

Asn Asn Ala Leu Ser Tyr Tyr Lys Ser Glu Asp Glu Thr Glu Tyr Gly
    50                  55                  60

Cys Arg Gly Ser Ile Cys Leu Ser Lys Ala Val Ile Thr Pro His Asp
65                  70                  75                  80

Phe Asp Glu Cys Arg Phe Asp Ile Ser Val Asn Asp Ser Val Trp Tyr
                85                  90                  95

Leu Arg Ala Gln Asp Pro Asp His Arg Gln Gln Trp Ile Asp Ala Ile
            100                 105                 110

Glu Gln His Lys Thr Glu Ser Gly Tyr Gly Ser Glu Ser Ser Leu Arg
        115                 120                 125

Arg His Gly Ala Met Val Ser Leu Val Ser Gly Ala Ser Gly Tyr Ser
    130                 135                 140

Ala Thr Ser Thr Ser Ser Phe Lys Lys Gly His Ser Leu Arg Glu Lys
145                 150                 155                 160

Leu Ala Glu Met Glu Thr Phe Arg Asp Ile Leu Cys Arg Gln Val Asp
                165                 170                 175

Thr Leu Gln Lys Tyr Phe Asp Ala Cys Ala Asp Ala Val Ser Lys Asp
            180                 185                 190

Glu Leu Gln Arg Asp Lys Val Val Glu Asp Asp Glu Asp Asp Phe Pro
        195                 200                 205
```

-continued

```
Thr Thr Arg Ser Asp Gly Asp Phe Leu His Ser Thr Asn Gly Asn Lys
    210                 215                 220

Glu Lys Leu Phe Pro His Val Thr Pro Lys Gly Ile Asn Gly Ile Asp
225                 230                 235                 240

Phe Lys Gly Glu Ala Ile Thr Phe Lys Ala Thr Thr Ala Gly Ile Leu
                245                 250                 255

Ala Thr Leu Ser His Cys Ile Glu Leu Met Val Lys Arg Glu Asp Ser
            260                 265                 270

Trp Gln Lys Arg Leu Asp Lys Glu Thr Glu Lys Lys Arg Arg Thr Glu
        275                 280                 285

Glu Ala Tyr Lys Asn Ala Met Thr Glu Leu Lys Lys Lys Ser His Phe
    290                 295                 300

Gly Gly Pro Asp Tyr Glu Glu Gly Pro Asn Ser Leu Ile Asn Glu Glu
305                 310                 315                 320

Glu Phe Phe Asp Ala Val Glu Ala Ala Leu Asp Arg Gln Asp Lys Ile
                325                 330                 335

Glu Glu Gln Ser Gln Ser Glu Lys Val Arg Leu His Trp Pro Thr Ser
            340                 345                 350

Leu Pro Ser Gly Asp Ala Phe Ser Ser Val Gly Thr His Arg Phe Val
        355                 360                 365

Gln Lys Val Glu Glu Met Val Gln Asn His Met Thr Tyr Ser Leu Gln
    370                 375                 380

Asp Val Gly Gly Asp Ala Asn Trp Gln Leu Val Val Glu Glu Gly Glu
385                 390                 395                 400

Met Lys Val Tyr Arg Arg Glu Val Glu Glu Asn Gly Ile Val Leu Asp
                405                 410                 415

Pro Leu Lys Ala Thr His Ala Val Lys Gly Val Thr Gly His Glu Val
            420                 425                 430

Cys Asn Tyr Phe Trp Asn Val Asp Val Arg Asn Asp Trp Glu Thr Thr
        435                 440                 445

Ile Glu Asn Phe His Val Val Glu Thr Leu Ala Asp Asn Ala Ile Ile
    450                 455                 460

Ile Tyr Gln Thr His Lys Arg Val Trp Pro Ala Ser Gln Arg Asp Val
465                 470                 475                 480

Leu Tyr Leu Ser Val Ile Arg Lys Ile Pro Ala Leu Thr Glu Asn Asp
                485                 490                 495

Pro Glu Thr Trp Ile Val Cys Asn Phe Ser Val Asp His Asp Ser Ala
            500                 505                 510

Pro Leu Asn Asn Arg Cys Val Arg Ala Lys Ile Asn Val Ala Met Ile
        515                 520                 525

Cys Gln Thr Leu Val Ser Pro Pro Glu Gly Asn Gln Glu Ile Ser Arg
    530                 535                 540

Asp Asn Ile Leu Cys Lys Ile Thr Tyr Val Ala Asn Val Asn Pro Gly
545                 550                 555                 560

Gly Trp Ala Pro Ala Ser Val Leu Arg Ala Val Ala Lys Arg Glu Tyr
                565                 570                 575

Pro Lys Phe Leu Lys Arg Phe Thr Ser Tyr Val Gln Glu Lys Thr Ala
            580                 585                 590

Gly Lys Pro Ile Leu Phe
        595
```

<210> SEQ ID NO 16
<211> LENGTH: 669
<212> TYPE: DNA
<213> ORGANISM: Homo sapiens
<220> FEATURE:
<223> OTHER INFORMATION: START Domain CERT cDNA

<400> SEQUENCE: 16

```
agatttgtcc aaaaggttga agagatggtg cagaaccaca tgacttactc attacaggat      60

gtaggcggag atgccaattg gcagttggtt gtagaagaag gagaaatgaa ggtatacaga     120

agagaagtag aagaaaatgg gattgttctg gatcctttaa aagctaccca tgcagttaaa     180

ggcgtcacag gacatgaagt ctgcaattat ttctggaatg ttgacgttcg caatgactgg     240

gaaacaacta tagaaaactt tcatgtggtg gaaacattag ctgataatgc aatcatcatt     300

tatcaaacac acaagagggt gtggcctgct tctcagcgag acgtattata tctttctgtc     360

attcgaaaga taccagcctt gactgaaaat gaccctgaaa cttggatagt ttgtaatttt     420

tctgtggatc atgacagtgc tcctctaaac aaccgatgtg tccgtgccaa aataaatgtt     480

gctatgattt gtcaaacctt ggtaagccca ccagagggaa accaggaaat tagcagggac     540

aacattctat gcaagattac atatgtagct aatgtgaacc ctggaggatg ggcaccagcc     600

tcagtgttaa gggcagtggc aaagcgagag tatcctaaat ttctaaaacg ttttacttct     660

tacgtccaa                                                             669
```

<210> SEQ ID NO 17
<211> LENGTH: 223
<212> TYPE: PRT
<213> ORGANISM: Homo sapiens
<220> FEATURE:
<223> OTHER INFORMATION: START Domain CERT protein

<400> SEQUENCE: 17

```
Arg Phe Val Gln Lys Val Glu Glu Met Val Gln Asn His Met Thr Tyr
1               5                   10                  15

Ser Leu Gln Asp Val Gly Gly Asp Ala Asn Trp Gln Leu Val Val Glu
            20                  25                  30

Glu Gly Glu Met Lys Val Tyr Arg Arg Glu Val Glu Glu Asn Gly Ile
        35                  40                  45

Val Leu Asp Pro Leu Lys Ala Thr His Ala Val Lys Gly Val Thr Gly
    50                  55                  60

His Glu Val Cys Asn Tyr Phe Trp Asn Val Asp Val Arg Asn Asp Trp
65                  70                  75                  80

Glu Thr Thr Ile Glu Asn Phe His Val Val Glu Thr Leu Ala Asp Asn
                85                  90                  95

Ala Ile Ile Ile Tyr Gln Thr His Lys Arg Val Trp Pro Ala Ser Gln
            100                 105                 110

Arg Asp Val Leu Tyr Leu Ser Val Ile Arg Lys Ile Pro Ala Leu Thr
        115                 120                 125

Glu Asn Asp Pro Glu Thr Trp Ile Val Cys Asn Phe Ser Val Asp His
    130                 135                 140

Asp Ser Ala Pro Leu Asn Asn Arg Cys Val Arg Ala Lys Ile Asn Val
145                 150                 155                 160

Ala Met Ile Cys Gln Thr Leu Val Ser Pro Pro Glu Gly Asn Gln Glu
                165                 170                 175

Ile Ser Arg Asp Asn Ile Leu Cys Lys Ile Thr Tyr Val Ala Asn Val
            180                 185                 190

Asn Pro Gly Gly Trp Ala Pro Ala Ser Val Leu Arg Ala Val Ala Lys
        195                 200                 205

Arg Glu Tyr Pro Lys Phe Leu Lys Arg Phe Thr Ser Tyr Val Gln
    210                 215                 220
```

<210> SEQ ID NO 18
<211> LENGTH: 658
<212> TYPE: DNA
<213> ORGANISM: Homo sapiens
<220> FEATURE:
<223> OTHER INFORMATION: START Domain CERT L cDNA

<400> SEQUENCE: 18
caggttgaag agatggtgca gaaccacatg acttactcat tacaggatgt aggcggagat 60
gccaattggc agttggttgt agaagaagga gaaatgaagg tatacagaag agaagtagaa 120
gaaaatggga ttgttctgga tcctttaaaa gctacccatg cagttaaagg cgtcacagga 180
catgaagtct gcaattattt ctggaatgtt gacgttcgca atgactggga aacaactata 240
gaaaactttc atgtggtgga aacattagct gataatgcaa tcatcattta tcaaacacac 300
aagagggtgt ggcctgcttc tcagcgagac gtattatatc tttctgtcat tcgaaagata 360
ccagccttga ctgaaaatga ccctgaaact tggatagttt gtaatttttc tgtggatcat 420
gacagtgctc ctctaaacaa ccgatgtgtc cgtgccaaaa taaatgttgc tatgatttgt 480
caaaccttgg taagcccacc agagggaaac caggaaatta gcagggacaa cattctatgc 540
aagattacat atgtagctaa tgtgaaccct ggaggatggg caccagcctc agtgttaagg 600
gcagtggcaa agcgagagta tcctaaattt ctaaaacgtt ttacttctta cgtccaag 658

<210> SEQ ID NO 19
<211> LENGTH: 219
<212> TYPE: PRT
<213> ORGANISM: Homo sapiens
<220> FEATURE:
<223> OTHER INFORMATION: START Domain CERT L protein

<400> SEQUENCE: 19

Gln Val Glu Glu Met Val Gln Asn His Met Thr Tyr Ser Leu Gln Asp
1 5 10 15

Val Gly Gly Asp Ala Asn Trp Gln Leu Val Val Glu Glu Gly Glu Met
20 25 30

Lys Val Tyr Arg Arg Glu Val Glu Glu Asn Gly Ile Val Leu Asp Pro
35 40 45

Leu Lys Ala Thr His Ala Val Lys Gly Val Thr Gly His Glu Val Cys
50 55 60

Asn Tyr Phe Trp Asn Val Asp Val Arg Asn Asp Trp Glu Thr Thr Ile
65 70 75 80

Glu Asn Phe His Val Val Glu Thr Leu Ala Asp Asn Ala Ile Ile Ile
85 90 95

Tyr Gln Thr His Lys Arg Val Trp Pro Ala Ser Gln Arg Asp Val Leu
100 105 110

Tyr Leu Ser Val Ile Arg Lys Ile Pro Ala Leu Thr Glu Asn Asp Pro
115 120 125

Glu Thr Trp Ile Val Cys Asn Phe Ser Val Asp His Asp Ser Ala Pro
130 135 140

Leu Asn Asn Arg Cys Val Arg Ala Lys Ile Asn Val Ala Met Ile Cys
145 150 155 160

Gln Thr Leu Val Ser Pro Pro Glu Gly Asn Gln Glu Ile Ser Arg Asp
165 170 175

Asn Ile Leu Cys Lys Ile Thr Tyr Val Ala Asn Val Asn Pro Gly Gly
180 185 190

Trp Ala Pro Ala Ser Val Leu Arg Ala Val Ala Lys Arg Glu Tyr Pro

-continued

```
        195                 200                 205

Lys Phe Leu Lys Arg Phe Thr Ser Tyr Val Gln
    210                 215


<210> SEQ ID NO 20
<211> LENGTH: 2264
<212> TYPE: DNA
<213> ORGANISM: Homo sapiens
<220> FEATURE:
<223> OTHER INFORMATION: StarD4 cDNA

<400> SEQUENCE: 20

actgttgaga gcggtgtgag gtgcttggta gcgcgccgta gctgcttcca cgtccttgct      60

tcacctcagg taaagagaga agtaatggaa ggcctgtctg atgttgcttc ttttgcaact     120

aaacttaaaa acactctcat ccagtaccat agcattgaag aagataagtg gcgagttgct     180

aagaaaacga aagatgtaac tgtttggaga aaaccctcag aagaatttaa tggatatctc     240

tacaaagccc aaggtgttat agatgacctt gtctatagta taatagacca tatacgccca     300

gggccttgtc gtttggattg ggacagcttg atgacttctt tggatattct ggagaacttt     360

gaagagaatt gctgtgtgat gcgttacact actgctggtc agctttggaa tataatttcc     420

ccaagagaat ttgttgattt ctcctatact gtgggctata aagaagggct tttatcttgt     480

ggaataagtc ttgactggga tgaaaagaga ccagaatttg ttcgaggata taaccatccc     540

tgtggttggt tttgtgttcc acttaaagac aacccaaacc agagtctttt gacaggatat     600

attcagacag atctgcgtgg gatgattcct cagtctgcgg tagatacagc catggcaagc     660

actttaacca acttctatgg tgatttacga aaagctttat gagaggcaaa atacattcaa     720

acttgtagta ctacagatca actctctcag ctacatggcc tgtaaaaatc attgattcca     780

cttttctgca tagccggtag aaaaatttga aatgtttttg gttcactagt acaatgtttg     840

gttttattcc taaagtaaat agctatctaa gagagggcat tttcactttt ttttttttaa     900

attttgagac aggctctcac tctgttgccc atgctggagg gcagtggtat gatcacagct     960

cactgcagct ttgatctgac cgctcaaggg gttattctac ctcagcctcc tgaatagctg    1020

ggaatacagg tgcacgccac tatgcatggc taatttttgt ttaatttttt gtagagatgt    1080

ggtcacactg tgttgcccag gctggtcttg aactcctggc ctcaagtcat tccccacctt    1140

agcctcccaa agtgttggga ttataagcgt gagccaccat gcctggcccc aatttaaaat    1200

gtggaattca gttggtgtcc aagacttatc ttgagactct taaaagcatc agtctgtaac    1260

tagaacaaat acagtcttag atttacccaa gtgcctagat atcattttat aatgattaga    1320

attgagtatt gtgggtcccc taattctgtg ggtgccttaa gtgagaattt ctaaatgatt    1380

ttcacattct aaatgacttt gggttttgaa ctctccatct agtttacttc taaaatggga    1440

acttgaggca attcaggtat ccaggcaaat ctttgtatat atttttttgt gtacatgcac    1500

acatctcgaa atccatttcc gtgtttaatg ttagttgttt atgtgttagt attcctgtgt    1560

ctactgtttt gttgttgtta atatgggtaa agtgagccct gaaatacatg ctaaacaaga    1620

catgaaattc agaaaggtac atagtgtttc aagtgcatgg tagtttgatc tgtgttttac    1680

tttattgtgt tttcttgagt gtaaagaaag aataaatcaa agttcttcat acccattttg    1740

acaaagtgga acagtggagc tgttttttgc ttttgttttt atttattttt tgccactggt    1800

gatgatagat ttcaaaaaac aaaaggtggc agcagcacaa tgttcatggt gaattatctc    1860

atagtatcta gattgatcaa gatctgacag aaggaatgca caaaggattc tatattctta    1920

atgatttatt aattaccagg atccttttct aaattgaatg tacttttgaa ttactaggtt    1980
```

```
tcttcttttt ttttgttctg caatagtgaa agaaaactca gtagtttagt ttcagtttct   2040

catggaaatt ggtaaatgtt agttttgact tcatctattt tttatttgtt tttattagcg   2100

tagagtagga agtctcatat tctactgttc tatctaggat ggtgaaattc caaaggtgcc   2160

taacttgagt aagggatttg tgacaagata gtacacatta ctataagggc tattatttcc   2220

tgaactggat gtccctaaaa gcaaataaac tgcccactat ctct                    2264


<210> SEQ ID NO 21
<211> LENGTH: 205
<212> TYPE: PRT
<213> ORGANISM: Homo sapiens
<220> FEATURE:
<223> OTHER INFORMATION: StarD4 protein

<400> SEQUENCE: 21

Met Glu Gly Leu Ser Asp Val Ala Ser Phe Ala Thr Lys Leu Lys Asn
1               5                   10                  15

Thr Leu Ile Gln Tyr His Ser Ile Glu Glu Asp Lys Trp Arg Val Ala
            20                  25                  30

Lys Lys Thr Lys Asp Val Thr Val Trp Arg Lys Pro Ser Glu Glu Phe
        35                  40                  45

Asn Gly Tyr Leu Tyr Lys Ala Gln Gly Val Ile Asp Asp Leu Val Tyr
    50                  55                  60

Ser Ile Ile Asp His Ile Arg Pro Gly Pro Cys Arg Leu Asp Trp Asp
65                  70                  75                  80

Ser Leu Met Thr Ser Leu Asp Ile Leu Glu Asn Phe Glu Glu Asn Cys
                85                  90                  95

Cys Val Met Arg Tyr Thr Thr Ala Gly Gln Leu Trp Asn Ile Ile Ser
            100                 105                 110

Pro Arg Glu Phe Val Asp Phe Ser Tyr Thr Val Gly Tyr Lys Glu Gly
        115                 120                 125

Leu Leu Ser Cys Gly Ile Ser Leu Asp Trp Asp Glu Lys Arg Pro Glu
    130                 135                 140

Phe Val Arg Gly Tyr Asn His Pro Cys Gly Trp Phe Cys Val Pro Leu
145                 150                 155                 160

Lys Asp Asn Pro Asn Gln Ser Leu Leu Thr Gly Tyr Ile Gln Thr Asp
                165                 170                 175

Leu Arg Gly Met Ile Pro Gln Ser Ala Val Asp Thr Ala Met Ala Ser
            180                 185                 190

Thr Leu Thr Asn Phe Tyr Gly Asp Leu Arg Lys Ala Leu
        195                 200                 205


<210> SEQ ID NO 22
<211> LENGTH: 1344
<212> TYPE: DNA
<213> ORGANISM: Homo sapiens
<220> FEATURE:
<223> OTHER INFORMATION: StarD5 cDNA

<400> SEQUENCE: 22

gagctccagc ctccaggcac ccgggatcca gcgccgccgc tcataacacc cgcgaccccg     60

cagctaagcg cagctcccga cgcaatggac ccggcgctgg cagcccagat gagcgaggct    120

gtggccgaga agatgctcca gtaccggcgg gacacagcag gctggaagat ttgccgggaa    180

ggcaatggag tttcagtttc ctggaggcca tctgtggagt ttccagggaa cctgtaccga    240

ggagaaggca ttgtatatgg gacactagag gaggtgtggg actgtgtgaa gccagctgtt    300
```

-continued

```
ggaggcctac gagtgaagtg ggatgagaat gtgaccggtt ttgaaattat ccaaagcatc    360

actgacaccc tgtgtgtaag cagaacctcc actccctccg ctgccatgaa gctcatttct    420

cccagagatt ttgtggactt ggtgctagtc aagagatatg aggatgggac catcagttcc    480

aacgccaccc atgtggagca tccgttatgt cccccgaagc caggttttgt gagaggattt    540

aaccatcctt gtggttgctt ctgtgaacct cttccagggg aacccaccaa gaccaacctg    600

gtcacattct tccataccga cctcagcggt tacctcccac agaacgtggt ggactccttc    660

ttcccccgca gcatgacccg gttttatgcc aaccttcaga aagcagtgaa gcaattccat    720

gagtaatgct atcgttactt cttggcaaag aactcccgtg actcatcgag gagctccagc    780

tgttgggaca ccaaggagcc tgggagcacg cagaggcctg tgttcactct ttggaacaag    840

ctgatggact gcgcatctct gagaatgcca accagaggcg gcagcccacc cttcctgcct    900

cctgccccac tcagggttgg cgtgtgatga gccattcatg tgttccaaac tccatctgcc    960

tgttacccaa acacgcctct cctggcaggg tagacccagg cctctaacca tctgacagag   1020

actcggcctg gacaccatgc gatgcactct ggcaccaagg ctttatgtgc ccatcactct   1080

cagagaccac gtttccctga ctgtcataga gaatcatcat cgccactgaa aaccaggccc   1140

tgttgccttt taagcatgta ccgctccctc agtcctgtgc tgcagccccc caaatatatt   1200

tttctgatat agaccttgta tatggcttta atgccgcaaa atatttattt ttccttaaaa   1260

aaggtgtcaa cttggaaata atggtttaaa aacaggataa gcattaagga aaaacaaaaa   1320

aaaaaaaaaa aaaaaaaaaa aaaa                                          1344


<210> SEQ ID NO 23
<211> LENGTH: 213
<212> TYPE: PRT
<213> ORGANISM: Homo sapiens
<220> FEATURE:
<223> OTHER INFORMATION: StarD5 protein

<400> SEQUENCE: 23

Met Asp Pro Ala Leu Ala Ala Gln Met Ser Glu Ala Val Ala Glu Lys
1               5                   10                  15

Met Leu Gln Tyr Arg Arg Asp Thr Ala Gly Trp Lys Ile Cys Arg Glu
            20                  25                  30

Gly Asn Gly Val Ser Val Ser Trp Arg Pro Ser Val Glu Phe Pro Gly
        35                  40                  45

Asn Leu Tyr Arg Gly Glu Gly Ile Val Tyr Gly Thr Leu Glu Glu Val
    50                  55                  60

Trp Asp Cys Val Lys Pro Ala Val Gly Gly Leu Arg Val Lys Trp Asp
65                  70                  75                  80

Glu Asn Val Thr Gly Phe Glu Ile Ile Gln Ser Ile Thr Asp Thr Leu
                85                  90                  95

Cys Val Ser Arg Thr Ser Thr Pro Ser Ala Ala Met Lys Leu Ile Ser
            100                 105                 110

Pro Arg Asp Phe Val Asp Leu Val Leu Val Lys Arg Tyr Glu Asp Gly
        115                 120                 125

Thr Ile Ser Ser Asn Ala Thr His Val Glu His Pro Leu Cys Pro Pro
    130                 135                 140

Lys Pro Gly Phe Val Arg Gly Phe Asn His Pro Cys Gly Cys Phe Cys
145                 150                 155                 160

Glu Pro Leu Pro Gly Glu Pro Thr Lys Thr Asn Leu Val Thr Phe Phe
                165                 170                 175

His Thr Asp Leu Ser Gly Tyr Leu Pro Gln Asn Val Val Asp Ser Phe
```

180 185 190

Phe Pro Arg Ser Met Thr Arg Phe Tyr Ala Asn Leu Gln Lys Ala Val
195 200 205

Lys Gln Phe His Glu
210

<210> SEQ ID NO 24
<211> LENGTH: 663
<212> TYPE: DNA
<213> ORGANISM: Homo sapiens
<220> FEATURE:
<223> OTHER INFORMATION: StarD6 cDNA

<400> SEQUENCE: 24
atggacttca aggcaattgc ccaacaaact gcccaagaag ttttaggtta taatcgagat 60
acatcaggct ggaaagtggt taaaacttca aaaaagataa ctgtttccag taaggcttct 120
agaaaattcc atggaaatct atatcgtgtt gaagggataa ttccagaatc accagctaaa 180
ctatctgatt tcctctacca aactggagac agaattacat gggataaatc attgcaagtg 240
tataatatgg tacacaggat tgattcggac acattcatat gtcataccat tacacaaagt 300
tttgccgtgg gctccatttc ccctcgagac tttatcgact tagtgtacat caagcgctac 360
gaaggaaata tgaacattat cagttctaaa agtgtggatt ttccagaata tcctccatct 420
tcaaattata tccgcggtta taaccatcct tgtggctttg tatgttcacc aatggaagaa 480
aacccagcat attccaaact agtgatgttt gtccagacag aaatgagagg aaaattgtcc 540
ccatcaataa ttgaaaaaac catgccttcc aacttagtaa acttcatcct caatgcaaaa 600
gatggaataa aggcacacag aactccatca agacgtggat ttcatcataa tagtcattca 660
tga 663

<210> SEQ ID NO 25
<211> LENGTH: 220
<212> TYPE: PRT
<213> ORGANISM: Homo sapiens
<220> FEATURE:
<223> OTHER INFORMATION: StarD6 protein

<400> SEQUENCE: 25

Met Asp Phe Lys Ala Ile Ala Gln Gln Thr Ala Gln Glu Val Leu Gly
1 5 10 15

Tyr Asn Arg Asp Thr Ser Gly Trp Lys Val Val Lys Thr Ser Lys Lys
20 25 30

Ile Thr Val Ser Ser Lys Ala Ser Arg Lys Phe His Gly Asn Leu Tyr
35 40 45

Arg Val Glu Gly Ile Ile Pro Glu Ser Pro Ala Lys Leu Ser Asp Phe
50 55 60

Leu Tyr Gln Thr Gly Asp Arg Ile Thr Trp Asp Lys Ser Leu Gln Val
65 70 75 80

Tyr Asn Met Val His Arg Ile Asp Ser Asp Thr Phe Ile Cys His Thr
85 90 95

Ile Thr Gln Ser Phe Ala Val Gly Ser Ile Ser Pro Arg Asp Phe Ile
100 105 110

Asp Leu Val Tyr Ile Lys Arg Tyr Glu Gly Asn Met Asn Ile Ile Ser
115 120 125

Ser Lys Ser Val Asp Phe Pro Glu Tyr Pro Pro Ser Ser Asn Tyr Ile
130 135 140

Arg Gly Tyr Asn His Pro Cys Gly Phe Val Cys Ser Pro Met Glu Glu

-continued

```
145                 150                 155                 160

Asn Pro Ala Tyr Ser Lys Leu Val Met Phe Val Gln Thr Glu Met Arg
                165                 170                 175

Gly Lys Leu Ser Pro Ser Ile Ile Glu Lys Thr Met Pro Ser Asn Leu
            180                 185                 190

Val Asn Phe Ile Leu Asn Ala Lys Asp Gly Ile Lys Ala His Arg Thr
        195                 200                 205

Pro Ser Arg Arg Gly Phe His His Asn Ser His Ser
    210                 215                 220


<210> SEQ ID NO 26
<211> LENGTH: 1932
<212> TYPE: DNA
<213> ORGANISM: Homo sapiens
<220> FEATURE:
<223> OTHER INFORMATION: PCTP cDNA

<400> SEQUENCE: 26

ccggactgcg gaaggatgga gctggccgcc ggaagcttct cggaggagca gttctgggag     60

gcctgcgccg agctccagca gcccgctctg gccggggccg actggcagct cctagtggag    120

acctcgggca tcagcatcta ccggctgctg gacaagaaga ctggacttca tgagtataaa    180

gtctttggtg ttctggagga ctgctcacca actctactgg cagacatcta tatggactca    240

gattacagaa aacaatggga ccagtatgtt aaagaactct atgaacaaga atgcaacgga    300

gagactgtgg tctactggga agtgaagtac ccttttccca tgtccaacag agactatgtc    360

taccttcggc agcggcgaga cctggacatg gaagggagga agatccatgt gatcctggcc    420

cggagcacct ccatgcctca gcttggcgag aggtctgggg tgatccgggt gaagcaatac    480

aagcagagcc tggcgattga gagtgacggc aagaagggga gcaaagtttt catgtattac    540

ttcgataacc cgggtggcca aattccgtcc tggctcatta actgggccgc caagaatgga    600

gttcctaact tcttgaaaga catggcaaga gcctgtcaga actacctcaa gaaaacctaa    660

gaaagagaac tgggaacatt gcatccatgg gttgatgtct ctggaagtgc aaccacccaa    720

tgtctctgga agtgccacct ggaagtgcca cctggaagtg tctctggaag agcacccacc    780

actgttcagc cttcccctgc tgtttctgtc ttcagaggcc tacacactac cacatccttt    840

ctaagcatgt ttgcctgaca tccagctcac tcgtctgctt cctttctcgc tccccccatc    900

ctgggctggg ctgccttctt ctacagttca atatggggca gactagggaa acctttgctt    960

gcttactatt aggaggggaa gtcttcagta gggaacacga tcattccatt gtgcaatttt   1020

acggggatgg gtgggcggag ggacacaaca aaatttaaga atgactattt gggcgggctg   1080

gctcttttgc agcttgtgat ttcttccagc ttgggagggg ctgctggaag tggcatttcg   1140

ttcagagctg actttcagtg cacccaaact ggatgacgtg ccaatgtcca tttgccttat   1200

gctttgtgga gctgattagg ctgggatttg aggtgataat ccagtaagtc tttcctcgtt   1260

cctacttgtg gaggatcagt agctgttatg atgccagacc atttggagaa gtatcagagg   1320

cctgaccgga cacataatac gacaaccaca tttttcctca tcatccatga ggaaatggat   1380

gatttctctt ttccatatgt cactggggga aaggctgcct gtacctctca agctttgcat   1440

tttactggaa actgaggcgt caagatggct gtggcagcta gcaaaagcaa agatgctttg   1500

tgcatagcct tgtgaaaaag tatctttcta tgcaataaga tgaattttcc tcccagaata   1560

tttagaaatg tagaagggat aacagttcac agccaggtaa aatttaactg gtggcttaat   1620

gactctgcac ctttttctca ggaattctgc ctaagttgtc tgccttttct accaccaaaa   1680
```

agacttttag ttttctatgc tttctcctga attttggtag ggtaagtatt tctatgtcaa 1740
aggcacagcc ttgatgatct cagggaaaaa ttttaatcac tgtgtataat gatactgaac 1800
cttgattaat aacagaaatt caggatgtaa agccacagaa tgggatttat taatgtggga 1860
tacctcagac tgtttgtttt ctttctggga agaaaagtgt gttctataat gaataaatat 1920
agagtggttt tt 1932

<210> SEQ ID NO 27
<211> LENGTH: 214
<212> TYPE: PRT
<213> ORGANISM: Homo sapiens
<220> FEATURE:
<223> OTHER INFORMATION: PCTP protein

<400> SEQUENCE: 27

Met Glu Leu Ala Ala Gly Ser Phe Ser Glu Glu Gln Phe Trp Glu Ala
1 5 10 15

Cys Ala Glu Leu Gln Gln Pro Ala Leu Ala Gly Ala Asp Trp Gln Leu
20 25 30

Leu Val Glu Thr Ser Gly Ile Ser Ile Tyr Arg Leu Leu Asp Lys Lys
35 40 45

Thr Gly Leu His Glu Tyr Lys Val Phe Gly Val Leu Glu Asp Cys Ser
50 55 60

Pro Thr Leu Leu Ala Asp Ile Tyr Met Asp Ser Asp Tyr Arg Lys Gln
65 70 75 80

Trp Asp Gln Tyr Val Lys Glu Leu Tyr Glu Gln Glu Cys Asn Gly Glu
85 90 95

Thr Val Val Tyr Trp Glu Val Lys Tyr Pro Phe Pro Met Ser Asn Arg
100 105 110

Asp Tyr Val Tyr Leu Arg Gln Arg Arg Asp Leu Asp Met Glu Gly Arg
115 120 125

Lys Ile His Val Ile Leu Ala Arg Ser Thr Ser Met Pro Gln Leu Gly
130 135 140

Glu Arg Ser Gly Val Ile Arg Val Lys Gln Tyr Lys Gln Ser Leu Ala
145 150 155 160

Ile Glu Ser Asp Gly Lys Lys Gly Ser Lys Val Phe Met Tyr Tyr Phe
165 170 175

Asp Asn Pro Gly Gly Gln Ile Pro Ser Trp Leu Ile Asn Trp Ala Ala
180 185 190

Lys Asn Gly Val Pro Asn Phe Leu Lys Asp Met Ala Arg Ala Cys Gln
195 200 205

Asn Tyr Leu Lys Lys Thr
210

<210> SEQ ID NO 28
<211> LENGTH: 271
<212> TYPE: PRT
<213> ORGANISM: Artificial Sequence
<220> FEATURE:
<223> OTHER INFORMATION: Description of Artificial Sequence: Synthetic
consensus sequence
<220> FEATURE:
<221> NAME/KEY: MOD_RES
<222> LOCATION: (1)..(1)
<223> OTHER INFORMATION: Ala, Arg, Asn, Asp, Cys, Glu, Gln, Gly, His,
Ile, Leu, Lys, Met, Phe, Pro, Ser, Thr, Trp, Tyr, Val or any
modified amino acid
<220> FEATURE:
<221> NAME/KEY: MOD_RES
<222> LOCATION: (2)..(2)
<223> OTHER INFORMATION: Ala, Cys, Phe, Gly, His, Ile, Lys, Leu, Met,

```
      Arg, Thr, Val, Trp, Tyr or any modified hydrophobic amino acid
<220> FEATURE:
<221> NAME/KEY: MOD_RES
<222> LOCATION: (3)..(4)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (5)..(5)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (6)..(8)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (9)..(9)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (10)..(10)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (11)..(11)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (12)..(12)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (13)..(13)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (14)..(15)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (16)..(16)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (17)..(17)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (18)..(20)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (22)..(38)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (39)..(40)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
```

<222> LOCATION: (41)..(41)
<223> OTHER INFORMATION: Ala, Cys, Asp, Glu, Gly, His, Lys, Asn, Gln, Arg, Ser, Thr or any modified turnlike amino acid
<220> FEATURE:
<221> NAME/KEY: MOD_RES
<222> LOCATION: (42)..(42)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (43)..(61)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (62)..(62)
<223> OTHER INFORMATION: His, Lys, Arg, or any modified positive amino acid
<220> FEATURE:
<221> NAME/KEY: MOD_RES
<222> LOCATION: (63)..(63)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (64)..(64)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (65)..(65)
<223> OTHER INFORMATION: Ala, Cys, Asp, Glu, Gly, His, Lys, Asn, Gln, Arg, Ser, Thr or any modified turnlike amino acid
<220> FEATURE:
<221> NAME/KEY: MOD_RES
<222> LOCATION: (66)..(67)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (68)..(74)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (75)..(75)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (76)..(78)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (79)..(80)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (81)..(81)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (82)..(82)
<223> OTHER INFORMATION: Ala, Cys, Asp, Glu, Gly, His, Lys, Asn, Gln, Arg, Ser, Thr or any modified turnlike amino acid
<220> FEATURE:
<221> NAME/KEY: MOD_RES
<222> LOCATION: (83)..(88)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:

<221> NAME/KEY: MOD_RES
<222> LOCATION: (89)..(89)
<223> OTHER INFORMATION: Ala, Cys, Asp, Glu, Gly, His, Lys, Asn, Gln, Arg, Ser, Thr or any modified turnlike amino acid
<220> FEATURE:
<221> NAME/KEY: MOD_RES
<222> LOCATION: (91)..(92)
<223> OTHER INFORMATION: Cys, Asp, Glu, His, Lys, Asn, Gln, Arg, Ser, Thr or any modified polar amino acid
<220> FEATURE:
<221> NAME/KEY: MOD_RES
<222> LOCATION: (93)..(93)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (94)..(94)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (95)..(107)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (108)..(108)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (109)..(109)
<223> OTHER INFORMATION: Ala, Cys, Asp, Glu, Gly, His, Lys, Asn, Gln, Arg, Ser, Thr or any modified turnlike amino acid
<220> FEATURE:
<221> NAME/KEY: MOD_RES
<222> LOCATION: (110)..(110)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (111)..(111)
<223> OTHER INFORMATION: Ile, Leu, Val or any modified aliphatic amino acid
<220> FEATURE:
<221> NAME/KEY: MOD_RES
<222> LOCATION: (112)..(112)
<223> OTHER INFORMATION: Cys, Asp, Glu, His, Lys, Asn, Gln, Arg, Ser, Thr or any modified polar amino acid
<220> FEATURE:
<221> NAME/KEY: MOD_RES
<222> LOCATION: (113)..(113)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (114)..(114)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (115)..(115)
<223> OTHER INFORMATION: Ala, Cys, Asp, Glu, Gly, His, Lys, Asn, Gln, Arg, Ser, Thr or any modified turnlike amino acid
<220> FEATURE:
<221> NAME/KEY: MOD_RES
<222> LOCATION: (116)..(116)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (117)..(117)
<223> OTHER INFORMATION: Ala, Cys, Asp, Gly, Asn, Pro, Ser, Thr, Val or any modified small amino acid
<220> FEATURE:
<221> NAME/KEY: MOD_RES
<222> LOCATION: (118)..(124)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (125)..(125)
<223> OTHER INFORMATION: Ala, Cys, Asp, Gly, Asn, Pro, Ser, Thr, Val or any modified small amino acid
<220> FEATURE:
<221> NAME/KEY: MOD_RES
<222> LOCATION: (126)..(126)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (127)..(127)
<223> OTHER INFORMATION: Ile, Leu, Val or any modified aliphatic amino acid
<220> FEATURE:
<221> NAME/KEY: MOD_RES
<222> LOCATION: (128)..(128)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (129)..(129)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (130)..(132)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (133)..(133)
<223> OTHER INFORMATION: Ala, Cys, Asp, Glu, Gly, His, Lys, Asn, Gln, Arg, Ser, Thr or any modified turnlike amino acid
<220> FEATURE:
<221> NAME/KEY: MOD_RES
<222> LOCATION: (134)..(135)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (136)..(136)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (137)..(139)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (140)..(140)
<223> OTHER INFORMATION: Ala, Cys, Phe, Gly, His, Ile, Lys, Leu, Met, Arg, Thr, Val, Trp, Tyr or any modified hydrophobic amino acid
<220> FEATURE:
<221> NAME/KEY: MOD_RES
<222> LOCATION: (141)..(141)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any modified amino acid
<220> FEATURE:
<221> NAME/KEY: MOD_RES
<222> LOCATION: (142)..(142)
<223> OTHER INFORMATION: Ala, Cys, Asp, Gly, Asn, Pro, Ser, Thr, Val or any modified small amino acid
<220> FEATURE:
<221> NAME/KEY: MOD_RES
<222> LOCATION: (143)..(143)
<223> OTHER INFORMATION: Ala, Arg, Asn, Asp, Cys, Glu, Gln, Gly, His, Ile, Leu, Lys, Met, Phe, Pro, Ser, Thr, Trp, Tyr, Val or any

```
      modified amino acid
<220> FEATURE:
<221> NAME/KEY: MOD_RES
<222> LOCATION: (145)..(145)
<223> OTHER INFORMATION: Asp, Glu or any modified negative amino acid
<220> FEATURE:
<221> NAME/KEY: MOD_RES
<222> LOCATION: (146)..(147)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (148)..(148)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (149)..(149)
<223> OTHER INFORMATION: Ile, Leu, Val or any modified aliphatic amino
      acid
<220> FEATURE:
<221> NAME/KEY: MOD_RES
<222> LOCATION: (151)..(151)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (152)..(152)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (153)..(153)
<223> OTHER INFORMATION: Cys, Asp, Glu, His, Lys, Asn, Gln, Arg, Ser,
      Thr or any modified polar amino acid
<220> FEATURE:
<221> NAME/KEY: MOD_RES
<222> LOCATION: (154)..(164)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (165)..(166)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (167)..(167)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (168)..(169)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (170)..(170)
<223> OTHER INFORMATION: Ile, Leu, Val or any modified aliphatic amino
      acid
<220> FEATURE:
<221> NAME/KEY: MOD_RES
<222> LOCATION: (171)..(171)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (172)..(173)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (174)..(174)
<223> OTHER INFORMATION: Ser, Thr or any modified alcohol amino acid
<220> FEATURE:
```

```
<221> NAME/KEY: MOD_RES
<222> LOCATION: (175)..(175)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (176)..(176)
<223> OTHER INFORMATION: Cys, Asp, Glu, His, Lys, Asn, Gln, Arg, Ser,
      Thr or any modified polar amino acid
<220> FEATURE:
<221> NAME/KEY: MOD_RES
<222> LOCATION: (177)..(178)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (179)..(179)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (180)..(188)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (189)..(189)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (190)..(191)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (193)..(193)
<223> OTHER INFORMATION: Ala, Cys, Asp, Gly, Asn, Pro, Ser, Thr, Val
      or any modified small amino acid
<220> FEATURE:
<221> NAME/KEY: MOD_RES
<222> LOCATION: (194)..(194)
<223> OTHER INFORMATION: Cys, Asp, Glu, His, Lys, Asn, Gln, Arg, Ser,
      Thr or any modified polar amino acid
<220> FEATURE:
<221> NAME/KEY: MOD_RES
<222> LOCATION: (195)..(196)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (197)..(197)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (198)..(198)
<223> OTHER INFORMATION: Ala, Cys, Asp, Gly, Asn, Pro, Ser, Thr, Val
      or any modified small amino acid
<220> FEATURE:
<221> NAME/KEY: MOD_RES
<222> LOCATION: (199)..(202)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (203)..(203)
<223> OTHER INFORMATION: Cys, Asp, Glu, His, Lys, Asn, Gln, Arg, Ser,
      Thr or any modified polar amino acid
<220> FEATURE:
<221> NAME/KEY: MOD_RES
<222> LOCATION: (204)..(205)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
```

```
<222> LOCATION: (206)..(207)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (208)..(208)
<223> OTHER INFORMATION: Ala, Cys, Asp, Gly, Asn, Pro, Ser, Thr, Val
      or any modified small amino acid
<220> FEATURE:
<221> NAME/KEY: MOD_RES
<222> LOCATION: (209)..(220)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (221)..(221)
<223> OTHER INFORMATION: Ala, Cys, Asp, Gly, Asn, Pro, Ser, Thr, Val
      or any modified small amino acid
<220> FEATURE:
<221> NAME/KEY: MOD_RES
<222> LOCATION: (222)..(222)
<223> OTHER INFORMATION: Cys, Asp, Glu, His, Lys, Asn, Gln, Arg, Ser,
      Thr or any modified polar amino acid
<220> FEATURE:
<221> NAME/KEY: MOD_RES
<222> LOCATION: (223)..(225)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (226)..(226)
<223> OTHER INFORMATION: Ile, Leu, Val or any modified aliphatic amino
      acid
<220> FEATURE:
<221> NAME/KEY: MOD_RES
<222> LOCATION: (227)..(228)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (229)..(229)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (230)..(230)
<223> OTHER INFORMATION: Asp, Glu or any modified negative amino acid
<220> FEATURE:
<221> NAME/KEY: MOD_RES
<222> LOCATION: (231)..(231)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (232)..(232)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (233)..(233)
<223> OTHER INFORMATION: Ala, Cys, Asp, Gly, Asn, Pro, Ser, Thr, Val
      or any modified small amino acid
<220> FEATURE:
<221> NAME/KEY: MOD_RES
<222> LOCATION: (234)..(240)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (241)..(241)
<223> OTHER INFORMATION: Cys, Asp, Glu, His, Lys, Asn, Gln, Arg, Ser,
      Thr or any modified polar amino acid
<220> FEATURE:
<221> NAME/KEY: MOD_RES
<222> LOCATION: (242)..(242)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
```

```
      modified amino acid
<220> FEATURE:
<221> NAME/KEY: MOD_RES
<222> LOCATION: (243)..(244)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (245)..(245)
<223> OTHER INFORMATION: Cys, Asp, Glu, His, Lys, Asn, Gln, Arg, Ser,
      Thr or any modified polar amino acid
<220> FEATURE:
<221> NAME/KEY: MOD_RES
<222> LOCATION: (246)..(246)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (247)..(248)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (249)..(249)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (250)..(250)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (251)..(251)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (252)..(252)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (253)..(254)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (255)..(256)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (257)..(257)
<223> OTHER INFORMATION: Cys, Asp, Glu, His, Lys, Asn, Gln, Arg, Ser,
      Thr or any modified polar amino acid
<220> FEATURE:
<221> NAME/KEY: MOD_RES
<222> LOCATION: (258)..(261)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (262)..(262)
<223> OTHER INFORMATION: Ala, Cys, Phe, Gly, His, Ile, Lys, Leu, Met,
      Arg, Thr, Val, Trp, Tyr or any modified hydrophobic amino acid
<220> FEATURE:
<221> NAME/KEY: MOD_RES
<222> LOCATION: (263)..(264)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (265)..(265)
<223> OTHER INFORMATION: Ala, Cys, Phe, Gly, His, Ile, Lys, Leu, Met,
      Arg, Thr, Val, Trp, Tyr or any modified hydrophobic amino acid
```

```
<220> FEATURE:
<221> NAME/KEY: MOD_RES
<222> LOCATION: (266)..(266)
<223> OTHER INFORMATION: Cys, Asp, Glu, His, Lys, Asn, Gln, Arg, Ser,
      Thr or any modified polar amino acid
<220> FEATURE:
<221> NAME/KEY: MOD_RES
<222> LOCATION: (267)..(267)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (268)..(268)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (269)..(269)
<223> OTHER INFORMATION: Ala, Cys, Asp, Glu, Gly, His, Lys, Asn, Gln,
      Arg, Ser, Thr or any modified turnlike amino acid
<220> FEATURE:
<221> NAME/KEY: MOD_RES
<222> LOCATION: (270)..(270)
<223> OTHER INFORMATION: Ala, Arg, Asn, Asp, Cys, Glu, Gln, Gly, His,
      Ile, Leu, Lys, Met, Phe, Pro, Ser, Thr, Trp, Tyr, Val or any
      modified amino acid
<220> FEATURE:
<221> NAME/KEY: MOD_RES
<222> LOCATION: (271)..(271)
<223> OTHER INFORMATION: Cys, Asp, Glu, His, Lys, Asn, Gln, Arg, Ser,
      Thr or any modified polar amino acid

<400> SEQUENCE: 28

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Trp Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Trp Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa Xaa Xaa Arg
    130                 135                 140

Xaa Xaa Xaa Xaa Xaa Arg Xaa Xaa Xaa Xaa Xaa Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Xaa Xaa Xaa Xaa Xaa Xaa Xaa Xaa Arg
            180                 185                 190

Xaa Xaa Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Xaa Xaa Xaa Xaa Xaa Xaa Xaa Xaa Xaa
    210                 215                 220

Xaa Xaa Xaa Xaa Xaa Xaa Xaa Xaa Xaa Xaa Xaa Xaa Xaa Xaa Xaa Xaa
225                 230                 235                 240
```

```
Xaa Xaa Xaa Xaa Xaa Xaa Xaa Xaa Xaa Xaa Xaa Xaa Xaa Xaa Xaa Xaa
                245                 250                 255

Xaa Xaa Xaa Xaa Xaa Xaa Xaa Xaa Xaa Xaa Xaa Xaa Xaa Xaa Xaa
            260                 265                 270


<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Phe Phe Ala Thr
1


<210> SEQ ID NO 30
<211> LENGTH: 202
<212> TYPE: PRT
<213> ORGANISM: Rattus sp.

<400> SEQUENCE: 30

His Phe Leu Gln Asp Cys Val Asp Gly Leu Phe Lys Glu Val Lys Glu
1               5                   10                  15

Lys Phe Lys Gly Trp Val Ser Tyr Pro Thr Ser Glu Gln Ala Glu Leu
            20                  25                  30

Ser Tyr Lys Lys Val Ser Glu Gly Pro Pro Leu Arg Leu Trp Arg Ala
        35                  40                  45

Thr Ile Glu Val Pro Ala Ala Pro Glu Glu Ile Leu Lys Arg Leu Leu
    50                  55                  60

Lys Glu Gln His Leu Trp Asp Val Asp Leu Leu Asp Ser Lys Val Ile
65                  70                  75                  80

Glu Ile Leu Asp Ser Gln Thr Glu Ile Tyr Gln Tyr Val Gln Asn Ser
                85                  90                  95

Met Ala Pro His Pro Ala Arg Asp Tyr Val Val Leu Arg Thr Trp Arg
            100                 105                 110

Thr Asn Leu Pro Arg Gly Ala Cys Ala Leu Leu Phe Thr Ser Val Asp
        115                 120                 125

His Asp Arg Ala Pro Val Ala Gly Val Arg Val Asn Val Leu Leu Ser
    130                 135                 140

Arg Tyr Leu Ile Glu Pro Cys Gly Ser Gly Lys Ser Lys Leu Thr Tyr
145                 150                 155                 160

Met Cys Arg Ala Asp Leu Arg Gly His Met Pro Glu Trp Tyr Thr Lys
                165                 170                 175

Ser Phe Gly His Leu Cys Ala Ala Glu Val Val Lys Ile Arg Asp Ser
            180                 185                 190

Phe Ser Asn Gln Ser Thr Glu Ser Lys Asp
        195                 200
```

PROTEIN PRODUCTION

RELATED CASES

This application claims priority benefit from EP 07103406.0, filed Mar. 2, 2007, EP 07104226.1, filed Mar. 15, 2007, EP 07116358.8, filed Sep. 13, 2007, and U.S. Provisional Patent Application No. 60/893,025, filed Mar. 5, 2007, and the contents of which are all incorporated herein.

BACKGROUND OF THE INVENTION

1. Technical Field

The invention concerns the field of cell culture technology. It concerns a method for producing proteins as well as a method to generate novel expression vectors and host cells for biopharmaceutical manufacturing. The invention further concerns pharmaceutical compositions and methods of treatment.

2. Background

The market for biopharmaceuticals for use in human therapy continues to grow at a high rate with 270 new biopharmaceuticals being evaluated in clinical studies and estimated sales of 30 billions in 2003 (Werner, 2004). Biopharmaceuticals can be produced from various host cell systems, including bacterial cells, yeast cells, insect cells, plant cells and mammalian cells including human-derived cell lines. Currently, an increasing number of biopharmaceuticals is produced from eukaryotic cells due to their ability to correctly process and modify human proteins. Successful and high yield production of biopharmaceuticals from these cells is thus crucial and depends highly on the characteristics of the recombinant monoclonal cell line used in the process. Therefore, there is an urgent need to generate new host cell systems with improved properties and to establish methods to culture producer cell lines with high specific productivities as a basis for high yield processes.

Early approaches focused on process design and reactor design. Now the main improvements are driven by media formulation development and genetically engineering of host cells. The most common industrial mammalian host cell systems for the production of biopharmaceuticals are immortalized Chinese hamster ovary (CHO) cell lines (Wurm, 2004).

Initial metabolic engineering strategies to improve mammalian production cell lines focused on their ability to grow in suspension in serum free media. Stable expression of transferrin and insulin-like growth factor 1 (IGF-1) in CHO-K1 cells resulted in a cell line able to proliferate under protein-free conditions (Pak et al., 1996). Further approaches to improve the production cell lines included the use of regulatory DNA elements on the transfection vectors aimed to target or create transcriptional hot spots. Regulatory elements such as S/MARs (Scaffold/matrix-associated regions) which effect chromatin structure and UCOEs (Ubiquitous chromatin opening elements) derived from house keeping genes were both shown to positively effect specific productivities of recombinant proteins produced from CHO cell lines (Barnes and Dickson, 2006).

As apoptosis has been shown to be the predominant cause of cell death in mammalian cell culture production processes (al-Rubeai and Singh, 1998) the effect of expression of anti-apoptotic genes in mammalian host cells on culture viability was thoroughly investigated. Most antiapoptosis engineering strategies are focused on the overexpression of anti-apoptotic genes of the bcl-2 family (e.g. bcl-1 or bcl-xL; (Kaufmann and Fussenegger, 2003). By increasing the cellular resistance to apoptotic stimuli during fermentation, such as nutrient depletion and waste byproduct accumulation, production processes with apoptosis engineered cell lines showed prolonged culture viability and in some cases an increase in product yield (Chiang and Sisk, 2005).

Since most biopharmaceutical products are proteins that are secreted from the cells during the production process, the secretory transport machinery of the production cell line is another interesting target for novel host cell engineering strategies.

Protein secretion is a complex multi-step mechanism: Proteins destined to be transported to the extracellular space or the outer plasma membrane are first co-translationally imported into the endoplasmic reticulum. From there, they are packed in lipid vesicles and transported to the Golgi apparatus and finally from the trans-Golgi network (TGN) to the plasma membrane where they are released into the culture medium (Seth et al., 2006).

The yield of any biopharmaceutical production process depends largely on the amount of protein product that the producing cells secrete per time when grown under process conditions. Many complex biochemical intracellular processes are necessary to synthesize and secrete a therapeutic protein from a eukaryotic cell. All these steps such as transcription, RNA transport, translation, post-translational modification and protein transport are tightly regulated in the wild-type host cell line and will impact on the specific productivity of any producer cell line derived from this host.

Many engineering approaches have employed the growing understanding of the molecular networks that drive processes such as transcription and translation to increase the yield of these steps in protein production. However, as for any multi-step production process, widening a bottle-neck during early steps of the process chain possibly creates bottle necks further downstream, especially post translation. Up to a certain threshold, the specific productivity of a production cell has been reported to correlate linearly with the level of product gene transcription (Barnes et al., 2007). Further enhancement of product expression at the mRNA level, however, may lead to an overload of the protein synthesis, folding or transport machinery, resulting in intracellular accumulation of the protein product. Indeed, this can be frequently observed in current manufacturing processes (FIG. 1).

Specific targeted engineering approaches aimed to address this problem and to efficiently improve the secretion of protein products from eukaryotic cells are hampered by the current lack of understanding of the complex regulatory network that drives the transport of proteins to the plasma membrane.

The first studies on engineering the intracellular transport of secreted therapeutic proteins were centered around the overexpression of molecular chaperones like binding protein BiP/GRP78, protein disulfide isomerase (PDI). Chaperones are cellular proteins hosted within the endoplasmic reticulum (ER) and assist the folding and assembly of newly synthesised proteins. In contrast to what could be expected, BiP overexpression in mammalian cells has been shown to reduce rather than increase the secretion of proteins it associates with (Domer and Kaufman, 1994). Likewise, PDI overexpression in CHO cells reduced the expression of a TNFR:FC fusion protein (Davis et al., 2000), whereas the specific production rate of an antibody was increased by 40% (Borth et al., 2005). A possible explanation for these surprising findings, that the increase of the cell's protein folding capacity creates a production bottle neck further downstream, is supported by a report describing ER to cis-Golgi transport problems for IFN-gamma production in a CHO cell line (Hooker et al., 1999).

Another recent approach to increase the secretion capacity of mammalian cells is the heterologous overexpression of the transcription factor X-box binding protein 1 (XBP-1). XBP-1 is one of the master-regulators in the differentiation of plasma cells, a specialized cell type optimized for high-level production and secretion of antibodies (Iwakoshi et al., 2003). XBP-1 regulates this process by binding to the so called ER stress responsive elements (ERSE) within the promoters of a wide spectrum of secretory pathway genes, resulting in (i) a physical expansion of the ER, (ii) increased mitochondrial mass and function, (iii) larger cell size and (iv) enhanced total protein synthesis (Shaffer et al., 2004).

Recently, attempts were described to increase protein secretion by overexpressing XBP-1 in non-plasma cells, especially production cell lines. In CHO-K1 cells, the production level of two reporter proteins (secreted alkaline phospatase (SEAP) and secreted alpha-amylase (SAMY)) was shown to increase after XBP-1 introduction in CHO-K1 cells. However, no effect could be demonstrated in transient studies with other cell lines such as HEK293, HeLa or HT-1080 cells (Tigges and Fussenegger, 2006). The patent application WO2004111194 by Ailor Eric claims the overexpression of XBP-1 or ATF6 for the generation of highly productive cell lines.

Notably, XBP-1 does not only regulate plasma cell differentiation but also plays an important role in the unfolded protein response (UPR) (Brewer and Hendershot, 2005). The UPR represents a complex signal transduction network activated by inhibition of protein folding in the endoplasmic reticulum (ER). The UPR coordinates adaptive responses to this stress situation, including induction of ER resident molecular chaperone and protein foldase expression to increase the protein folding capacity of the ER, induction of phospholipid synthesis, attenuation of general translation, and upregulation of ER-associated degradation to decrease the unfolded protein load of the ER. Upon severe or prolonged ER stress, the UPR ultimately induces apoptotic cell death (Schroder, 2006).

The process of terminal differentiation, such as the maturation from a lymphocyte to a plasma cell, is usually regarded an apoptosis-like program, during which the cell loses its proliferative capacity to give rise to a terminally differentiated secretory cell. In fact, nearly all cell types specifically designed for high-level protein secretion (e.g. glandular cells, pancreatic beta cells) are terminally differentiated, are not able to proliferate and have a limited life-span before ultimately undergoing programmed cell death (Chen-Kiang, 2003). Therefore, overexpressing XBP-1 as a regulator of both plasma cell differentiation and UPR, is potentially disadvantageous due to its inherent risk to inhibit proliferation and/or induce apoptosis.

Taken together, there is a need for improving the secretory capacity of host cells for recombinant protein production. This might even become more important in combination with novel transcription-enhancing technologies and in high-titer processes in order to prevent post-translational bottle necks and intracellular accumulation of the protein product (FIG. 1). However, at present, there are two major hurdles on the way to targeted manipulation of the secretory transport machinery: The still limited knowledge about the underlying regulatory mechanisms and the requirement to prevent a concomitant growth-inhibitory or apoptotic response of the producer cell.

The present invention describes a novel and surprising role for the ceramide transfer protein CERT in the transport of secreted proteins to the plasma membrane and furthermore provides a method to efficiently improve the production of proteins that are transported via the secretory pathway from eukaryotic cells.

CERT (also known as Goodpasture antigen-binding protein) is a cytosolic protein essential for the non-vesicular delivery of ceramide from its site of production at the endoplasmic reticulum (ER) to Golgi membranes, where conversion to sphingomyelin (SM) takes place (Hanada et al., 2003).

Two CERT isoforms exist: the more abundantly expressed, alternatively spliced form missing a 26-amino-acid, serine-rich region (SEQ ID NO. 10, 11) and the full-length 624 amino acid protein, designated $CERT_L$ (SEQ ID NO. 12, 13) (Raya et al., 2000). Both CERT isoforms possess a carboxy-terminal steroidogenic acute regulatory (StAR)-related lipid transfer (START) domain that is necessary and sufficient for ceramide binding and transport (Hanada et al., 2003). START domains are highly conserved from fly and worm to humans (FIG. 2). They are ~210 amino acids in length and form a hydrophobic tunnel that accommodates a monomeric lipid (Alpy and Tomasetto, 2005; Soccio and Breslow, 2003). START domains are found in 15 mammalian proteins, with CERT being most closely related to the phosphatidylcholine transfer protein Pctp, which binds and shuttles phosphatidylcholine (PC) between membranes, and StarD10, a lipid transfer protein specific for PC and PE (Olayioye et al., 2005; Soccio and Breslow, 2003; Wirtz, 2006). In addition to the START domain, the CERT proteins further contain an aminoterminal PH domain with specificity for PI(4)P that is responsible for Golgi localization (Hanada et al., 2003; Levine and Munro, 2002) and a FFAT (SEQ ID NO: 29) motif (two phenylalanines in an acidic tract) that targets the protein to the ER via interaction with the ER resident transmembrane proteins VAP-A and VAP-B (Kawano et al., 2006; Loewen et al., 2003).

The fundamental role of CERT in lipid trafficking was demonstrated in the Chinese hamster ovary cell line LY-A, in which the expression of a mutant non-functional CERT protein impaired ceramide transport, thus resulting in reduced cellular levels of sphingomyelin (Hanada et al., 2003). Non-vesicular lipid transfer is thought to occur at so-called membrane contact sites (MCS), at which the ER comes into close apposition with other organelles (Levine and Loewen, 2006). CERT may thus shuttle a very short distance between ER and Golgi membranes, or perhaps contact both compartments simultaneously. When overexpressed, the START domain of CERT is sufficient for ceramide transfer to the Golgi apparatus (Kawano et al., 2006). However, under physiological conditions, both Golgi and ER targeting motifs are essential for CERT function. In LY-A cells, CERT was identified to contain a mutation within its PH domain (G67E), rendering the protein defective in PI(4)P binding (Hanada et al., 2003). The requirement for PI(4)P for CERT function is further supported by a recent report that PI4KIII-beta activity is necessary for efficient ceramide trafficking to the Golgi (Toth et al., 2006), the enzymatic activity of which is stimulated by protein kinase D (PKD).

PKD belongs to a subfamily of serine-/threonine-specific protein kinases (comprising PKD1/PKCμ, PKD2 and PKD3/PKCυ) and was recently identified to be of crucial importance for the regulation of protein transport from the Golgi membrane to the plasma membrane (reviewed in (Rykx et al., 2003; Wang, 2006)). Recruitment and activation of PKD at the TGN is mediated by the lipid diacylglycerol (DAG; (Baron and Malhotra, 2002)), a pool of which is generated by sphingomyelin synthase from ceramide and phosphatidylcholine.

The present invention shows that PKD phosphorylates CERT on serine 132 adjacent to the PH domain, whereby PI(4)P binding, Golgi targeting and ceramide transfer activity are negatively regulated. Furthermore, by transferring ceramide that is required for DAG production to Golgi membranes, CERT stimulates PKD activity, thus establishing a regulatory feedback-loop that ensures the maintenance of constitutive secretory transport.

Importantly, the data provided furthermore show that in different eukaryotic cell lines (COS7 and HEK293), introduction of the gene encoding CERT significantly enhances the secretion of a heterologous protein into the culture medium. This effect is even more pronounced when using a CERT mutant which cannot be phosphorylated by PKD. Deletion of the phosphorylation acceptor site within CERT interrupts the negative control of PKD on CERT, but leaving the positive feedback of CERT on PKD intact through the support of ceramide conversion to sphingomyelin and DAG. It can therefore be speculated that the secretion enhancing mechanism of the present invention can be exerted not only by wild type CERT but also by all mutants of CERT which uncouple CERT from the negative influence of PKD, including point mutations of the acceptor serine, deletions including this residue as well as mutation or deletion of the PKD docking site within CERT or even the START domain alone.

CERT belongs to the family of StAR-related Lipid Transfer proteins (Soccio and Breslow, 2003), which are characterized by their START domains for lipid binding. As the START domain of CERT has been demonstrated to be both required and sufficient for CERT action (Hanada et al., 2003), it is possible that the secretion-promoting effect of CERT could equally be observed when overexpressing another member of this protein family. This is especially likely for the closely related members of the PCTP-subfamily, comprising PCTP (SEQ ID NO. 26, 27), CERT/GPBP itself, StarD7 and StarD10. These proteins have distinct lipid-binding specificities and could equally impact on the function of organelles involved in the secretion of heterologous proteins.

Furthermore, expression of the related proteins STARD4 (SEQ ID NO. 20, 21) and STARD5 (SEQ ID NO. 22, 23), that are induced upon ER stress, may function to fulfill the increased demand of lipid transfer of cells during a production process.

The existence of START domain proteins in eukaryotic organisms from fly, worm and mouse to humans indicates that the basic mechanisms of lipid trafficking are conserved among the eukaryotic kingdom. It furthermore suggests, that the principle described in the present invention—that is increasing secretion by enforced expression of CERT—may well be applicable to all eukaryotic cells, including yeast.

In summary, the present invention provides a method for enhancing the secretory transport of proteins in eukaryotic cells by heterologous expression of CERT, CERT mutants or another member of the START protein family. This method is particularly useful for the generation of optimized host cell systems with enhanced production capacity for the expression and manufacture of recombinant protein products.

The method described in the present invention is advantageous in several respects:

First, we demonstrate heterologous expression of CERT to be a strategy to enhance recombinant protein production by increasing the secretory capacity of the host cell. Enhancing the specific productivity of producer cells translates into higher product yields in industrial protein production processes. With the current trend towards high-titer processes and more sophisticated expression enhancing technologies, post-translational bottle necks will become the evident rate-limiting steps in protein production and hence will draw increasing attention to secretion engineering approaches.

Second, the START domain of CERT is highly conserved in eukaryotes from *C. elegans* to humans. This strongly suggests that the method of the present invention can not only be used in mammalian host cell systems, but is equally applicable for protein production in all eukaryotic cells, including insect cells and yeast cells.

As a third important feature, CERT as a cytosolic factor is not part of the unfolded protein response and thus is not involved in a cellular stress response program which induces the shut-down of protein translation and—if not resolved—leads to cell cycle arrest or even apoptosis. In contrast, by playing an independent role in lipid trafficking, targeting CERT might confer enhanced protein secretion without concomitant induction of apoptosis. Thus, overexpressing CERT in producer host cells might be advantageous over XBP-1 based genetically engineering approaches.

Fourth, it is shown in the present invention that mutation of Ser132 of CERT impairs the phosphorylation of CERT by PKD which frees CERT from a negative regulatory influence. Meanwhile, the positive stimulation of PKD by CERT via DAG is left intact (FIG. 3A). This finding places CERT in the signalling pathway "upstream" of PKD, which has been published to be critically involved in the regulation of the late stages of secretory transport, namely the transport from the trans-Golgi network to the plasma membrane (Liljedahl et al., 2001). With regard to protein transport, this means, that CERT acts "downstream" of the ER which makes CERT the preferable target for manipulation compared to XBP-1 or specific ER-residing proteins (FIG. 3B).

Since CERT can impact even on the latest steps of the secretory pathway, it can be speculated that heterologous expression of CERT has the potential to enhance secretion without creating bottle necks further downstream. To our knowledge, CERT is currently the most downstream acting target for genetical engineering of the secretory pathway to enhance heterologous protein production.

Taken together, the impact of the lipid-transfer protein CERT on the secretory transport from ER to Golgi and from the Golgi apparatus to the plasma membrane, without the disadvantageous connection to a growth-inhibiting or apoptosis-inducing stress response make CERT, CERT mutants and other START family proteins very attractive and promising targets for genetic engineering approaches aiming to enhance the secretory capacity of eukaryotic cells.

3. Applicability

The targeted manipulation of CERT which is described in the present invention can be used for a broad range of applications. In particular, two basic approaches can be distinguished:

(i) Overexpression and/or enhancing the activity of CERT or a CERT derivative to increase the secretory transport capacity of a cell, or (ii) reducing CERT activity and/or expression as a means of gene therapy in order to reduce cancer cell proliferation and/or invasion.

Applicability of CERT Overexpression

The described invention describes a method to generate improved eukaryotic host cells for the production of heterologous proteins by introducing the gene encoding CERT, CERT mutants or other proteins of the START protein family. This will enable to increase the protein yield in production processes based on eukaryotic cells. It will thereby reduce the cost of goods of such processes and at the same time reduce the number of batches that need to be produced to generate the material needed for research studies, diagnostics, clinical studies or market supply of a therapeutic protein. The invention will furthermore speed up drug development as often the generation of sufficient amounts of material for pre-clinical studies is a critical work package with regard to the timeline.

The invention can be used to increase the property of all eukaryotic cells used for the generation of one or several specific proteins for either diagnostic purposes, research purposes (target identification, lead identification, lead optimization) or manufacturing of therapeutic proteins either on the market or in clinical development.

As shown in the present invention, heterologous expression of CERT does not only enhance protein secretion, but also has an influence on the abundance of transmembrane proteins on the cell surface. Inhibition or reduced expression of CERT leads to a dramatic reduction of the amount of cell surface receptors such as the transferrin receptor (FIG. 8). As secreted and transmembrane proteins share the same secretory pathways and are equally transported in lipid-vesicles, these data underscore the importance of CERT in the modulation of secretion as well as the transport of membrane-bound cell-surface receptors.

Therefore, the method described herein can also be used for academic and industrial research purposes which aim to characterize the function of cell-surface receptors. E.g. it can be used for the production and subsequent purification, crystallization and/or analysis of surface proteins. This is of crucial importance for the development of new human drug therapies as cell-surface receptors are a predominant class of drug targets. Moreover, it might be advantageous for the study of intracellular signalling complexes associated with cell-surface receptors or the analysis of cell-cell-communication which is mediated in part by the interaction of soluble growth factors with their corresponding receptors on the same or another cell.

Applicability of Decreasing/Inhibiting CERT

In the present invention, we provide evidence that the reduction of CERT expression leads to reduced secretion of soluble extracellular proteins as well as a lower abundance of cell surface receptors. This makes CERT an attractive target for therapeutic manipulation.

One of the hallmarks in the conversion from a normal healthy cell to a cancer cell is the acquisition of independency from the presence of exogenous growth factors (Hanahan and Weinberg, 2000). In contrast to the normal cell, tumor cells are able to produce all growth factors necessary for their survival and proliferation by themselves. In addition to this autocrine mechanism, cancer cells often show an upregulated expression of growth factor receptors on their surface, which leads to an increased responsiveness towards paracrine-acting growth and survival factors secreted from cells in the surrounding tissue. By targeting CERT in tumor cells, e.g. by using siRNA approaches, it might be possible to disrupt autocrine as well as paracrine growth-stimulatory and/or survival mechanisms in two ways: (i) By reducing growth factor transport and secretion and (ii) by decreasing the amount of the corresponding growth factor-receptor on tumor cells. Thereby both, the amount of growth stimulating signal and the ability of the cancer cell to perceive and respond to these signals will be reduced. Inhibition of CERT expression in cancer cells might therefore represent a powerful tool to prevent cancer cell proliferation and survival.

CERT might furthermore be a potent therapeutic target to suppress tumor invasion and metastasis. During the later stages of most types of human cancer, primary tumors spawn pioneer cells that move out, invade adjacent tissues, and travel to distant sites where they may succeed in founding new colonies, known as metastasis.

As a prerequisite for tissue invasion, cancer cells express a whole set of proteases which enable them to migrate through the surrounding healthy tissue, to cross the basal membrane, to get into the blood stream and to finally invade the tissue of destination.

Some of these proteases are expressed as membrane-bound proteins, e.g. MT-MMPs (Egeblad and Werb, 2002) and ADAMs (Blobel, 2005). Due to their crucial role in matrix remodelling, shedding of growth factors and tumor invasion, proteases themselves are discussed as drug targets for cancer therapy (Overall and Kleifeld, 2006). We hypothesize that inhibition of CERT expression and/or activity in tumor cells will reduce the amount of membrane-bound proteases on the surface of the targeted cell. This might decrease or even impair the invasive capacity of the tumor cell as well as its ability for growth factor shedding, resulting in reduced invasiveness and metastatic potential of the tumor. Thus, targeting CERT might offer a novel way of preventing late-stage tumorgenesis, especially the conversion from a benign/solid nodule to an aggressive, metastasizing tumor.

For therapeutic applications it is, thus, the goal to reduce and/or inhibit the activity and/or expression of CERT. This can be achieved either by a nucleotide composition which is used as human therapeutic to treat a disease by inhibiting CERT function whereby the drug is composed of an RNAi, and siRNA or an antisense RNA specificly inhibiting CERT through binding a sequence motive of CERT RNA. Reduction/inhibition of CERT activity/expression can also be achieved by a drug substance containing nucleotides binding and silencing the promoter of the CERT gene.

Furthermore, a drug substance or product can be composed of a new chemical entity or peptide or protein inhibiting CERT expression or activity. In case of a protein being the active pharmaceutical compound it may be a (i) protein binding to CERT promoter thereby inhibiting CERT expression, (ii) protein binding to CERT or PKD thus preventing binding of PKD and CERT and hindering CERT phosphorylation by PKD, (iii) a protein similar to CERT which however does not fulfill CERT functions, that means a “dominant-negative” CERT variant, or (iv) a protein acting as scaffold for both CERT and PKD, resulting in irreversible binding of CERT to PKD (=a stable PKD/CERT complex) which is not functional due to the inhibitory phosphorylation of CERT by PKD and the hindering of dissociation of CERT from said complex.

SUMMARY OF THE INVENTION

The present invention is not obvious from the prior art. Up to this point the only experimental data available on the protein CERT pointed to a role in transport of ceramide from the endoplasmic reticulum to the Golgi apparatus as a precursor of sphingomyelin. Only the data described in this invention lead to a novel working model for a role of CERT in protein transport form the Golgi to the plasma membrane in eukaryotic cells. The prior art does not give any hint on the possibility of enhancing the rate of secretory transport of proteins in eukaryotic cell lines by introducing the gene encoding CERT or another member of the START domain protein family.

The surprising and unexpected working model of the present invention identifies CERT as a novel in vivo PKD substrate and crucial regulator of Golgi function.

PKD is known from the prior art. It is a family of serine/threonine-specific protein kinases comprising three structurally related members: PKD1/PKCμ, PKD2 and PKD3/PKCυ. PKD contains two aminoterminal zinc finger-like cysteine-rich motifs that bind DAG, a pleckstrin homology (PH) domain that negatively regulates PKD enzymatic function and a carboxyterminal kinase domain.

The three PKD isoforms localize to the cytosol, nucleus, Golgi complex and plasma membrane, where they regulate diverse cellular processes, ranging from proliferation, differentiation, apoptosis, cytoskeletal reorganization and metastasis to vesicle trafficking (reviewed in (Rykx et al., 2003; Wang, 2006)). Thus far, only a few physiological PKD substrates are known, which include the neuronal protein Kidins220, the Ras effector RINI, histone deacetylase 5, E-cadherin and PI4KIIIβ (Iglesias et al., 2000; Jaggi et al., 2005; Vega et al., 2004; Wang et al., 2002). At the TGN, PKD is critically involved in the fission of transport carriers en route to the cell surface (Liljedahl et al., 2001; Yeaman et al., 2004). PKD is recruited to the TGN by its cysteine-rich regions (Baron and Malhotra, 2002; Hausser et al., 2002; Maeda et al., 2001), where it is activated by PKCç-mediated phosphorylation (az Anel and Malhotra, 2005).

Recently PI4KIIIâ was identified, a key player in structure and function of the Golgi apparatus, as a PKD substrate at this organelle (Hausser et al., 2005). PKD-mediated phosphorylation of PI4KIIIâ at serine 294 stimulates its lipid kinase activity, resulting in enhanced phosphatidylinositol 4-phosphate (PI(4)P) production and vesicular stomatitis virus G-protein transport to the plasma membrane (Hausser et al., 2005).

Protein kinase D (PKD) has been identified as a crucial regulator of secretory transport at the trans-Golgi-network (TGN). Recruitment and activation of PKD at the TGN is mediated by the lipid diacylglycerol (DAG), a pool of which is generated by sphingomyelin synthase from ceramide and phosphatidylcholine. The non-vesicular transfer of ceramide from the endoplasmic reticulum to the Golgi complex is mediated by the lipid transfer protein CERT. This is described for example in Hanada et al, 2003, Nature Vol 426, 803-809 and Hanada 2006, Molecular and Cellular Biochemistry 286, 23-31 as well as in the corresponding patent applications WO2005004898 and EP1652530. In neither one of these documents, however, Hanada shows or points towards an implication of modulating CERT expression or activity (let alone other START domain proteins) in a method of producing proteins for diagnostic, research or therapeutic purposes. Furthermore, these documents/patent applications do not describe in any way the use of a blocking agent which reduces or completely blocks CERT expression or activity in a pharmaceutical composition. Hanada rather concludes to use CERT itself as a drug to promote ceramide transport.

The present invention, however, identifies CERT as a novel in vivo PKD substrate. Phosphorylation on serine 132 by PKD decreases the affinity of CERT towards its lipid target phosphatidylinositol 4-phosphate at Golgi membranes and reduces ceramide transfer activity, identifying PKD as a regulator of lipid homeostasis. The present invention also shows that CERT in turn is critical for PKD activation and PKD dependent protein cargo transport to the plasma membrane. The interdependence of PKD and CERT is thus a key to the maintenance of Golgi membrane integrity and secretory transport.

Figure 1:
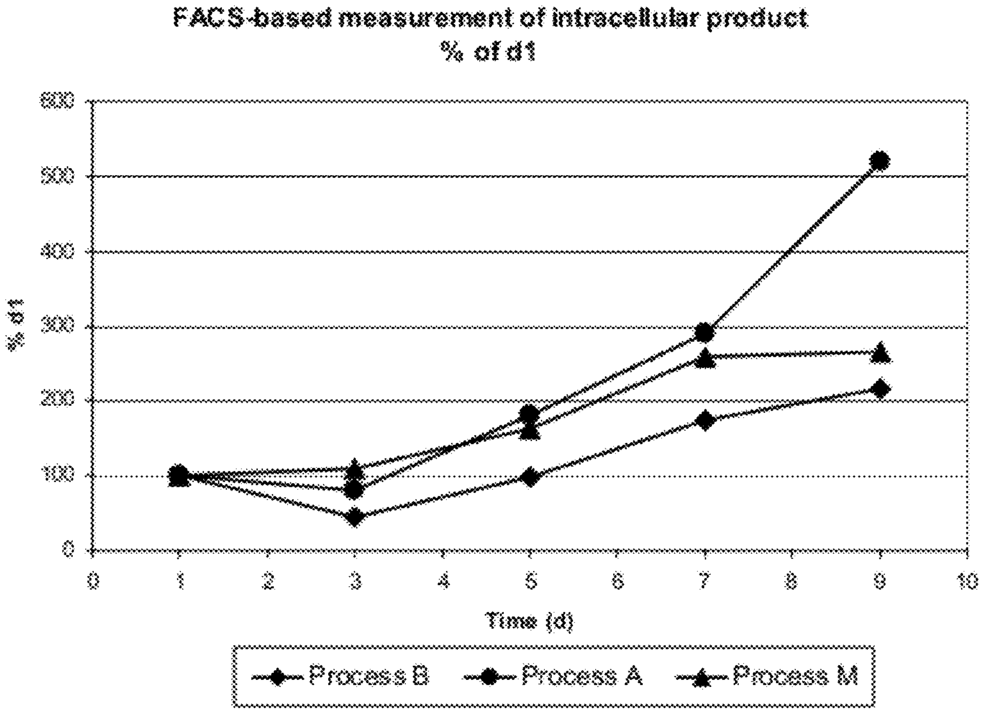
FIG. 1.
Figure 2:
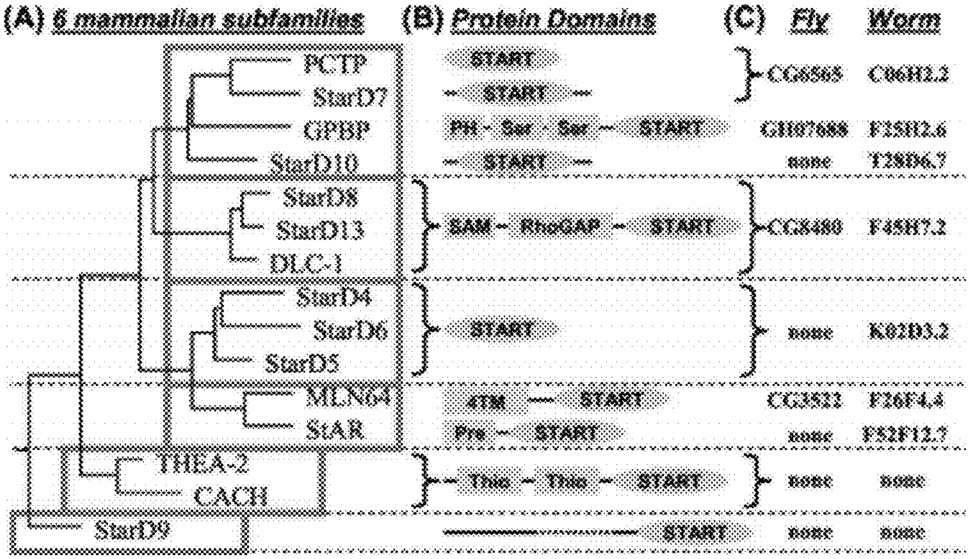

Intracellular Product Accumulation.

Increase of intracellular product during Fed-batch fermentations shown for three processes. Fed-batch fermentation was performed using three different CHO producer cell clones expressing human IgG antibodies: Process A (circles), B (diamonds) and M (triangles), respectively). Every other day, cell samples were taken, fixed and subjected to direct immunofluorescence to detect the antibody light-chain. The amount of product was measured by FACS and plotted relative to the amount at day 1.

FIG. 2:

The START Domain Protein Family

Phylogenetic assembly of (A) human START domain proteins, (B) their domain organization (4 TM, four transmembrane; Pre, mitochondrial presequence; Thio, acyl-CoA thioesterase), and (C) their homologs in fly and worm. (Taken from (Soccio and Breslow, 2003))

FIG. 3:

CERT is a crucial regulator of Golgi function and acts downstream of XBP-1 in the secretory pathway.

(A) CERT and PKD are connected in a regulatory feedback-loop. The scheme summarizes the current working hypothesis where PKD is activated by DAG and phosphorylates CERT. Phosphorylated CERT dissembles from PI(4)P and releases ceramide at the site of its destination. Ceramide at the Golgi is converted to sphingomyelin and DAG which in turn is necessary for PKD activation. This circuit can be interrupted by mutation of the CERT phosphorylation site (S132A).

(B) The schematic drawing shows the way of a secreted protein from transcription and translation through the ER and Golgi compartments to the plasma membrane where the protein is finally released from the cell into the medium. The arrows represent recent genetic engineering approaches aiming to enhance protein production. Most efforts focused on transcription enhancing technologies, few on translation engineering, and at present, only three examples have been reported which target proteins involved in post-translational processing within the ER (BiP, PDI and XBP-1). CERT acts downstream of the ER in the secretory pathway and thus to our knowledge represents the first target for engineering at later stages of the secretion process

FIG. 4:

CERT is Detected by a PKD Substrate Antibody.

(A) HEK293T cells were transfected with expression plasmids encoding Flag-tagged CERTL and CERT. Cells were lysed 24 h post transfection and CERT isoforms were immunoprecipitated with anti-Flag antibody. Immunoprecipitated proteins were subjected to SDS-PAGE, followed by immunoblotting with PKD substrate antibody (PMOTIF; top panel) and, after stripping, with anti-Flag antibody (bottom panel).

(B) HEK293T cells were transfected with Flag-CERT expression plasmid, along with GFP-PKD1 K612W (PKD-KD) or empty vector. CERT was analyzed by Western blotting as described in (A). Expression of PKD-KD was verified by immunoblotting with a PKD-specific antibody (C20; bottom panel).

(C) COS7 cells were cotransfected with Flag-CERT and PKD1-GFP expression plasmids, fixed and stained with Flag-specific antibody (red). The images shown are stacks of several confocal sections. Scale bar, 20 μm.

Figure 5:
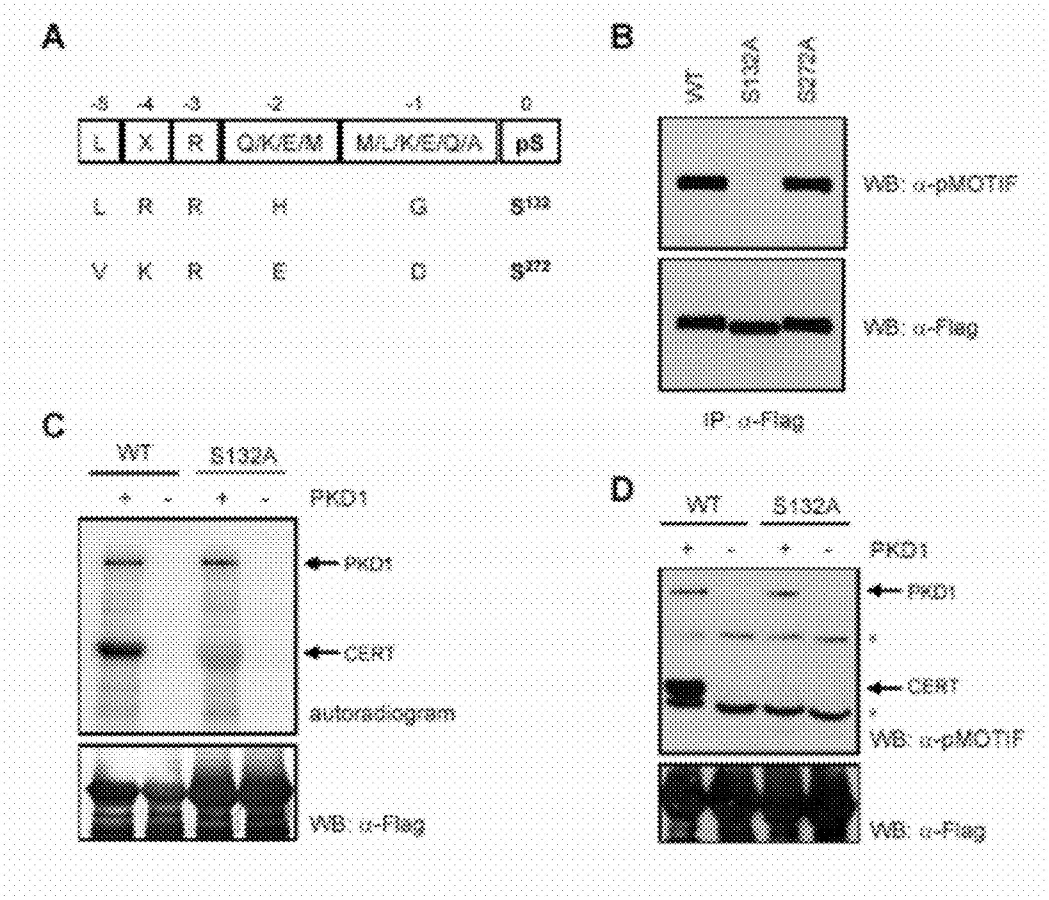

FIG. 5: PKD PHOSPHORYLATES CERT on SERINE 132.

(A) Alignment of the peptide sequences used to raise the PKD substrate antibody and two potential PKD motifs in CERT.

Figure 4:
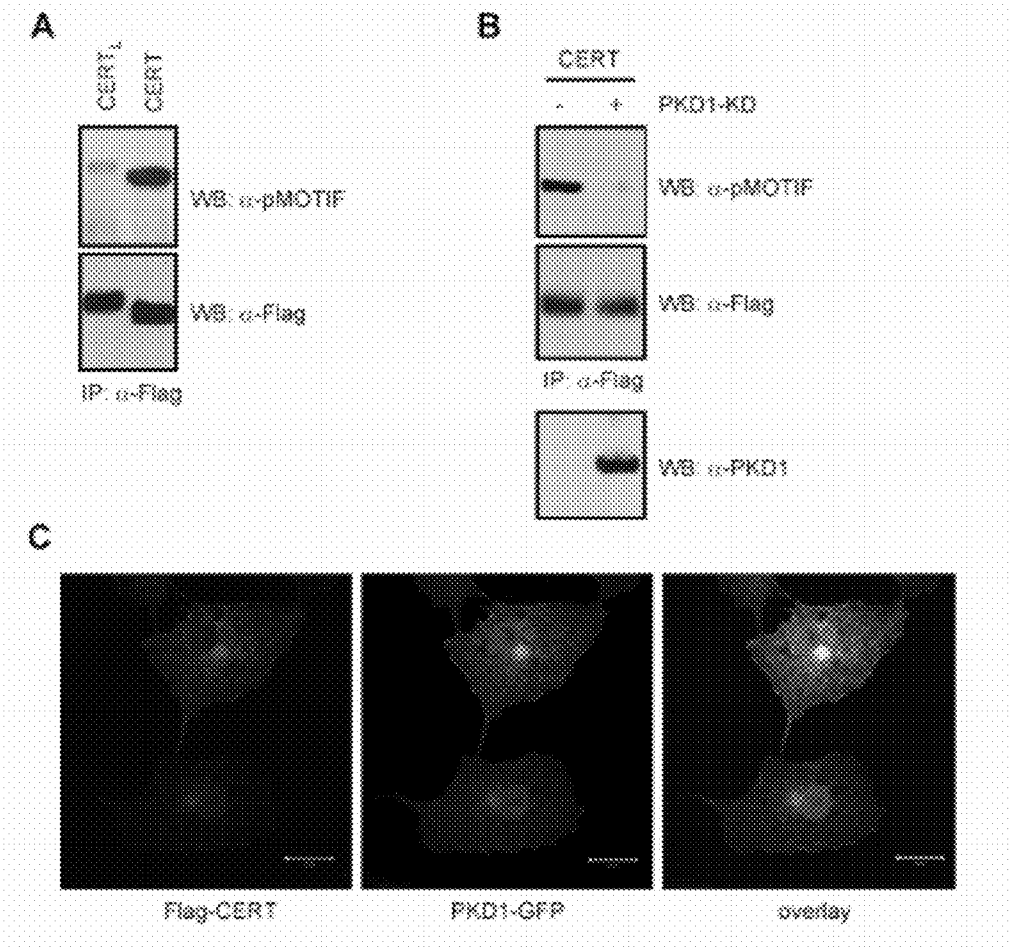

(B) HEK293T cells were transfected with expression plasmids encoding Flag-tagged CERT wild type (WT), CERT-S132A, and CERT-S272A. The cells were lysed and CERT proteins were immunoprecipitated and analyzed by Western blotting as described in FIG. 4.

(C) Recombinant GST-Flag-CERT wild type (WT) and S132A fusion proteins were incubated in kinase buffer containing [$^{32}$P]-ã-ATP in the absence (–) and presence (+) of purified PKD1 for 30 min. Proteins were separated by SDS-PAGE and transferred to membrane. Incorporation of radioactive phosphate was analyzed using a PhosphoImager (top), followed by immunoblotting with Flag-specific antibody to verify equal loading of the CERT proteins.

(D) Recombinant CERT proteins were subjected to an in vitro kinase with purified PKD1 as described in (C) in the presence of cold ATP. Immunoblotting was performed with the pMOTIF antibody and, after stripping, with Flag-specific antibody to verify equal loading of the CERT proteins. PKD1 and CERT proteins are marked with arrows; the bands with asterisks are due to non-specific binding.

FIG. 6:

CERT phosphorylation on serine 132 modulates PI(4)P binding and ceramide transfer activity.

HEK293T cells were transfected with expression plasmids encoding GFPtagged CERT wild type (WT, SEQ ID NO. 10, 12) and CERT-S132A (SEQ ID NO. 14). Cells were harvested by hypotonic lysis 24 h post transfection and the cytosol fraction was recovered after centrifugation at 100,000×g.

Samples containing equal amounts of GFP fluorescence were used for (A) Protein-lipid overlay assays. Cytosol from HEK293T cells transiently expressing the CERT variants was incubated with membranes spotted with a concentration gradient of the different phosphoinositides and bound CERT proteins were detected via their GFP tag.

(B) Donor liposomes containing TNPPE and pyrene-ceramide were mixed with a 10-fold excess of unlabeled acceptor liposomes. After 60 sec, cytosol from cells transiently expressing GFP-tagged CERT wild type (WT), S132A, or GFP alone (con) was added and pyrene fluorescence at 395 nm was recorded (excitation: 340 nm). Spectra were normalized to maximum fluorescence in Triton X-100 and to maximum GFP fluorescence.

FIG. 7

CERT Regulates PKD Activation and Secretory Transport.

(A) Western Blot of whole cell lysates from HEK293T cells transfected with either Flag-tagged CERT wild type (SEQ ID NO. 10, 12) or the CERT mutant S132A (SEQ ID NO. 14). The blot was probed with phosphospecific pS916 PKD antibody (top panel), a PKD-specific antibody (middle panel) and a Flag-specific antibody (bottom panel), respectively, to verify expression of the Flag-tagged CERT constructs.

(B) Measurement of HRP-activity in the supernatants of HEK293T cells cotransfected with Flag-ss-HRP and empty vector (black bars), PKD1-GFP kinase dead (KD, white bars), Flag-CERT wild type (WT, shaded bars) or Flag-CERT-S132A (dark grey). Relative light units (RLU) were plotted at the indicated time points after medium change. The values correspond to the mean of triplicate samples, error bars=SEM.

(C) Confocal immunofluorescence of GFP-CERT (green) and the cis/medial-Golgi marker GS28 (red) in COS7 cells. The images shown are stacks of several confocal sections. Scale bar, 20 μm.

(D) Stacks of confocal images showing the co-localization of GFP-CERT (green) and HRP-Flag (red) in COS7 cells. Scale bar, 20 μm and 5 μm (enlargement).

FIG. 8:

CERT Downregulation by RNA Interference Inhibits Secretory Transport.

(A) Quantitative detection of HRP activity in the supernatants of COS7 cells treated with either mock—(white), lacZ—(light grey=lacZ-specific siRNA SEQ ID No 9) or CERT-specific siRNA oligonucleotides (dark grey=siCERT#1 SEQ ID No 7 and black=siCERT#2 SEQ ID No. 8). The relative light units (RLU) of triplicate experiments are shown, error bars=SEM.

(B) Western Blot of the cell lysates of (A) probed with an anti-transferrin receptor antibody. Equal loading was confirmed by using an anti-Tubulin-specific antibody.

FIG. 9:

Consensus Terms for the START Domain

The consensus is given in relation to the number of proteins, which fit to this consensus sequence and not in relation to the number of amino acids which fit. That means that for the 80% consensus sequence 80% of the START domain proteins compared have the given amino acid at a particular position, e.g. a hydrophobic amino acid abbreviated with "h".

This consensus sequence was generated by using the WEB-based programm "SMART" (see also Ponting & Aravind, 1999, TIBS 24, pages 130-132).

(A) 80% consensus sequence (SEQ ID NO 28) for START domain proteins.

(B) The START domain consensus sequence (SEQ ID NO: 30) has been derived from an amino acid alignment of START domain proteins. The alignment includes 50%, 65% and 80% consensus sequences.

See the following amino acid grouping for help on abbreviation and the corresponding classes.

Class Key Residues

| | |
|---|---|
| alcohol o | S, T |
| aliphatic I | I, L, V |
| any . | A, C, D, E, F, G, H, I, K, L, M, N, P, Q, R, S, T, V, W, Y |
| aromatic a | F, H, W, Y |
| charged c | D, E, H, K, R |
| hydrophobic h | A, C, F, G, H, I, K, L, M, R, T, V, W, Y |
| negative – | D, E |
| polar p | C, D, E, H, K, N, Q, R, S, T |
| positive + | H, K, R |
| small s | A, C, D, G, N, P, S, T, V |
| tiny u | A, G, S |
| turnlike t | A, C, D, E, G, H, K, N, Q, R, S, T |

FIG. 10:

Introduction of CERT Increases Monoclonal Antibody Production

Expression constructs for Mock, CERT-WT or the mutant CERT-SA were stably introduced into a CHO production cell line secreting a human monoclonal IgG-type antibody. The effect of the transgenes on the specific IgG productivity in these stable clones was than measured (A) in serial stock cultures and (B) under fed-batch production conditions as in FIG. 11 with n=3-4 for each genotype. Error bars indicate standard deviations. One representative result out of three independent experiments is shown.

FIG. 11:

Heterologous CERT Increases HSA Secretion (A) Increased titer and specific productivity in serial cultures. CHO cells secreting human serum albumine (HSA) were stably transfected with either an empty plasmid ("Mock") CERT wild type (CERT-WT) or the CERT mutant S132A (CERT-SA). From the resulting stable cell pools (n=3 per genotype), the titer of HSA was determined during 3-5 serial passages. The specific productivity for HSA (black bars) and the titer (grey bars) were calculated for each genotype and plottet as mean values of the three pools. Error bars represent standard deviations.

(B) and (C) The cells from (A) were grown in shake-flasks for 7 days and feeded every 24 hours from day 3 on. Samples from the cell culture fluid were taken at day 3, 5 and 7 and subjected to titer measurement of the recombinant HSA product. Specific productivities (B) and titer (C) were calculated and plottet over the time of fermentation. The following cells were compared: Mock (-□-), CERT-WT (-▲-) and CERT-SA cells (-●-); error bars represent the standard deviations from three stable pools per genotype.

DETAILED DESCRIPTION OF THE INVENTION

Post-translational modification of proteins by phosphorylation is a common mechanism to induce conformational changes that modulate enzymatic activity, mediate protein-protein interactions or regulate subcellular localization. PKD is a key regulator at the Golgi complex with PI4KIIIβ being the only local substrate identified thus far. To test whether the Golgi complex-localized CERT protein may serve as a substrate for PKD, we made use of a phosphospecific substrate antibody, termed pMOTIF, raised against consensus motifs phosphorylated by PKD (Doppler et al., 2005). HEK293T cells were transfected with expression vectors encoding Flag-tagged CERT and $CERT_L$. The CERT isoforms were immunoprecipitated with Flag-specific antibodies and analyzed by Western blotting with the pMOTIF antibody (FIG. 4A). A pMOTIF signal corresponding to the molecular weight of CERT and, more weakly, to that of $CERT_L$ was detected (FIG. 4A). The weaker detection of the phosphorylated $CERT_L$ isoform may be related to its known behaviour to form aggregates, which may impact phosphosite accessibility to kinases (Raya et al., 2000). To investigate whether recognition of CERT by the pMOTIF antibody was dependent upon PKD, we expressed CERT together with a kinase dead variant of PKD1 (K621W) in HEK293T cells. This mutant has been shown to localize to the Golgi complex and suppressed PI4KIIIβ phosphorylation in a dominant negative fashion (Hausser et al., 2005). Coexpression of inactive PKD abolished detection of CERT with the pMOTIF antibody, suggesting that the pMOTIF signal was indeed due to PKD-mediated CERT phosphorylation (FIG. 4B). Lipid transfer proteins are thought to act at MCS, which are formed between the ER and TGN (Levine and Loewen, 2006), where PKD is localized. Immunofluorescence staining of Flag-tagged CERT in COS7 cells coexpressed with GFP-tagged PKD1 verified that the two proteins colocalize at the Golgi complex (FIG. 4C). RNA interference experiments suggest that simultaneous knockdown of PKD1 and PKD2 was required to reduce CERT phosphorylation, indicating that these two isoforms were primarily responsible for phosphorylating CERT, whereas PKD3 appeared to play a minor role (data not shown). This is in accordance with previously reported overlapping substrate specificities of PKD1 and PKD2. For example, PKD1 and PKD2 were both shown to phosphorylate PI4KIIIβ, whereas PKD3 failed to do so (Hausser et al., 2005).

To identify pMOTIF recognition sites in CERT, we searched for potential PKD consensus motifs characterized by a leucine, isoleucine or valine residue in the −5 and arginine in the −3 position relative to a serine or threonine. Two serines at positions 132 and 272, matching the PKD consensus motif and conserved across species (FIG. 5A), were exchanged for alanines by site-directed mutagenesis. These mutants were expressed in HEK293T cells and tested for recognition by the pMOTIF antibody. Interestingly, mutation of serine 132 to alanine abrogated detection of CERT with the pMOTIF antibody and caused an increase in electrophoretic mobility, indicative of loss of phosphorylation, while the S272A mutation did not affect the pMOTIF signal (FIG. 5B). This suggested that serine 132 is a PKD phosphorylation site specifically recognized by the PKD substrate antibody. To confirm that PKD was capable of directly phosphorylating this serine residue in CERT, we performed in vitro kinase assays with purified PKD1 and recombinant CERT GST-fusion proteins produced in *E. coli* comprising the first 138 amino acids of the protein. When the truncated wild type CERT fusion protein was incubated with PKD1 in the presence of [γ-$^{32}$P]-ATP, incorporation of radioactivity was detected (FIG. 5C). This was significantly impaired in the case of the CERT-S132A fusion protein. In vitro PKD phosphorylation of wild type but not CERT-S132A is further shown to generate a recognition site for the pMOTIF antibody (FIG. 5D). Taken together, these results prove that CERT is a genuine PKD substrate in vitro and in vivo and identify serine 132 as a specific PKD phosphorylation site in CERT.

Figure 6:
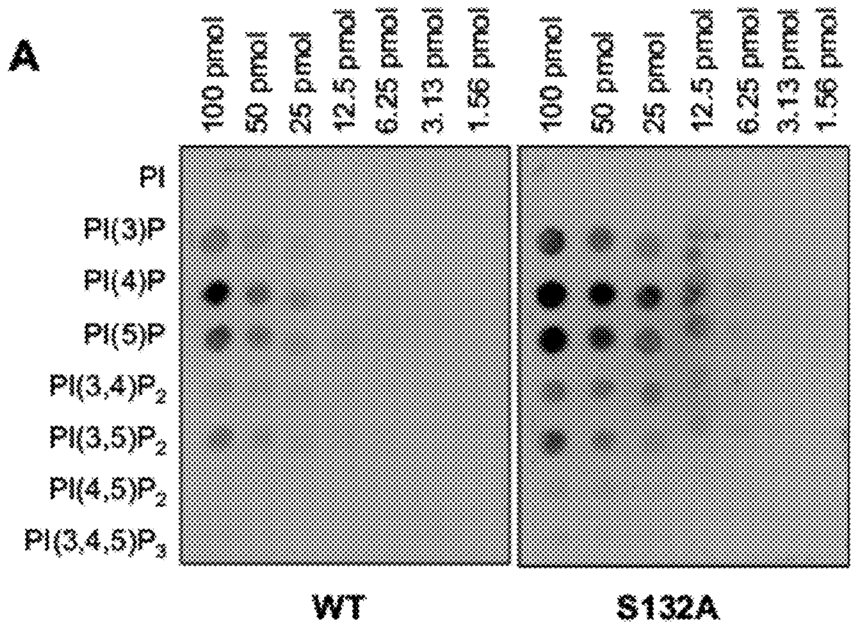
Figure 6:
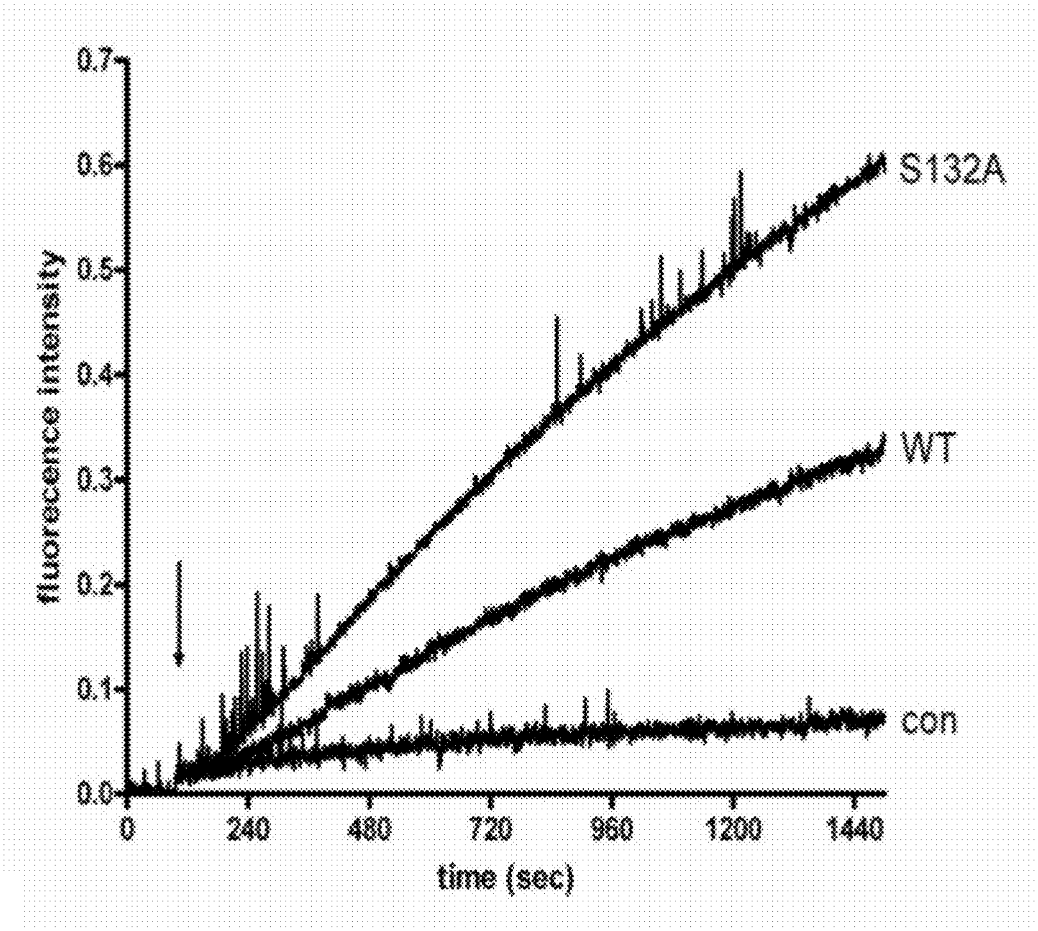

Serine 132 is in very close proximity to the CERT PH domain (amino acids 23-117), making it possible that phosphorylation on this site affects PI(4)P binding by increasing the local negative charge. We therefore quantified PI(4)P binding of wild type CERT and the CERT-S132A mutant by performing protein-lipid overlay assays. Here, cytosol from HEK293T cells transiently expressing the CERT variants was incubated with membranes spotted with a concentration gradient of the different phosphoinositides and bound CERT proteins were detected via their GFP tag. As reported previously, the full-length wild type protein demonstrated weak binding to several phospholipid species, but displayed strong interaction with PI(4)P (Hanada et al., 2003; Levine and Munro, 2002). CERT-S132A binding to PI(4)P was detectable at two- to fourfold lower concentrations as compared to that of the wild type protein, suggesting increased affinity of the CERT-S132A mutant to this phospholipid (FIG. 6A). Together, these data imply that CERT, once bound to the Golgi complex, is phosphorylated by PKD. This then decreases the affinity of CERT to PI(4)P and thereby regulates the interaction of CERT with Golgi membranes.

The CERT protein has been shown to function as a lipid transfer protein (Hanada et al., 2003). We thus investigated whether CERT phosphorylation on serine 132 influenced its ability to bind and transfer ceramide between membranes. To this end, GFP-tagged versions of wild type CERT and CERT-S132A were transiently expressed in HEK239T cells and the cytosol fraction was analyzed for ceramide-specific lipid transfer activity using a FRET-based assay (FIG. 6B). In this assay, small unilamellar vesicles containing pyrene-labeled ceramide as a fluorescent donor and quenching amounts of head group-labeled TNP-PE were employed (Olayioye et al., 2005; Somerharju, 2002). When these donor liposomes were mixed with an excess of unlabeled acceptor liposomes, the increase in pyrene fluorescence was negligible, indicating minimal spontaneous ceramide transfer to acceptor membranes (data not shown). Upon addition of wild type CERT-containing cytosol, a steady increase in fluorescence was noted, which was not observed when control cytosol of vector-transfected cells was used (FIG. 6B). Compared to the wild type protein, CERT-S132A displayed a higher rate of lipid transfer, evident from a more rapid increase in pyrene fluorescence (FIG. 6B). This suggests that CERT phosphorylation on serine 132 downregulates ceramide transfer activity by decreasing association of the protein with membranes. Previous data have already shown that PKD regulates the level of PI(4)P at the Golgi complex by phosphorylation-mediated activation of PI4KIIIβ (Hausser et al., 2005). Interestingly, PI4KIIIβ is critical for the transport of ceramide between the ER and the Golgi complex (Toth et al., 2006). Accordingly, together with the data presented here, a dual role for PKD in maintaining lipid homeostasis of Golgi membranes becomes apparent by controlling the on-rate (via PI(4)P levels) and the off-rate (via direct phosphorylation) of CERT.

Figure 7:
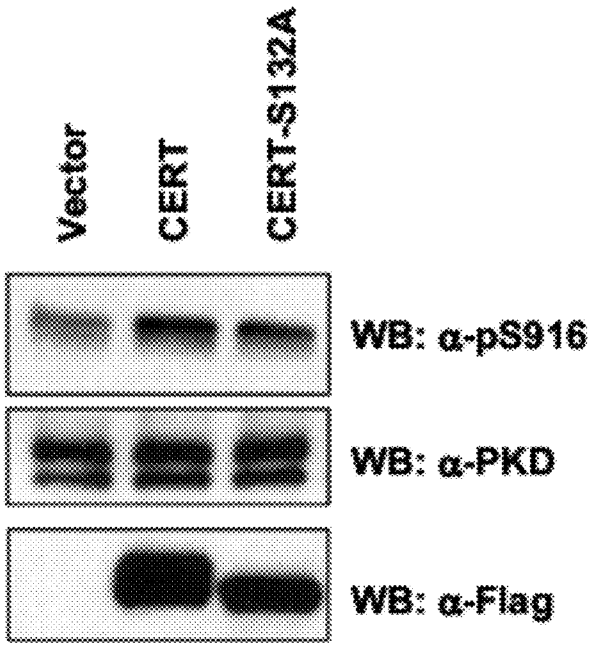
Figure 7:
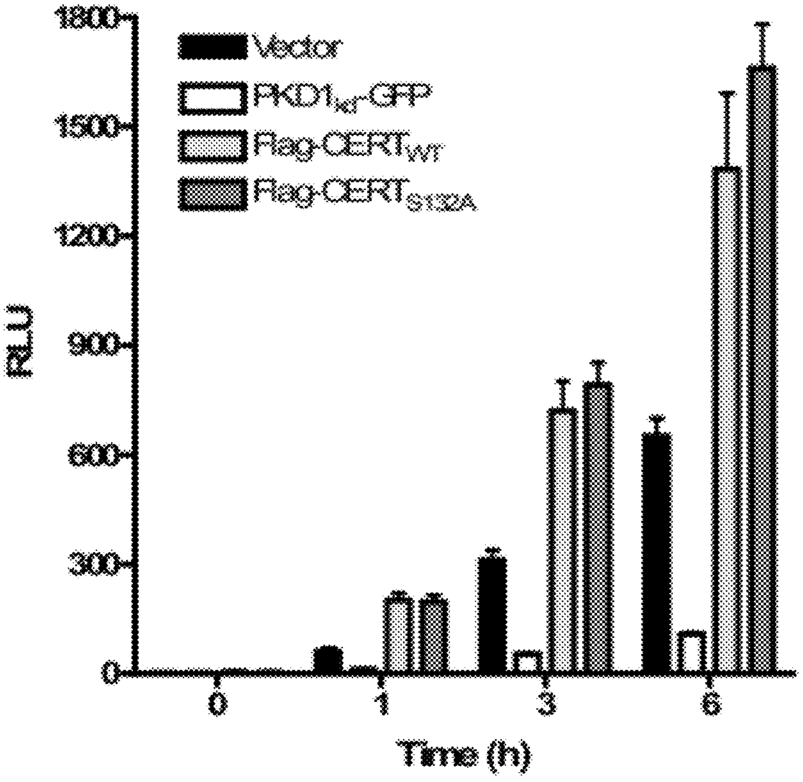
Figure 7:
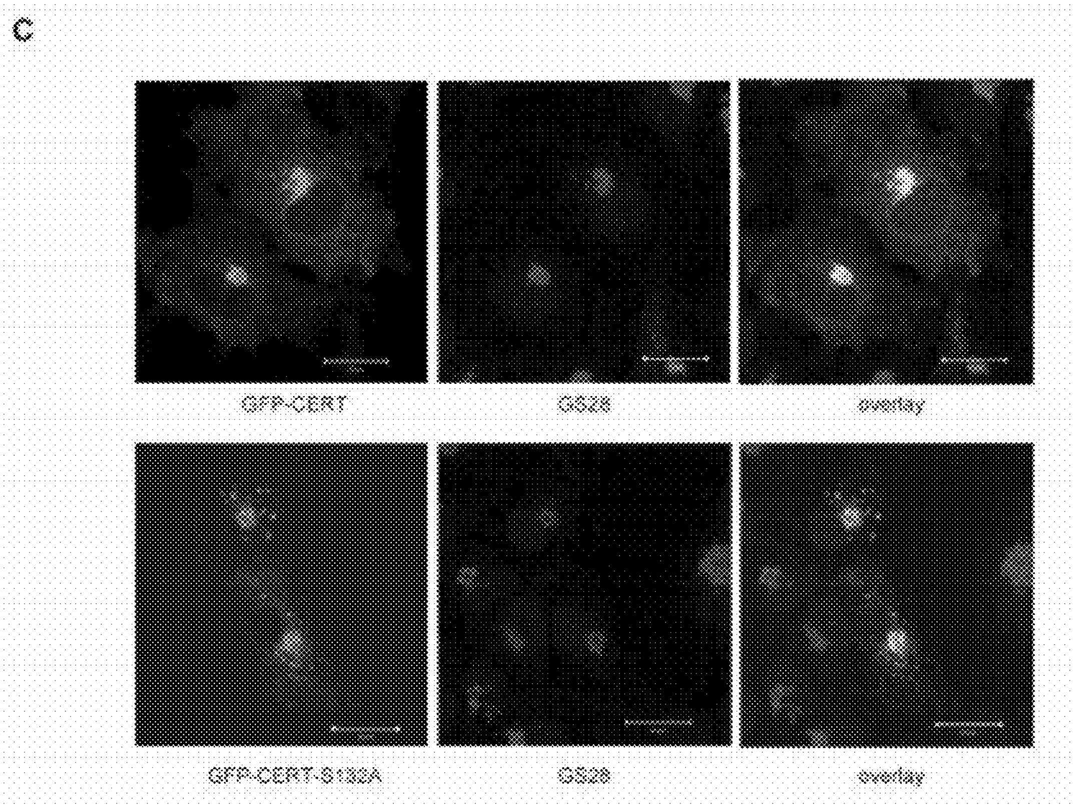
Figure 7:
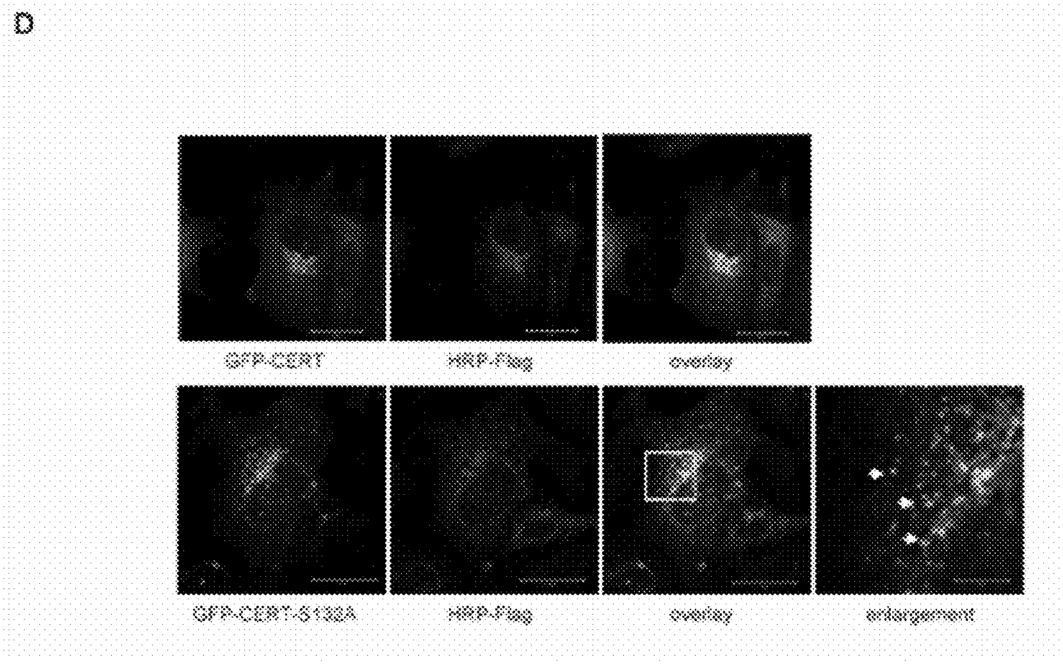

The transfer of ceramide from the ER to the TGN is essential for SM synthesis at this compartment (Hanada et al., 2003). Golgi-localized SM synthase 1 (SMS1) utilizes ceramide and PC to generate SM and DAG (Perry and Ridgway, 2005), the latter being a prerequisite for PKD recruitment and activation (Baron and Malhotra, 2002). Compounds that block DAG production at the TGN inhibit the binding of PKD to TGN membranes and interfere with secretory transport (Baron and Malhotra, 2002). Therefore, increased ceramide transfer from the ER to the TGN by overexpression of CERT should result in an elevated local DAG pool and may consequently stimulate PKD activity and secretory transport. To test this hypothesis, we transiently expressed CERT wild type and CERT-S132A in HEK293T cells and analyzed autophosphorylation of endogenous PKD. Compared to the control, expression of both CERT wild type and CERT-S132A increased PKD activity, as revealed by analyses with a phosphospecific PKD antibody (FIG. 7A). This shows that PKD activation is regulated by CERT proteins, likely due to increased ceramide delivery and enforced SM/DAG synthesis. A similar function has recently been described for the lipid transfer protein Nir2 in the maintenance of DAG levels at the Golgi apparatus via regulation of the CDP-choline pathway (Litvak et al., 2005). RNAi-mediated knock-down of Nir2 decreased the levels of DAG and PKD at the Golgi complex and blocked secretory transport. Interestingly, this effect could be rescued by the addition of exogenous $C_6$-ceramide (Litvak et al., 2005), indicating a critical role for ceramide in DAG synthesis and PKD recruitment to the Golgi complex.

To address the question of whether CERT-mediated PKD activation indeed translated into enhanced secretory transport, we made use of a plasmid encoding horseradish peroxidase fused to a signal sequence (ss). The fusion protein ss-HRP can be used as a reporter for constitutive protein secretion (Bard et al., 2006). In control cells, secretion of ss-HRP could be detected within 1 hour and increased over time (FIG. 7B). Coexpression of kinase dead PKD1, which inhibits secretory transport of cargo protein (Hausser et al., 2005; Liljedahl et al., 2001), almost entirely abrogated the secretion of ss-HRP into the supernatant. This confirmed that HRP was secreted in a PKD-dependent manner in our assay. Coexpression of CERT wild type and CERT-S132A strongly augmented the amount of secreted HRP (FIG. 7B). Interestingly, we could only detect a slight increase in secretion with the CERT-S132A mutant compared to the one observed with the CERT wild type protein. This is in accordance with the comparable activation of PKD by CERT and CERT-S132A (FIG. 7A), but was unexpected in the light of the significantly enhanced in vitro lipid transfer activity of the CERT mutant (FIG. 6B). However, increased levels of ceramide may not necessarily translate into equivalent increases in DAG, because DAG synthesis might be limited by the availability of PC and the activity of SM synthase. Accumulation of ceramide is known to affect Golgi membrane stability and induces vesicle fission (Fukunaga et al., 2000; Weigert et al., 1999). We therefore investigated whether overexpression of the CERT-S132A mutant affected its localization and/or caused morphological changes of the Golgi apparatus. CERT has been demonstrated to colocalize with the cis/medial-Golgi marker GS28 (Hanada et al., 2003). Immunofluorescence analysis of GFP-tagged CERT expressed in COS7 cells showed that the protein localized to GS28-positive Golgi regions (FIG. 7C). By contrast, in addition to the partial colocalization with GS28 at the Golgi complex, the CERT-S132A mutant protein displayed a dispersed, punctate staining. Of note, some of these vesicular structures were found to contain the cargo protein ss-HRP, providing evidence that these structures indeed represent Golgi-derived transport carriers (FIG. 7D). This finding is in accordance with the observed changes in Golgi membrane structure due to local increases in ceramide levels (Fukunaga et al., 2000; Weigert et al., 1999).

In conclusion, we have identified CERT as a PKD substrate and provide evidence for a novel relationship between membrane lipid biogenesis and protein secretion. We show that CERT plays an important role in vesicular transport processes by providing ceramide as a substrate for the synthesis of the PKD activator DAG at Golgi membranes. We further demonstrate that the system is tightly regulated by a negative feedback loop: Active PKD phosphorylates CERT at serine 132, thus decreasing the affinity of CERT towards its lipid target PI(4)P to ensure continuous rounds of lipid transfer from the ER to the Golgi compartment.

The data of the present invention clearly demonstrate that overexpression of CERT enhances protein secretion. To investigate whether also the opposite is true, meaning that reduced CERT expression would result in diminished secretion, siRNA experiments were performed. The activity of HRP was detected after 3 hours and showed equal comparable levels in both control cells. In contrast, a dramatic reduction of HRP activity was measured in cells that had been treated with any of the CERT-specific siRNA oligonucleotides (FIG. 8). This indicates that reduced CERT levels lead to reduced HRP secretion from the cells and further underscores the important role of CERT in the secretory transport.

Interestingly, not only protein secretion, but also the abundance of the transmembrane protein transferrin receptor was affected by the reduction of CERT (FIG. 8B). When the cells from FIG. 8A were pooled and the lysates probed with transferrin receptor-specific antibodies in Western blot experiments, a strong decrease in the amount of transferrin receptor became apparent, whereas similar transferrin receptor levels were detected in both control cells.

This finding suggests, that the lipid transfer protein CERT is not only implicated in the transport of secreted but also of membrane-standing cell-surface proteins. This might not be surprising as both types of proteins are equally transported in lipid vesicles from the ER via the Golgi to the plasma membrane and thus use the same cellular export routes which—as we demonstrate in the present invention for the first time—are influenced by CERT.

The findings and the resulting new model for regulation of secretory protein transport from the Golgi complex to the plasma membrane described in the present invention can be applied to biopharmaceutical protein manufacturing. Overexpression of CERT increases biopharmaceutical protein production of diverse proteins such as antibodies, cytokines, growth factors such as erythropoietin or insulin, surface receptors such as epithelial growth factor, and membrane-bound proteases.

Although the method described in this invention can be generally applied, to all protein production processes, the degree of success of this strategy as measured by the increase in the amount of protein produced can certainly depend on the particular nature of the protein of interest. CHO or other producer cells are transfected with an expression construct encoding a START domain protein such as CERT, StarD4 or StarD5 or a mutant or derivative thereof.

Notably, the highest titers are detected in cells expressing unphosphorylatable CERT mutant S132A. Heterologous expression of CERT, and especially mutant CERT, in CHO cells can enhance protein secretion, for example of a monoclonal antibody, on the transient transfection level. This can be particularly useful for fast production of smaller quantities of drug candidates or drug targets necessary in pharmaceutical research and development. In a further embodiment of this invention, a producer cell line is transfected with the same DNA constructs as above and subsequently subjected to selection to obtain stable cell pools. For six cell culture passages subsequent to the selection procedure, culture supernatant is collected to be analysed for the content of protein of interest. In case of a monoclonal antibody, the concentration of the protein product is determined by ELISA and divided by the mean number of cells to calculate the specific productivity. Again, the highest values are seen in the cell pools harbouring the CERT mutant. In cells containing a START domain construct expression of the protein of interest is significantly enhanced compared to MOCK or untransfected cells. Very similar results can be obtained if the stable transfectants are subjected to batch or fed-batch fermentations. In each of these settings, overexpression of START domain proteins leads to enhanced expression of antibodies, single cell proteins and surface receptors in transiently as well as stably transfected CHO cell lines, indicating that START domain proteins such as CERT or StarD4 and StarD5 are able to enhance the specific production capacity of the cells under fermentation conditions.

Definitions

The general embodiments "comprising" or "comprised" encompass the more specific embodiment "consisting of". Furthermore, singular and plural forms are not used in a limiting way.

Terms used in the course of this present invention have the following meaning.

The term "START domain" stands for steroidogenic acute regulatory protein (STAR) related lipid transfer (START) domain. This domain of about 200-210 amino acids was identified initially as lipid binding domain (Soccio and Breslow, 2003; Tsujishita and Hurley, 2000). The length of the START domain may vary between 116 to 250 amino acids, or between 180 to 223 amino acids, or more specifically between 219 to 223 amino acids depending on the START domain family member. The most striking feature of the START domain structure is a predominantly hydrophobic tunnel extending nearly the entire length of the protein which is used to binding a single molecule of large lipophilic compounds, like cholesterol. The structural resolution of the START domain family member MLN64-START revealed an α/β type structure consisting of nine-stranded twisted anti-parallel β-sheets and four α-helices (Tsujishita and Hurley, 2000). The domain found in various eukaryotic proteins is referred to as 'classical START domain' (CSD) while a similar domain specific to plants is known as Birch allergen START domain (BA-START).

The term "CERT" encompasses both splice forms of CERT: CERT (SEQ ID NO. 11) and $CERT_L$ (SEQ ID No. 13). The term "CERT" furthermore encompasses any other possible splice form of CERT derived from the nucleotide sequence SEQ ID No. 12.

The term "CERT" further encompasses hCERT protein and its recombinants, hCERT, hCERTA, PH protein, hCERT A MR protein, and hCERTA STprotein, and further, PHhCERT protein, MRhCERT protein and SThCERT protein (see also EP1652530, (Hanada, 2006), (Hanada et al., 2003)).

The term "derivative" in general includes sequences suitable for realizing the intended use of the present invention, which means that the sequences mediate the increase in secretory transport in a cell.

The term "derivative" as used in the present invention means a polypeptide molecule or a nucleic acid molecule which is at least 70% identical in sequence with the original sequence or its complementary sequence. Preferably, the polypeptide molecule or nucleic acid molecule is at least 80% identical in sequence with the original sequence or its complementary sequence. More preferably, the polypeptide molecule or nucleic acid molecule is at least 90% identical in sequence with the original sequence or its complementary sequence. Most preferred is a polypeptide molecule or a nucleic acid molecule which is at least 95% identical in sequence with the original sequence or its complementary sequence and displays the same or a similar effect on secretion as the original sequence.

Sequence differences may be based on differences in homologous sequences from different organisms. They might also be based on targeted modification of sequences by substitution, insertion or deletion of one or more nucleotides or amino acids, preferably 1, 2, 3, 4, 5, 7, 8, 9 or 10. Deletion, insertion or substitution mutants may be generated using site specific mutagenesis and/or PCR-based mutagenesis techniques. Corresponding methods are described by (Lottspeich and Zorbas, 1998) in Chapter 36.1 with additional references.

The sequence identity of a reference sequence (in the present invention being for example START domain SEQ ID No. 16, 17 or 18, 19) can be determined by using for example standard "alignment" algorithms, e.g. "BLAST" ((Altschul et al., 1990); (Madden et al., 1996); (Zhang and Madden, 1997)). Sequences are aligned when they fit together in their sequence and are identifiable with the help of standard "alignment" algorithms.

Furthermore, in the present invention the term "derivative" means a nucleic acid molecule (single or double strand) which hybridizes to SEQ ID No. 10, 12, 14, 16, 18, 20, 22, 24, 26) or with fragments or derivates thereof or with sequences which are complementary to SEQ ID No. 10, 12, 14, 16, 18, 20, 22, 24, 26. Preferably the hybridization is performed under stringent hybridization- and washing conditions (e.g. hybridisation at 65° C. in a buffer containing 5×SSC; washing at 42° C. using 0.2×SSC/0.1% SDS). Corresponding techniques are described exemplary in (Ausubel et al., 2002).

The term "derivatives" further means protein deletion mutants, phosphorylation mutants especially at a serine, threonine or tyrosine position, the deletion of a PKD binding site or the CERT Ser132A mutation.

The term "activity" describes and quantifies the biological functions of the protein within the cell or in in vitro assays An example of how to measure "activity" is described in the patent application EP1652530 (Hanada et al.), which detects ceramide release promotion activity from membranes. The lipid membrane containing ceramide has to be prepared so that it contains 12.5 nCi (225 pmol) per sample of [palmitoyl-1-I4C]N-palmitoyl-D-ethyro-sphigosine (hereinafter, may be referred to as I4C-ceramide) on the basis of a mixed lipid consisting of phosphatidylcholine and phosphatidylethanolamine at the ratio of 4:1 derived from egg yolk. Its concentration of ceramide thus is 2.5 mg/mL. For one sample of the activity measurement this lipid membrane is required at an amount of 20 pL. After the amount of lipid required for activity measurement has been dispensed in an Eppendorf tube, it has to be dried by spraying nitrogen gas. After this, the buffer 1 [20 mM Hepes-NaOH buffer (pH7.4) to which 50 mM NaCl and 1 mM EDTA have been added] has to be added to the dried lipid membrane, so that the concentration becomes 2.5 mg/mL. A gently supersonic treatment has to be performed using bath type supersonic generator [Model 221 0 manufactured by Branson, Co., Ltd.]. The supersonic treatment has to be performed at 25° C. for 3 minutes. The sample then has to be mixed (vortex) for 30 seconds and then the supersonic treatment is repeated for 3 minutes. The lipid membrane prepared in this way is used in a ceramide release assay. The ceramide release reaction for the lipid membrane and its detection is performed as follows: CERT protein or a recombinant protein thereof (under the standard conditions, the amount of protein corresponding to 450 picomoles, which is 2-fold molar equivalent amount of ceramide contained in the donating membrane was used) is mixed up to 30 pL using buffer 2 [50 mM Hepes-NaOH buffer (pH7.4) to which 100 mM NaCl and 0.5 mM EDTA have been added]. Here, the reaction is initiated by adding 20 pL of lipid membrane containing ceramide. The final concentration of phospholipids is 1 mg/mL. Ceramide is contained at a ratio of about 0.3% comparing to the total phospholipid amount. After the mixture of these has been incubated at 37° C. for 30 minutes, it is centrifuged at 50,000×g for 30 minutes and the lipid membrane is precipitated. In the case where CERT protein from *E. coli* is used, most of the protein remains in the supernatant under these centrifugation conditions. Therefore, when I4C-ceramide binds to CERT protein, it is releases from the lipid membrane and transferred to the supernatant fraction. The activity for promoting ceramide release with CERT is calculated by measuring the radioactive activity of 1% in the supernatant fraction using a liquid scintillation counter.

A further possibility to measure "activity" is an in vitro ceramide transfer assay using recombinant material or cell lysate containing CERT. Hereby, the protein-mediated transfer of ceramide between SUVs is measured as described previously (Olayioye et al., 2005). The transfer assay mixture contained donor vesicles (2 nmol lipid/ml) composed of porcine brain lipids (Avanti Polar Lipids), pyrene-labeled $C_{16}$-ceramide, and 2,4,6-trinitrophenyl-phosphatidylethanolamine (TNP-PE) (88.6:0.4:11 mol %), provided by P. Somerharju, and a 10-fold excess of acceptor vesicles composed of porcine brain lipids. Fluorescence intensity is recorded at 395 nm (excitation, 345 nm; slit widths, 4 nm) before and after the addition of 75 μg cytosol from HEK293T cells transiently expressing the GFP-tagged CERT wild type and S132A proteins (see above). Fluorescence intensities are normalized to (i) the maximum intensity obtained after the addition of Triton X-100 (0.5% final concentration) and (ii) the maximum GFP fluorescence, to account for different protein expression levels.

Another possibility to measure "activity" is a phosphorylation state analysis of CERT S132A e.g. by using an anti-phospho specific antibody in a Western blot. Whole cell extracts are obtained by solubilizing cells in NP40 extraction buffer (NEB) [50 mM Tris (pH 7.5), 150 mM NaCl, 1% NP40, 1 mM sodium orthovanadate, 10 mM sodium fluoride, and 20 mM β-glycerophosphate plus Complete protease inhibitors]. Lysates are clarified by centrifugation at 16,000×g for 10 min. Whole cell extracts or immunoprecipitated proteins are boiled in sample buffer and subjected to SDS-PAGE. The proteins are blotted onto polyvinylidine difluoride membranes (Roth). After blocking with 0.5% blocking reagent (Roche) in PBS containing 0.1% Tween 20, filters are probed with a phosphospecific antibody such as phospho-specific substrate antibody, termed pMOTIF, raised against consensus motifs phosphorylated by PKD (Doppler et al., 2005). Proteins are visualized with peroxidase-coupled secondary antibody using the enhanced chemiluminescence detection system (Pierce).

Still another assay for measuring the "activity" is a secretion assay e.g. for a model protein, an antibody or a protein of interest. Cells are cotransfected with ss-HRP-Flag plasmid and empty vector, pEGFP-N-1-PKD1KD and a plasmid encoding CERT, a variant of CERT of any START family protein at a ratio of 1:6.5, respectively. 24 h post-transfection cells are washed with serum-free media and HRP secretion is quantified after 0, 1, 3 and 6 h by incubation of clarified cell supernatant with ECL reagent. Measurements are done with a luminometer (Lucy2, Anthos) at 450 nm.

Another way to measure the "activity" is by using a fluorescent ceramide analog e.g. Bodipy-labeled C5-ceramide, perform chase experiments in intact cells and measure the accumulation of protein in the Golgi complex.

Quantification of the distribution of BODIPY® FL C5-ceramide between the Golgi and the ER: The transport of the fluorescent ceramide was quantified post-aquisition using the linescan function of the Metamorph software. A line was drawn through the cells in the confocal pictures taken in different time points and the fluorescent intensity was measured in the cytoplasm and over the Golgi complex of the cells. The "uptake ratio" was calculated from the fluorescent light intensity in the Golgi divided by the intensity measured in the cytoplasm. The maximum uptake ratio was measured in control cells after 25 min incubation on 37° C. and this value was taken as 100 percent. The quantification was made from the data of three independent experiments in which confocal pictures were taken in twelve different time points and in each time points 7 cells were analyzed.

The term "productivity" or "specific productivity" describes the quantity of a specific protein which is produced by a defined number of cells within a defined time. The specific productivity is therefore a quantitative measure for the capacity of cells to express/synthesize/produce a protein of interest. In the context of industrial manufacturing, the specific productivity is usually expressed as amount of protein in picogram produced per cell and day ('pg/cell*day' or 'pcd').

One method to determine the "specific productivity" of a secreted protein is to quantitatively measure the amount of protein of interest secreted into the culture medium by enzyme linked immunosorbent assay (ELISA). For this purpose, cells are seeded into fresh culture medium at defined densities. After a defined time, e.g. after 24, 48 or 72 hours, a sample of the cell culture fluid is taken and subjected to ELISA measurement to determine the titer of the protein of interest. The specific productivity can be determined by dividing the titer by the average cell number and the time.

Another example how to measure the "specific productivity" of cells is provided by the homogenous time resolved fluorescence (HTRF®) assay.

"Producitvity" of cells for an intracellular, membrane-associated or transmembrane protein can also be detected and quantified by Western Blotting. The cells are first washed and subsequently lysed in a buffer containing either detergents such as Triton-X, NP-40 or SDS or high salt concentrations. The proteins within the cell lysate are than separated by size on SDS-PAGE, transferred to a nylon membrane where the protein of interest is subsequently detected and visualized by using specific antibodies.

Another method to determine the "specific productivity" of a cell is to immunologically detect the protein of interest by fluorescently labeled antibodies raised against the protein of interest and to quantify the fluorescence signal in a flow cytometer. In case of an intracellular protein, the cells are first fixed, e.g. in paraformaldehyde buffer, and than permeabilized to allow penetration of the detection antibody into the cell. Cell surface proteins can be quantified on the living cell without need for prior fixation or permeabilization.

The "productivity" of a cell can furthermore by determined indirectly by measuring the expression of a reporter protein such as the green fluorescent protein (GFP) which is expressed either as a fusion protein with the protein of interest or from the same mRNA as the protein of interest as part of a bi-, tri-, or multiple expression unit.

The term "enhancement/increase of productivity" comprises methods to increase/enhance the specific productity of cells. The specific productivity is increased or enhanced, if the productivity is higher in the cells under investigation compared to the respective control cells and if this difference is statistically significant. The cells under investigation can be heterogenous populations or clonal cell lines of treated, transfected or genetically modified cells; untreated, untransfected or unmodified cells can serve as control cells.

The terms "inhibitor" or "suppressor" as used in the present invention means any molecule that acts to inhibit or suppress the expression or activity of a START domain protein like CERT. The term includes small chemical compounds, nucleic acids such as antisense DNA, antisense RNA or siRNA, single chain antibodies and proteins that block CERT transcription and translation as well as peptides or proteins that interfere with lipid binding of START domain proteins such as CERT.

"Host cells" in the meaning of the present invention are cells such as hamster cells, preferably BHK21, BHK TK$^-$, CHO, CHO-K1, CHO-DUKX, CHO-DUKX B1, and CHO-DG44 cells or the derivatives/progenies of any of such cell line. Particularly preferred are CHO-DG44, CHO-DUKX, CHO-K1 and BHK21, and even more preferred CHO-DG44 and CHO-DUKX cells. In a further embodiment of the present invention host cells also mean murine myeloma cells, preferably NS0 and Sp2/0 cells or the derivatives/progenies of any of such cell line. Examples of murine and hamster cells which can be used in the meaning of this invention are also summarized in Table 1. However, derivatives/progenies of those cells, other mammalian cells, including but not limited to human, mice, rat, monkey, and rodent cell lines, or eukaryotic cells, including but not limited to yeast, insect and plant cells, can also be used in the meaning of this invention, particularly for the production of biopharmaceutical proteins.

TABLE 1

| Eukaryotic production cell lines | |
|---|---|
| CELL LINE | ORDER NUMBER |
| NS0 | ECACC No. 85110503 |
| Sp2/0-Ag14 | ATCC CRL-1581 |
| BHK21 | ATCC CCL-10 |
| BHK TK$^-$ | ECACC No. 85011423 |
| Hak | ATCC CCL-15 |
| 2254-62.2 (BHK-21 derivative) | ATCC CRL-8544 |
| CHO | ECACC No. 8505302 |
| CHO wild type | ECACC 00102307 |
| CHO-K1 | ATCC CCL-61 |
| CHO-DUKX (= CHO duk$^-$, CHO/dhfr$^-$) | ATCC CRL-9096 |
| CHO-DUKX B11 | ATCC CRL-9010 |
| CHO-DG44 | (Urlaub et al., 1983) |
| CHO Pro-5 | ATCC CRL-1781 |
| V79 | ATCC CCC-93 |
| B14AF28-G3 | ATCC CCL-14 |
| HEK 293 | ATCC CRL-1573 |

TABLE 1-continued

| Eukaryotic production cell lines | |
|---|---|
| CELL LINE | ORDER NUMBER |
| COS-7 | ATCC CRL-1651 |
| U266 | ATCC TIB-196 |
| HuNS1 | ATCC CRL-8644 |
| CHL | ECACC No. 87111906 |

Host cells are most preferred, when being established, adapted, and completely cultivated under serum free conditions, and optionally in media which are free of any protein/peptide of animal origin. Commercially available media such as Ham's F12 (Sigma, Deisenhofen, Germany), RPMI-1640 (Sigma), Dulbecco's Modified Eagle's Medium (DMEM; Sigma), Minimal Essential Medium (MEM; Sigma), Iscove's Modified Dulbecco's Medium (IMDM; Sigma), CD-CHO (Invitrogen, Carlsbad, Calif.), CHO-S-Invtirogen), serum-free CHO Medium (Sigma), and protein-free CHO Medium (Sigma) are exemplary appropriate nutrient solutions. Any of the media may be supplemented as necessary with a variety of compounds examples of which are hormones and/or other growth factors (such as insulin, transferrin, epidermal growth factor, insulin like growth factor), salts (such as sodium chloride, calcium, magnesium, phosphate), buffers (such as HEPES), nucleosides (such as adenosine, thymidine), glutamine, glucose or other equivalent energy sources, antibiotics, trace elements. Any other necessary supplements may also be included at appropriate concentrations that would be known to those skilled in the art. In the present invention the use of serum-free medium is preferred, but media supplemented with a suitable amount of serum can also be used for the cultivation of host cells. For the growth and selection of genetically modified cells expressing the selectable gene a suitable selection agent is added to the culture medium.

The term "protein" is used interchangeably with amino acid residue sequences or polypeptide and refers to polymers of amino acids of any length. These terms also include proteins that are post-translationally modified through reactions that include, but are not limited to, glycosylation, acetylation, phosphorylation or protein processing. Modifications and changes, for example fusions to other proteins, amino acid sequence substitutions, deletions or insertions, can be made in the structure of a polypeptide while the molecule maintains its biological functional activity. For example certain amino acid sequence substitutions can be made in a polypeptide or its underlying nucleic acid coding sequence and a protein can be obtained with like properties.

The term "polypeptide" means a sequence with more than 10 amino acids and the term "peptide" means sequences up to 10 amino acids length.

The present invention is suitable to generate host cells for the production of biopharmaceutical polypeptides/proteins. The invention is particularly suitable for the high-yield expression of a large number of different genes of interest by cells showing an enhanced cell productivity.

"Gene of interest" (GOI), "selected sequence", or "product gene" have the same meaning herein and refer to a polynucleotide sequence of any length that encodes a product of interest or "protein of interest", also mentioned by the term "desired product". The selected sequence can be full length or a truncated gene, a fusion or tagged gene, and can be a cDNA, a genomic DNA, or a DNA fragment, preferably, a cDNA. It can be the native sequence, i.e. naturally occurring form(s), or can be mutated or otherwise modified as desired. These modifications include codon optimizations to optimize codon usage in the selected host cell, humanization or tagging. The selected sequence can encode a secreted, cytoplasmic, nuclear, membrane bound or cell surface polypeptide.

The "protein of interest" includes proteins, polypeptides, fragments thereof, peptides, all of which can be expressed in the selected host cell. Desired proteins can be for example antibodies, enzymes, cytokines, lymphokines, adhesion molecules, receptors and derivatives or fragments thereof, and any other polypeptides that can serve as agonists or antagonists and/or have therapeutic or diagnostic use. Examples for a desired protein/polypeptide are also given below.

In the case of more complex molecules such as monoclonal antibodies the GOI encodes one or both of the two antibody chains.

The "product of interest" may also be an antisense RNA.

"Proteins of interest" or "desired proteins" are those mentioned above. Especially, desired proteins/polypeptides or proteins of interest are for example, but not limited to insulin, insulin-like growth factor, hGH, tPA, cytokines, such as interleukines (IL), e.g. IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumor necrosisfactor (TNF), such as TNF alpha and TNF beta, TNF gamma, TRAIL; G-CSF, GM-CSF, M-CSF, MCP-1 and VEGF. Also included is the production of erythropoietin or any other hormone growth factors. The method according to the invention can also be advantageously used for production of antibodies or fragments thereof. Such fragments include e.g. Fab fragments (Fragment antigen-binding=Fab). Fab fragments consist of the variable regions of both chains which are held together by the adjacent constant region. These may be formed by protease digestion, e.g. with papain, from conventional antibodies, but similar Fab fragments may also be produced in the mean time by genetic engineering. Further antibody fragments include F(ab')2 fragments, which may be prepared by proteolytic cleaving with pepsin.

The protein of interest is preferably recovered from the culture medium as a secreted polypeptide, or it can be recovered from host cell lysates if expressed without a secretory signal. It is necessary to purify the protein of interest from other recombinant proteins and host cell proteins in a way that substantially homogenous preparations of the protein of interest are obtained. As a first step, cells and/or particulate cell debris are removed from the culture medium or lysate. The product of interest thereafter is purified from contaminant soluble proteins, polypeptides and nucleic acids, for example, by fractionation on immunoaffinity or ion-exchange columns, ethanol precipitation, reverse phase HPLC, Sephadex chromatography, chromatography on silica or on a cation exchange resin such as DEAE. In general, methods teaching a skilled person how to purify a protein heterologous expressed by host cells, are well known in the art. Such methods are for example described by (Harris and Angal, 1995) or (Robert Scopes, 1988).

Using genetic engineering methods it is possible to produce shortened antibody fragments which consist only of the variable regions of the heavy (VH) and of the light chain (VL). These are referred to as Fv fragments (Fragment variable=fragment of the variable part). Since these Fv-fragments lack the covalent bonding of the two chains by the cysteines of the constant chains, the Fv fragments are often stabilised. It is advantageous to link the variable regions of the heavy and of the light chain by a short peptide fragment, e.g. of 10 to 30 amino acids, preferably 15 amino acids. In this way a single peptide strand is obtained consisting of VH and VL, linked by a peptide linker. An antibody protein of this kind is known as a single-chain-Fv (scFv). Examples of scFv-antibody proteins of this kind known from the prior art are described in (Huston et al., 1988).

In recent years, various strategies have been developed for preparing scFv as a multimeric derivative. This is intended to lead, in particular, to recombinant antibodies with improved pharmacokinetic and biodistribution properties as well as with increased binding avidity. In order to achieve multimerisation of the scFv, scFv were prepared as fusion proteins with multimerisation domains. The multimerisation domains may be, e.g. the CH3 region of an IgG or coiled coil structure (helix structures) such as Leucin-zipper domains. However, there are also strategies in which the interaction between the VH/VL regions of the scFv are used for the multimerisation (e.g. dia-, tri- and pentabodies). By diabody the skilled person means a bivalent homodimeric scFv derivative. The shortening of the Linker in an scFv molecule to 5-10 amino acids leads to the formation of homodimers in which an inter-chain VH/VL-superimposition takes place. Diabodies may additionally be stabilised by the incorporation of disulphide bridges. Examples of diabody-antibody proteins from the prior art can be found in (Perisic et al., 1994).

By minibody the skilled person means a bivalent, homodimeric scFv derivative. It consists of a fusion protein which contains the CH3 region of an immunoglobulin, preferably IgG, most preferably IgG1 as the dimerisation region which is connected to the scFv via a Hinge region (e.g. also from IgG1) and a Linker region. Examples of minibody-antibody proteins from the prior art can be found in (Hu et al., 1996).

By triabody the skilled person means a: trivalent homotrimeric scFv derivative (Kortt et al., 1997). ScFv derivatives wherein VH-VL are fused directly without a linker sequence lead to the formation of trimers.

By "scaffold proteins" a skilled person means any functional domain of a protein that is coupled by genetic cloning or by co-translational processes with another protein or part of a protein that has another function.

The skilled person will also be familiar with so-called miniantibodies which have a bi-, tri- or tetravalent structure and are derived from scFv. The multimerisation is carried out by di-, tri- or tetrameric coiled coil structures (Lovejoy et al., 1993; Pack et al., 1993; Pack et al., 1995).

By definition any sequences or genes introduced into a host cell are called "heterologous sequences" or "heterologous genes" or "transgenes" with respect to the host cell, even if the introduced sequence or gene is identical to an endogenous sequence or gene in the host cell.

A "heterologous" protein is thus a protein expressed from a heterologous sequence.

Heterologous gene sequences can be introduced into a target cell by using an "expression vector", preferably an eukaryotic, and even more preferably a mammalian expression vector. Methods used to construct vectors are well known to a person skilled in the art and described in various publications. In particular techniques for constructing suitable vectors, including a description of the functional components such as promoters, enhancers, termination and polyadenylation signals, selection markers, origins of replication, and splicing signals, are reviewed in considerable details in (Sambrook et al., 1989) and references cited therein. Vectors may include but are not limited to plasmid vectors, phagemids, cosmids, articificial/mini-chromosomes (e.g. ACE), or viral vectors such as baculovirus, retrovirus, adenovirus, adeno-associated virus, herpes simplex virus, retroviruses, bacteriophages. The eukaryotic expression vectors will typically contain also prokaryotic sequences that facilitate the propagation of the vector in bacteria such as an origin of replication and antibiotic resistance genes for selection in bacteria. A variety of eukaryotic expression vectors, containing a cloning site into which a polynucleotide can be operatively linked, are well known in the art and some are commercially available from companies such as Stratagene, La Jolla, Calif.; Invitrogen, Carlsbad, Calif.; Promega, Madison, Wis. or BD Biosciences Clontech, Palo Alto, Calif.

In a preferred embodiment the expression vector comprises at least one nucleic acid sequence which is a regulatory sequence necessary for transcription and translation of nucleotide sequences that encode for a peptide/polypeptide/protein of interest.

The term "expression" as used herein refers to transcription and/or translation of a heterologous nucleic acid sequence within a host cell. The level of expression of a desired product/protein of interest in a host cell may be determined on the basis of either the amount of corresponding mRNA that is present in the cell, or the amount of the desired polypeptide/protein of interest encoded by the selected sequence as in the present examples. For example, mRNA transcribed from a selected sequence can be quantitated by Northern blot hybridization, ribonuclease RNA protection, in situ hybridization to cellular RNA or by PCR (see (Sambrook et al., 1989); (Ausubel et al., 2002) updated). Proteins encoded by a selected sequence can be quantitated by various methods, e.g. by ELISA, by Western blotting, by radioimmunoassays, by immunoprecipitation, by assaying for the biological activity of the protein, by immunostaining of the protein followed by FACS analysis (see (Sambrook et al., 1989); (Ausubel et al., 2002) updated) or by homogeneous time-resolved fluorescence (HTRF) assays.

"Transfection" of eukaryotic host cells with a polynucleotide or expression vector, resulting in genetically modified cells or transgenic cells, can be performed by any method well known in the art and described, e.g., in (Sambrook et al., 1989) or (Ausubel et al., 2002) updated. Transfection methods include but are not limited to liposome-mediated transfection, calcium phosphate co-precipitation, electroporation, polycation (such as DEAE-dextran)-mediated transfection, protoplast fusion, viral infections and microinjection. Preferably, the transfection is a stable transfection. The transfection method that provides optimal transfection frequency and expression of the heterologous genes in the particular host cell line and type is favoured. Suitable methods can be determined by routine procedures. For stable transfectants the constructs are either integrated into the host cell's genome or an artificial chromosome/mini-chromosome or located episomally so as to be stably maintained within the host cell.

The practice of the present invention will employ, unless otherwise indicated, conventional techniques of cell biology, molecular biology, cell culture, immunology and the like which are in the skill of one in the art. These techniques are fully disclosed in the current literature. See e.g. Sambrook et al., Molecular Cloning: A Laboratory Manual, $2^{nd}$ Ed., Cold Spring Harbor Laboratory Press, Cold Spring Harbor, N.Y. (1989); Ausubel et al., Current Protocols in Molecular Biology (1987, updated); Brown ed., Essential Molecular Biology, IRL Press (1991); Goeddel ed., Gene Expression Technology, Academic Press (1991); Bothwell et al. eds., Methods for Cloning and Analysis of Eukaryotic Genes, Bartlett Publ. (1990); Wu et al., eds., Recombinant DNA Methodology, Academic Press (1989); Kriegler, Gene Transfer and Expression, Stockton Press (1990); McPherson et al., PCR: A Practical Approach, IRL Press at Oxford University Press (1991); Gait ed., Oligonucleotide Synthesis (1984); Miller & Calos eds., Gene Transfer Vectors for Mammalian Cells (1987); Butler ed., Mammalian Cell Biotechnology (1991); Pollard et al., eds., Animal Cell Culture, Humana Press (1990); Freshney et al., eds., Culture of Animal Cells, Alan R. Liss (1987); Studzinski, ed., Cell Growth and Apoptosis, A Practical Approach, IRL Press at Oxford University Press (1995); Melamed et al., eds., Flow Cytometry and Sorting, Wiley-Liss (1990); Current Protocols in Cytometry, John Wiley & Sons, Inc. (updated); Wirth & Hauser, Genetic Engineering of Animals Cells, in: Biotechnology Vol. 2, Pühler ed., VCH, Weinheim 663-744; the series Methods of Enzymology (Academic Press, Inc.), and Harlow et al., eds., Antibodies: A Laboratory Manual (1987).

Embodiments

The invention relates to a method of producing a heterologous protein of interest in a cell comprising increasing the expression or activity of a protein having an amino acid sequence comprising a steroidogenic acute regulatory related lipid transfer (START) domain or aderivative or mutant thereof, and effecting the expression of said protein of interest. In a preferred embodiment of the present invention the method is characterized in that the heterologous protein is a membrane or secreted protein.

In a specific embodiment of the present invention the method is characterized in that the START domain protein is a mammalian START domain family member such as PCTP (SEQ ID NO. 27), StarD7, GPBP, StarD10, StarD8, StarD13, DLC-1, StarD4 (SEQ ID NO. 21), StarD6 (SEQ ID NO. 25), StarD5 (SEQ ID NO. 23), MLN64, StAR, THEA-2, CACH or StarD9 or a derivative or mutant thereof.

In a further specific embodiment of the present invention the method is characterized in that the START domain protein is characterized by being induced upon ER stress and/or is structurally characterized by consisting solely of a START domain such as StarD4 (SEQ ID NO. 21), StarD5 (SEQ ID NO. 23), StarD6 (SEQ ID NO. 25) or phosphatidylcholin transfer protein (PCTP) (SEQ ID NO. 27).

In another specific embodiment of the present invention the method is characterized in that the START domain protein is selected from the group consisting of CERT (SEQ ID NO. 11 or 13), StarD4 (SEQ ID NO. 21) and StarD5 (SEQ ID NO. 23).

In a further embodiment of the present invention the method is characterized in that the START domain protein is StarD6 (SEQ ID NO. 25). In a preferred embodiment StarD6 is encoded by a nucleotide with the SEQ ID NO. 24.

In a preferred embodiment of the present invention the method is characterized in that the START domain comprises at least the 219 amino acid START domain of $CERT_L$ (SEQ ID NO. 19), or at least the 223 amino acid START domain of CERT and CERT S132A (SEQ ID NO. 17), or at least the START domain of StarD4 (SEQ ID NO. 21) or at least the START domain of StarD5 (SEQ ID NO. 23) or a derivative or mutant thereof.

In a particularly preferred embodiment of the present invention the method is characterized in that the START domain protein is ceramide transfer protein CERT (CERT=SEQ ID NO. 11 or $CERT_L$=SEQ ID NO. 13) or a derivative or mutant thereof.

In another specific embodiment of the present invention the method is characterized in that the START domain protein is mutated ceramide transfer protein CERT and said mutation disables and/or deletes a phosphorylation site at any serine, threonine or tyrosine position of CERT.

In a further specific embodiment of the present invention the method is characterized in that the START domain protein is mutated ceramide transfer protein CERT and said mutation disables and/or deletes the protein kinase D (PKD) phosphorylation site of CERT at position 132.

In a particularly preferred embodiment of the present invention the method is characterized in that the mutated CERT is $CERT_{S132A}$ (SEQ ID NO. 15).

In another embodiment of the present invention the method is characterized in that said method results in increased specific cellular productivity of said protein of interest in said cell in comparison to a control cell expressing said protein of interest, but whereby said control cell does not have increased expression or activity of a protein having an amino acid sequence comprising a steroidogenic acute regulatory related lipid transfer (START) domain or a derivative or mutant thereof.

In another specific embodiment of the present invention the method is characterized in that the increase in productivity is about 5% to about 10%, about 11% to about 20%, about 21% to about 30%, about 31% to about 40%, about 41% to about 50%, about 51% to about 60%, about 61% to about 70%, about 71% to about 80%, about 81% to about 90%, about 91% to about 100%, about 101% to about 149%, about 150% to about 199%, about 200% to about 299%, about 300% to about 499%, or about 500% to about 1000%.

In a preferred embodiment of the present invention the method is characterized in that said cell is a eukaryotic cell such as a yeast, plant, worm, insect, avian, fish, reptile or mammalian cell. In a specific embodiment of the present invention the method is characterized in that said cell is an animal cell. In a further specific embodiment of the present invention the method is characterized in that said cell is a metazoan cell such as *C. elegans*. In another specific embodiment of the present invention the method is characterized in that said cell is a bilateria cell such as *Drosophila melanogaster*. In a further embodiment of the present invention the method is characterized in that said cell is a vertebrate cell such as an avian, fish, reptile or mammalian cell. In a specific embodiment of the present invention the method is characterized in that said cell is a human cell such as the human myeloma celline U266, HEK293, HeLa, HepG2 or HT1080. In a preferred embodiment of the present invention the method is characterized in that said cell is a rodent cell such as murine NSO, Sp2/0 or Ag8653 cell, YO or YB2.0.

In a further embodiment of the present invention the method is characterized in that said eukaryotic cell is a mammalian cell.

In a specific embodiment of the present invention the method is characterized in that said mammalian cell is a Chinese Hamster Ovary (CHO), monkey kidney CV1, monkey kidney COS, human lens epithelium PER.C6TM, human embryonic kidney, HEK293, baby hamster kidney, African green monkey kidney, human cervical carcinoma, canine kidney, buffalo rat liver, human lung, human liver, mouse mammary tumor or myeloma cell, a dog, pig or macaque cell, rat, rabbit, cat, goat, preferably a CHO cell.

In a preferred embodiment of the present invention the method is characterized in that said CHO cell is CHO wild type, CHO K1, CHO DG44, CHO DUKX-B11, CHO Pro-5, preferably CHO DG44.

In a specific embodiment of the present invention the method is characterized in that the protein of interest is a membrane or secreted protein. In a preferred embodiment of the present invention the method is characterized in that the protein of interest is an antibody or antibody fragment.

In a further preferred embodiment of the present invention the method is characterized in that the antibody is monoclonal, polyclonal, mammalian, murine, chimeric, humanized, primatized, primate, human or an antibody fragment or derivative thereof such as antibody, immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, or a fusion polypeptide of one of the above fragments with another peptide or polypeptide, Fc-peptide fusion, Fc-toxine fusion, scaffold proteins.

The invention further relates to a method for increasing secretion of a membrane or secreted protein of interest in a cell comprising expressing said protein of interest and expressing a protein having an amino acid sequence comprising a steroidogenic acute regulatory related lipid transfer (START) domain or a derivative or mutant thereof.

The invention further relates to a method of producing a membrane or secreted protein of interest in a cell comprising increasing the expression of a protein having an amino acid sequence comprising a steroidogenic acute regulatory related lipid transfer (START) domain or a derivative or mutant thereof, and effecting the expression of said protein of interest, whereby the order or steps a and b may be reversed.

In a specific embodiment of the present invention the method is further characterized in that step a) is carried out before step b). In a further specific embodiment of the present invention the method is further characterized in that step a) and b) are carried out simultaneously. In another embodiment of the present invention the method is further characterized in that step b) is carried out before step a).

In a preferred embodiment of the present invention the method further comprises an additional step of recovering the protein of interest.

In an especially preferred embodiment of the present invention the method further comprises an additional step of isolating and purifying the protein of interest.

In a specific embodiment of the present invention the method comprises increasing the expression of a protein having an amino acid sequence comprising a steroidogenic acute regulatory related lipid transfer (START) domain or a derivative or mutant thereof by transfecting a cell with a polynucleotide encoding for a protein having an amino acid sequence comprising a steroidogenic acute regulatory related lipid transfer (START) domain or a derivative or mutant thereof.

In a specific embodiment of the present invention the method comprises transfecting said cell with a first polynucleotide encoding for a protein having an amino acid sequence comprising a steroidogenic acute regulatory related lipid transfer (START) domain or a derivative or mutant thereof and transfecting said cell with a second polynucleotide encoding for a protein of interest.

In a specific embodiment of the present invention the START domain protein of the method is characterized by being induced upon ER stress and/or is structurally characterized by having no further structural motifs besides the START domain such as StarD4 (SEQ ID NO. 21), StarD5 (SEQ ID NO: 23), StarD6 (SEQ ID NO. 25) or PCTP (SEQ ID NO: 27).

In a preferred embodiment of the present invention the method comprises increasing the expression of a protein having an amino acid sequence comprising a steroidogenic acute regulatory related lipid transfer (START) domain or a derivative or mutant thereof, preferably by transfecting said cell with a first polynucleotide encoding for a protein having an amino acid sequence comprising a steroidogenic acute regulatory related lipid transfer (START) domain or a derivative or mutant thereof, whereby the increase is measured in comparison to an untransfected cell, transfecting said cell with a second polynucleotide encoding for a protein of interest In a preferred embodiment of the present invention the method is characterized by that the proteins expressed in step a) and b) are not identical.

The invention further relates to a method of producing a membrane or secreted protein of interest in a cell comprising Increasing the expression of a protein having an amino acid sequence comprising a steroidogenic acute regulatory related lipid transfer (START) domain or a derivative or mutant thereof in said cell and effecting the expression of said protein of interest in said cell.

The invention furthermore relates to a method of producing a membrane or secreted protein of interest in a cell comprising increasing the expression of a protein having an amino acid sequence comprising a steroidogenic acute regulatory related lipid transfer (START) domain or a derivative or mutant thereof in said cell and expressing said protein of interest in said cell.

In a specific embodiment of the present invention the method is characterized in that said method results in increased specific cellular productivity of said protein of interest in said cell in comparison to a control cell previously transfected with a polynucleotide encoding for the protein of interest, but whereby said control cell does not have increased expression of a protein having an amino acid sequence comprising a steroidogenic acute regulatory related lipid transfer (START) domain or a derivative or mutant thereof.

In a specific embodiment of the present invention the method is characterized in that the protein of interest is a protein which is passing through the Golgi complex.

The invention further relates to a method of increasing specific cellular productivity of a membrane or secreted protein of interest in a cell comprising introducing into a cell one or more vector systems comprising nucleic acid sequences encoding for at least two polypeptides whereby a first polynucleotide encodes a protein having an amino acid sequence comprising a steroidogenic acute regulatory related lipid transfer (START) domain or a derivative or mutant thereof and a second polynucleotide encodes a protein of interest and whereby the protein of interest and the protein having an amino acid sequence comprising a steroidogenic acute regulatory related lipid transfer (START) domain or a derivative or mutant thereof are expressed by said cell.

The invention furthermore relates to a method of increasing the transfection efficiency of a cell expressing a membrane or secreted protein of interest in a cell comprising transfecting said cell with a first polynucleotide encoding a protein having an amino acid sequence comprising a steroidogenic acute regulatory related lipid transfer (START) domain or a derivative or mutant thereof, subsequently transfecting said cell with a second polynucleotide encoding a protein of interest, whereby said first and second polynucleotides are located on different vector systems.

In a further embodiment the invention relates to a method of increasing the transfection efficiency of a cell comprising the additional step of transfecting a reporter gene such as GFP, YFP, HRP, SEAP or LacZ, which might be fused to the protein of interest, located on the same expression construct or on a separate plasmid.

In a preferred embodiment the invention relates to a method of increasing the transfection efficiency of a cell comprising the additional step of detecting and/or measuring the transfection efficiency by either detection of the protein of interest or the expression of the reporter gene.

The invention further relates to an expression vector comprising two polynucleotides, a first polynucleotide encoding for a protein having an amino acid sequence comprising a steroidogenic acute regulatory related lipid transfer (START) domain or a derivative or mutant thereof and a second polynucleotide encoding for a protein of interest.

In a specific embodiment of the present invention the expression vector is characterized in that the START domain protein is a mammalian START domain family member such as PCTP (SEQ ID NO. 27), StarD7, GPBP, StarD10, StarD8, StarD13, DLC-1, StarD4 (SEQ ID NO. 21), StarD6 (SEQ ID NO. 25), StarD5 (SEQ ID NO. 23), MLN64, StAR, THEA-2, CACH or StarD9 or a derivative or mutant thereof.

In another embodiment of the present invention the expression vector is characterized in that the START domain protein is ceramide transfer protein CERT (CERT=SEQ ID NO. 11 or $CERT_L$=SEQ ID NO. 13) or a derivative or mutant thereof.

In a specific embodiment of the present invention the expression vector is characterized in that the mutated CERT is $CERT_{S132A}$ (SEQ ID NO. 15).

In a specific embodiment of the present invention the expression vector is characterized in that said first polynucleotide increases the protein transport in a cell via the secretory pathway.

In a specific embodiment of the present invention the expression vector is characterized in that the START domain protein is mutated ceramide transfer protein CERT and said mutation disables and/or deletes a phosphorylation site at any serine, threonine or tyrosine position within the CERT protein.

In another embodiment of the present invention the expression vector is characterized in that the START domain protein is mutated ceramide transfer protein CERT and said mutation disables and/or deletes the protein kinase D (PKD) phosphorylation site of CERT at position 132.

The present invention further relates to a cell comprising the expression vector of the invention. In a specific embodiment of the present invention the cell is characterized in that said cell is a eukaryotic cell such as a yeast, plant, worm, insect, avian, fish, reptile or mammalian cell. In a specific embodiment of the present invention the cell is characterized in that said eukaryotic cell is a mammalian cell.

In a specific embodiment of the present invention the cell is characterized in that said mammalian cell is a Chinese Hamster Ovary (CHO), monkey kidney CV1, monkey kidney COS, human lens epithelium PER.C6TM, human embryonic kidney, HEK 293, baby hamster kidney, African green monkey kidney, human cervical carcinoma, canine kidney, buffalo rat liver, human lung, human liver, mouse mammary tumor or myeloma cell, a dog, pig or macaque cell, rat, rabbit, cat, goat, preferably a CHO cell. In a specific embodiment of the present invention the cell is characterized in that said CHO cell is CHO wild type, CHO K1, CHO DG44, CHO DUKX-B11, CHO Pro-5, preferably CHO DG44.

In a specific embodiment of the present invention the cell is characterized in that said cell is an animal cell, preferably a metazoan cell such as *C. elegans*. In a further embodiment of the present invention the cell is characterized in that said cell is a bilateria cell such as *Drosophila melanogaster*, preferably a vertebrate cell such as an avian, fish, reptile or mammalian cell. In a specific embodiment of the present invention the cell is characterized in that said eukaryotic cell is a mammalian cell, preferably a human cell such as a the human myeloma celline U266, HEK293, HeLa, HepG2 or HT1080, more preferably a rodent cell such as murine NSO, Sp2/0 or Ag8653 cell, YO or YB2.0.

The invention further relates to a protein of interest, preferably an antibody produced by any of the methods described.

The invention further relates to a pharmaceutical composition comprising a polynucleotide sequence useful for blocking or reducing the expression of a protein having an amino acid sequence comprising a steroidogenic acute regulatory related lipid transfer (START) domain or a derivative or mutant thereof. The invention furthermore relates to a pharmaceutical composition comprising a polynucleotide sequence which blocks or reduces the expression of a protein having an amino acid sequence comprising a START domain or a derivative or mutant thereof.

In a specific embodiment of the present invention the pharmaceutical composition is characterized in that the START domain sequence is ceramide transfer protein CERT (CERT=SEQ ID NO. 11 or $CERT_L$=SEQ ID NO. 13) or a derivative or mutant thereof.

In another specific embodiment of the present invention the pharmaceutical composition is characterized in that the START domain is (SEQ ID NO. 17 or 19) or a derivative or mutant thereof.

In a specific embodiment of the present invention the pharmaceutical composition is characterized in that the polynucleotide sequence is RNAi, siRNA or antisense-RNA.

In a preferred embodiment of the present invention the pharmaceutical composition is characterized in that the START domain protein is a mammalian START domain family member such as PCTP (SEQ ID NO. 27), StarD7, GPBP, StarD10, StarD8, StarD13, DLC-1, StarD4 (SEQ ID NO. 21), StarD6 (SEQ ID NO. 25), StarD5 (SEQ ID NO. 23), MLN64, STAR, THEA-2, CACH or StarD9 or a derivative or mutant thereof.

In a particularly preferred embodiment of the present invention the pharmaceutical composition is characterized in that said polynucleotide is complementary to the CERT nucleotide sequence or parts thereof, especially to the START domain.

In a most preferred embodiment of the present invention the pharmaceutical composition is characterized in that said polynucleotide binds to either the CERT gene or the CERT promoter.

In a further embodiment of the present invention the pharmaceutical composition is characterized in that said polynucleotide is anti-sense oligonucleotide to the CERT gene or parts thereof.

The invention further relates to a pharmaceutical composition comprising an inhibitor or suppressor of a protein having an amino acid sequence comprising a steroidogenic acute regulatory related lipid transfer (START) domain, preferably CERT (SEQ ID NO. 11 or SEQ ID NO. 13) or a derivative or mutant thereof.

In a specific embodiment of the present invention the pharmaceutical composition is characterized in that said inhibitor or suppressor is a chemical substance or a peptide-inhibitor or an inhibiting protein such as. (i) protein binding to CERT promoter thereby inhibiting CERT expression, (ii) protein binding to CERT or PKD thus preventing binding of PKD and CERT and hindering CERT phosphorylation by PKD, (iii) a protein similar to CERT which however does not fulfill CERT functions, that means a "dominant-negative" CERT variant, or (iv) a protein acting as scaffold for both CERT and PKD, resulting in irreversible binding of CERT to PKD (=a stable PKD/CERT complex) which is not functional due to the inhibitory phosphorylation of CERT by PKD and the hindering of dissociation of CERT from said complex.

In a specific embodiment of the present invention the pharmaceutical composition is characterized in that said inhibitor or suppressor is a inhibitor or suppressor of CERT activity.

The invention further relates to a method for identifying a modulator of START domain protein function, preferably CERT function, comprising providing a protein having an amino acid sequence comprising a steroidogenic acute regulatory related lipid transfer (START) domain or a derivative or mutant thereof, preferably CERT, contacting said protein of step a) with a test agent, determining an effect related to increased or decreased protein secretion or expression of cell-surface proteins.

The invention further relates to a method comprising application of a pharmaceutical composition as described for the treatment of cancer.

The invention furthermore relates to a use of a START domain protein or a polynucleotide encoding for a START domain protein to increase secretion and/or production of a protein of interest.

The invention further relates to a diagnostic use of any of the methods, expression vectors, cells or pharmaceutical compositions as described.

In a specific embodiment the invention further relates to a method of producing a heterologous protein of interest in a cell comprising increasing the expression or activity of a protein having an amino acid sequence comprising a steroidogenic acute regulatory related lipid transfer (START) domain consensus sequence or a derivative or mutant thereof as listed below,

```
CONSENSUS/80%                                (SEQ ID NO 28)
nhnntnnntnhtnhhntnnnWnnnnnnnnnnnnnnnnnhhthnnnnnnnn

nnnnnnnnnnn+hnthhnnnnnnnhnnnhhntnnnnnntWppnhnnnnnn

nnnnnnhthlpnhtnsnnnnnnnnsnlnhnnntnnhnnnhnsnR-hhnlR

nhpnnnnnnnnnnnttnhhlhnnohpnntnnnnnnnnnthhRsphhnshh

hhpnnttsnnnnnnnnnnnnsphhhlnnh-htsnnnnnnnpnhhpnhhtn

thnnhhpnnnnhtthptntnp
```

Whereby the class key residues are (represented in the one letter amino acid code):

| | |
|---|---|
| alcohol o | S, T |
| aliphatic l | I, L, V |
| any n | A, C, D, E, F, G, H, I, K, L, M, N, P, Q, R, S, T, V, W, Y |
| aromatic a | F, H, W, Y |
| charged c | D, E, H, K, R |
| hydrophobic h | A, C, F, G, H, I, K, L, M, R, T, V, W, Y |
| negative – | D, E |
| polar p | C, D, E, H, K, N, Q, R, S, T |
| positive + | H, K, R |
| small s | A, C, D, G, N, P, S, T, V |
| tiny u | A, G, S |
| turnlike t | A, C, D, E, G, H, K, N, Q, R, S, T |

and effecting the expression of said protein of interest.

In further preferred embodiments of the invention the protein having an amino acid sequence comprising a steroidogenic acute regulatory related lipid transfer (START) domain in any of the previous embodiments (e.g. expression vectors, cells, proteins, pharmaceutical compositions, methods and uses) is defined by comprising a START domain consensus sequence or a derivative or mutant thereof as listed above (SEQ ID NO 28; see also FIG. 9).

The invention generally described above will be more readily understood by reference to the following examples, which are hereby included merely for the purpose of illustration of certain embodiments of the present invention. The following examples are not limiting. They merely show possible embodiments of the invention. A person skilled in the art could easily adjust the conditions to apply it to other embodiments.

EXPERIMENTAL

Materials and Methods

Antibodies and Reagents

Antibodies are: rabbit anti-PKD substrate polyclonal antibody (Cell Signaling), mouse anti-Flag monoclonal antibody (Sigma-Aldrich), mouse anti-GFP monoclonal antibody (Roche), rabbit anti-PKD polyclonal antibody (C-20, Santa Cruz Biotechnology), mouse anti-GS28 (BD Biosciences) and mouse anti-tubulin (Neomarkers). The phosphospecific anti-pS916 PKD antibody monitoring PKD autophosphorylation is described elsewhere (Hausser et al., 2002). Peroxidase-labeled secondary anti-mouse and anti-rabbit IgG antibodies are from Amersham; alkaline phosphatase-labeled secondary anti-mouse IgG antibody is from Sigma; Alexa Fluor 488- and 546-labeled secondary anti-mouse and anti-rat IgG antibodies are from Molecular Probes.

DNA Constructs

Full-length CERT cDNA is amplified by PCR using pcDNA3-Flag-CERT as a template with primers containing EcoRI restriction sites and cloned into the pEGFPC1 vector. The point mutants of CERT are generated by Quikchange site-directed PCR mutagenesis following the manufacturer's instructions (Stratagene). Truncated CERT variants are generated by insertion of STOP codons. The following oligonucleotides are used: CERT-S132A (SEQ ID NO. 1: 5'-cgtcgacatggcgcaatggtgtccctgg-3'), CERT-S132A rev (SEQ ID NO:2: 5'-ccagggacaccattgcgccatgtcgacg-3'), CERT-S272A (SEQ ID NO. 3: 5'-ggttaaacgtgaggacgcctggcagaagagactgg-3'); CERT-S272Arev (SEQ ID NO. 4: 5'-ccagtctcttctgccaggcgtcctcacgtttaacc-3'), CERT truncations at amino acid 138 (SEQ ID NO:5: 5'-ggtgtccctggtgtcttgagcaagtggctactc-3'); CERT-138 truncation rev (SEQ ID NO. 6: 5'-gagtagccacttgctcaagacaccagggacacc-3'). The Flag-CERT cDNA is subcloned into pGEX6P1 using EcoRI restriction sites. pEGFP-N-1-PKD and pEGFP-N1-$PKD_{K612W}$ are described previously (Hausser et al., 2005). The plasmid encoding ss-HRP-Flag is kindly provided by Vivek Malhotra (UCSD).

Cell Culture and Transfection

HEK293T and COS7 cells grow in RPMI supplemented with 10% fetal calf serum (FCS) in a humified atmosphere containing 5% $CO_2$. HEK293T cells are transfected using TransIT293 reagent (Mirus) according to the manufacturer's instructions. For immunofluorescence, COS7 cells are grown on glass coverslips for 24 hours and transfected with Lipofectamine 2000 reagent (Invitrogen).

CHO cells as well as CHO-derived cell lines producing human serum albumine (HSA) or a human monoclonal IgG antibody are cultivated in suspension in serum-free media in surface-aerated T-flasks (Nunc, Denmark) in incubators (Thermo, Germany) or shake flasks (Nunc, Denmark) at a temperature of 37° C. and in an atmosphere containing 5% $CO_2$.

Seedstock cultures are subcultivated every 2-3 days with seeding densities of 2-3E5 cells/mL. The cell concentration is determined in all cultures by using a hemocytometer. Viability is assessed by the trypan blue exclusion method. All CHO production cells are cultured in BI-proprietary media and their composition may not be revealed.

CHO-derived cells are transfected using Lipofectamine™ and PLUS™ Reagents (both Invitrogen, Germany) according to the guidelines provided by the manufacturer.

Fed-Batch Cultivation

Cells are seeded at 3E05 cells/ml into 125 ml shake flasks in 30 ml of BI-proprietary production medium without antibiotics or MTX (Sigma-Aldrich, Germany). The cultures are agitated at 120 rpm in 37° C. and 5% $CO_2$ which is later reduced to 2% as cell numbers increase. Culture parameters including pH, glucose and lactate concentrations are determined daily and pH is adjusted to pH 7.0 using $NaCO_3$ as needed. BI-proprietary feed solution is added every 24 hrs. Cell densities and viability are determined by trypan-blue exclusion using an automated CEDEX cell quantification system (Innovatis). Samples from the cell culture fluid are collected at day 3, 5 and 7 and subjected to titer measurement by ELISA.

ELISA

Quantification of IgG molecules in the supernatant of the cell clones is performed via sandwich ELISA technology. ELISA plates are coated using a goat anti-human IgG Fc-Fragment antibody (Dianova, Germany) at 4° C. over night. After washing and blocking of the plates with 1% BSA solution, the samples are added and incubated for 1.5 hours. After washing, the detection antibody (alkaline-phosphatase conjugated goat anti-human kappa light chain antibody) is added and colorimetric detection is performed by incubation with 4-nitrophenyl phosphate disodium salt hexahydrate (Sigma, Germany) as substrate. After 20 min incubation in the dark, the reaction is stopped and the absorbance is immediately measured using an absorbance reader (Tecan, Germany) with 405/492 nm. The concentration is calculated according to the standard curve which is present on each plate. Quantitative determination of secreted HSA in culture samples is performed similarly, using the antibodies containied in the Human Albumin ELISA Quantitation Kit (Bethyl Labs, Texas, USA) and following the manufacturers instructions.

Immunofluorescence Microscopy

Cells are washed with PBS containing magnesium and calcium, fixed in 4% paraformaldehyde at room temperature for 10 min, washed and incubated with PBS containing 0.1 M glycine for 15 min. Cells are then permeabilized with PBS containing 0.1% Triton for 5 min and then blocked with 5% goat serum in PBS containing 0.1% Tween-20 for 30 min. Cells are incubated with primary antibody diluted in blocking buffer for 2 hours, followed by incubation with secondary antibodies diluted in blocking buffer for 1 hour. Coverslips are mounted in Fluoromount G (Southern Biotechnology) and cells are analyzed on a confocal laser scanning microscope (TCS SL, Leica) using 488 and 543 nm excitation and a 40.0/1.25 HCX PL APO objective lens. Images are processed with Adobe Photoshop.

Protein Extraction, Immunoprecipitation and Western Blotting

Whole cell extracts are obtained by solubilizing cells in NP40 extraction buffer (NEB) [50 mM Tris (pH 7.5), 150 mM NaCl, 1% NP40, 1 mM sodium orthovanadate, 10 mM sodium fluoride, and 20 mM β-glycerophosphate plus Complete protease inhibitors]. Lysates are clarified by centrifugation at 16,000×g for 10 min. For immunoprecipitations, equal amounts of protein are incubated with specific antibodies for 2 h on ice. Immune complexes are collected with protein G-Sepharose (GE Healthcare) and washed three times with NEB (see above). Whole cell extracts or immunoprecipitated proteins are boiled in sample buffer and subjected to SDS- PAGE. The proteins are blotted onto polyvinylidine difluoride membranes (Roth). After blocking with 0.5% blocking reagent (Roche) in PBS containing 0.1% Tween 20, filters are probed with specific antibodies. Proteins are visualized with peroxidase-coupled secondary antibody using the enhanced chemiluminescence detection system (Pierce). Stripping of membranes is performed in SDS buffer [62.5 mM Tris (pH 6.8), 2% SDS, and 100 mM β-mercaptoethanol] for 30 min at 60° C. Membranes are then reprobed with the indicated antibodies.

Recombinant Protein Purification and In Vitro Kinase Assays

BL21 bacteria are transformed with pGEX6P-Flag-CERT (1-138) and CERT-S132A(1-138) vectors. Expression is induced with 0.5 mM isopropyl-β-D-1-thiogalactopyranoside for 4 hrs at 30° C. Bacteria are harvested and resuspended in PBS containing 50 μg/ml lysozyme, Complete protease inhibitors (Roche), 10 mM sodium fluoride and 20 mM □-glycerophosphate. Triton X-100 is added to a final concentration of 1% prior to sonication. GST-CERT fusions are purified from clarified lysate with glutathione resin (GE Healthcare). The purity of protein preparations is verified by SDS-PAGE and Coomassie staining. Recombinant proteins are incubated with purified PKD1 in kinase buffer [50 mM Tris, pH 7.5, 10 mM $MgCl_2$ and 1 mM DTT] in the presence of either 2 μCi [γ-$^{32}$P]-ATP or 75 μM cold ATP for 30 min. Samples are resolved by SDS-PAGE, blotted onto membrane and analyzed on a PhosphoImager (Molecular Dynamics) or by Western blotting with anti-PKD substrate antibody.

PIP Arrays

HEK293T cells transiently expressing GFP-tagged CERT variants are harvested in hypotonic buffer [50 mM Tris, pH 7.4, containing Complete protease inhibitors (Roche), 1 mM PMSF, 5 mM β-glycerophosphate and 5 mM sodium fluoride] and sheared by passage through a 25 G/16 mm gauge needle. The cytosol fraction is obtained after 100.000×g centrifugation for 1 h and the amount of expressed protein is quantified by measuring GFP peak emission at 480-550 nm (excitation 466 nm). PIP arrays (Echelon) are blocked in TBS-T [10 mM Tris, pH 8, 150 mM NaCl, 0.1% Tween-20] containing 3% fatty acid-free BSA (Roth), followed by incubation with 500 μg cytosol containing equal amounts of GFP proteins (adjusted with cytosol from untransfected cells) in 5 ml blocking buffer for 1 h at room temperature. Bound proteins are detected by incubation with anti-GFP antibody, followed by HRP-conjugated secondary antibody.

In Vitro Ceramide Transfer Assay

Protein-mediated transfer of ceramide between SUVs is measured as described previously (Olayioye et al., 2005). The transfer assay mixture contained donor vesicles (2 nmol lipid/ml) composed of porcine brain lipids (Avanti Polar Lipids), pyrene-labeled $C_{16}$-ceramide, and 2,4,6-trinitrophenyl-phosphatidylethanolamine (TNP-PE) (88.6:0.4:11 mol %), provided by P. Somerharju, and a 10-fold excess of acceptor vesicles composed of porcine brain lipids. Fluorescence intensity is recorded at 395 nm (excitation, 345 nm; slit widths, 4 nm) before and after the addition of 75 μg cytosol from HEK293T cells transiently expressing the GFP-tagged CERT wild type and S132A proteins (see above). Fluorescence intensities are normalized to (i) the maximum intensity obtained after the addition of Triton X-100 (0.5% final concentration) and (ii) the maximum GFP fluorescence, to account for different protein expression levels.

HRP Transport Assay

HEK293T cells are cotransfected with ss-HRP-Flag plasmid and empty vector, pEGFP-N1-PKD1KD, pcDNA3-Flag-CERT wt and pcDNA3-Flag-CERT-S132A at a ratio of 1:6.5, respectively. 24 h post-transfection cells are washed with serum-free media and HRP secretion is quantified after 0, 1, 3 and 6 h by incubation of clarified cell supernatant with ECL reagent. Measurements are done with a luminometer (Lucy2, Anthos) at 450 nm.

siRNA Assay

COS7 cells are transfected with a vector encoding ssHRP-Flag, harvested after 8 hrs, replated into triplicate wells and then transfected with CERT-specific siRNA oligonucleotides (siCERT#1, SEQ ID NO. 7: 5'-ccacaugacuuacucauuatt-3'; siCERT#2, SEQ ID NO. 8: 5'-gaacagaggaagcauauaatt-3') using Oligofectamine™ reagent (Invitrogen) according to the manufacturers instructions. Control cells are either mock transfected or transfected with a lacZ-specific siRNA (SEQ ID NO. 9: 5'-gcggcugccggaauuuacctt-3'). 48 h later, cells are washed and fresh medium is added. The amount of HRP secreted into the supernatant is measured by a chemiluminescent assay as described above. Finally, cells are lysed, triplicate lysates are pooled and analyzed by immunoblotting using tubulin- und transferrin receptor-specific antibodies.

EXAMPLES

Example 1

Intracellular Product Accumulation Indicates Secretory Bottle Neck

A fed-batch process is performed using three different CHO producer cell clones expressing human IgG antibody (Process A, B and M, respectively, see FIG. 1). Cell samples are taken every other day and the amount of intracellular antibody is determined by FACS analysis. In short, cells are fixed using PBS/4% PFA, permeabilized and stained with FITC-conjugated anti-human kappa light chain antibody. Within the first four days, the intracellular IgG content remains at a constant level. However from day 5 to day 9, the level of intracellular product rises constantly, indicating an accumulation of either misfolded light chain or even the complete antibody product within the cell. These data represent the results of three independent production processes with different producer cell clones and products and they strongly suggest that the cell transcribes more antibody RNA than proteins secreted into the medium and thus points to a post-translational bottle neck which hinders the complete secretion of the produced antibody (FIG. 1).

Example 2

CERT is Detected by a PKD Substrate Antibody

PKD is a key regulator at the Golgi complex with PI4KIIIβ being the only local substrate identified thus far. To test whether the Golgi complex-localized CERT protein (SEQ ID NO. 11 and 13) may serve as a substrate for PKD, we make use of a phosphospecific substrate antibody, termed pMOTIF, raised against consensus motifs phosphorylated by PKD (Doppler et al., 2005). HEK293T cells are transfected with expression vectors encoding Flag-tagged CERT (SEQ ID NO. 10) and $CERT_L$(SEQ ID No. 12). The CERT isoforms are immunoprecipitated with Flag-specific antibodies and analyzed by Western blotting with the pMOTIF antibody (FIG. 4A). A pMOTIF signal corresponding to the molecular weight of CERT (SEQ ID NO. 11) and, more weakly, to that of $CERT_L$. (SEQ ID No. 13) is detected. The weaker detection of the phosphorylated $CERT_L$ isoform may be related to its known behaviour to form aggregates, which may impact phosphosite accessibility to kinases (Raya et al., 2000).

To investigate whether recognition of CERT by the pMOTIF antibody is dependent upon PKD, we express CERT together with a kinase dead variant of PKD1 (K621W) in HEK293T cells. This mutant has been shown to localize to the Golgi complex and suppressed PI4KIIIβ phosphorylation in a dominant negative fashion (Hausser et al., 2005). Coexpression of inactive PKD abolishes detection of CERT with the pMOTIF antibody, suggesting that the pMOTIF signal is indeed due to PKD-mediated CERT phosphorylation (FIG. 4B).

Lipid transfer proteins are thought to act at membrane contact sited, which are formed between the ER and TGN (Levine and Loewen, 2006), where PKD is localized. Immunofluorescence staining of Flag-tagged CERT in COS7 cells coexpressed with GFP-tagged PKD1 verify that the two proteins colocalize at the Golgi complex (FIG. 4C). Together, these data confirm that CERT is a PKD substrate at the Golgi apparatus.

Example 3

PKD Phosphorylates CERT on Serine 132

To identify pMOTIF recognition sites in CERT, we search for potential PKD consensus motifs characterized by a leucine, isoleucine or valine residue in the −5 and arginine in the −3 position relative to a serine or threonine. Two serines at positions 132 and 272, matching the PKD consensus motif and conserved across species (FIG. 5A), are exchanged for alanines by site-directed mutagenesis. These mutants are expressed in HEK293T cells and tested for recognition by the pMOTIF antibody. Interestingly, mutation of serine 132 to alanine abrogate detection of CERT with the pMOTIF antibody and cause an increase in electrophoretic mobility, indicative of loss of phosphorylation, while the S272A mutation does not affect the pMOTIF signal (FIG. 5B). This suggests that serine 132 is a PKD phosphorylation site specifically recognized by the PKD substrate antibody. To confirm that PKD is capable of directly phosphorylating this serine residue in CERT, we perform in vitro kinase assays with purified PKD1 and recombinant CERT GST-fusion proteins produced in *E. coli* comprising the first 138 amino acids of the protein. When the truncated wild type CERT fusion protein is incubated with PKD1 in the presence of [$\gamma$-$^{32}$P]-ATP, incorporation of radioactivity is detected (FIG. 5C). This is significantly impaired in the case of the CERT-S132A fusion protein. In vitro PKD phosphorylation of wild type but not CERT-S132A (SEQ ID NO. 15) is further shown to generate a recognition site for the pMOTIF antibody (FIG. 5D). Taken together, these results prove that CERT is a genuine PKD substrate in vitro and in vivo and identify serine 132 as a specific PKD phosphorylation site in CERT.

Example 4

CERT Phosphorylation on Serine 132 Modulates PI(4)P Binding and Ceramide Transfer Activity Serine 132 is in very close proximity to the CERT PH domain (amino acids 23-117), making it possible that phosphorylation on this site affects PI(4)P binding by increasing the local negative charge. We therefore quantify PI(4)P binding of wild type CERT and the CERT-S132A mutant (SEQ ID NO. 15) by performing protein-lipid overlay assays. Here, cytosol from HEK293T cells transiently expressing the CERT variants is incubated with membranes spotted with a concentration gradient of the different phosphoinositides and bound CERT proteins are detected via their GFP tag. As reported previously, the full-length wild type protein demonstrate weak binding to several phospholipid species, but displays strong interaction with PI(4)P (Hanada et al., 2003; Levine and Munro, 2002). CERT-S132A binding to PI(4)P is detectable at two- to fourfold lower concentrations as compared to that of the wild type protein, suggesting increased affinity of the CERT-S132A mutant to this phospholipid (FIG. 6A).

Together, these data imply that CERT, once bound to the Golgi complex, is phosphorylated by PKD. This then decreases the affinity of CERT to PI(4)P and thereby regulates the interaction of CERT with Golgi membranes.

As CERT has been shown to function as a lipid transfer protein (Hanada et al., 2003). We investigate whether CERT phosphorylation on serine 132 influenced its ability to bind and transfer ceramide between membranes. To this end, GFP-tagged versions of wild type CERT (SEQ ID NO. 10) and CERT-S132A (SEQ ID NO. 14) are transiently expressed in HEK239T cells and the cytosol fraction is analyzed for ceramide-specific lipid transfer activity using a FRET-based assay (FIG. 6B). In this assay, small unilamellar vesicles containing pyrene-labeled ceramide as a fluorescent donor and quenching amounts of head group-labeled TNP-PE are employed (Olayioye et al., 2005; Somerharju, 2002). When these donor liposomes are mixed with an excess of unlabeled acceptor liposomes, the increase in pyrene fluorescence is negligible, indicating minimal spontaneous ceramide transfer to acceptor membranes (data not shown).

Upon addition of wild type CERT-containing cytosol, a steady increase in fluorescence is noted, which is not observed when control cytosol of vector-transfected cells is used (FIG. 6B). Compared to the wild type protein, CERT-S132A (SEQ ID No. 15) displays a higher rate of lipid transfer, evident from a more rapid increase in pyrene fluorescence.

This suggests that CERT phosphorylation on serine 132 downregulates ceramide transfer activity by decreasing association of the protein with membranes.

Previous data have already shown that PKD regulates the level of PI(4)P at the Golgi complex by phosphorylation-mediated activation of PI4KIIIβ (Hausser et al., 2005). Interestingly, PI4KIIIβ is critical for the transport of ceramide between the ER and the Golgi complex (Toth et al., 2006). Accordingly, together with the data presented here, a dual role for PKD in maintaining lipid homeostasis of Golgi membranes becomes apparent by controlling the on-rate (via PI(4)P levels) and the off-rate (via direct phosphorylation) of CERT.

Example 5

CERT Regulates PKD Activation and Secretory Transport

We hypothesize that overexpression of CERT by transferring ceramide should result in elevated DAG levels and might consequently stimulate PKD activity. To test this, Flag-tagged CERT wild type (SEQ ID NO. 10) and CERT-S132A (SEQ ID NO. 14) are transiently expressed in HEK293T cells. Whole cells lysates are prepared 24 h post transfection and subjected to SDSPAGE. PKD activation is analyzed by immunoblotting with phosphospecific pS916 PKD antibody (FIG. 7A, top panel). Equal loading is verified by reprobing with PKD-specific antibody (FIG. 7A middle panel). Expression of CERT proteins is verified by immunoblotting with Flag-specific antibody (FIG. 7A bottom panel). Compared to the control, expression of both CERT wild type and CERT-S132A increased PKD activity, as revealed by analyses with a phosphospecific PKD antibody. This shows that PKD activation is regulated by CERT proteins, likely due to increased ceramide delivery and enforced SM/DAG synthesis.

To address the question of whether CERT-mediated PKD activation indeed translates into enhanced secretory transport, we make use of a plasmid encoding secreted horseradish peroxidase (HRP-ss) which can be used as reporter for constitutive protein secretion. HEK293T cells are cotransfected with an expression plasmid encoding Flag-ss-HRP or empty vector, and PKD1-GFP kinase dead (KD), Flag-CERT wild type (WT), and Flag-CERT-S132A, respectively. 24 h post-transfection, cells are washed and fresh medium is added. The supernatant is analyzed for peroxidase activity after 0, 1, 3, and 6 h by chemiluminescence. In control cells, secretion of ss-HRP could be detected within 1 hour and increased over time (FIG. 7B). Coexpression of kinase dead PKD1, which inhibits secretory transport of cargo protein almost entirely abrogates the secretion of ss-HRP into the supernatant. This confirms that HRP is secreted in a PKD-dependent manner in this assay. In Contrast, coexpression of CERT wild type and CERT-S132A strongly augmented the amount of secreted HRP (FIG. 7B), the mutant showing even slightly higher values than wild type CERT. This experiment demonstrates that CERT overexpression stimulates PKD phosphorylation and in a functional assay enhances secretion of an extracellular protein into the culture medium by around 2-fold.

We furthermore investigates whether overexpression of the CERT-S132A mutant affected its localization and/or caused morphological changes of the Golgi apparatus. CERT has been demonstrated to colocalize with the cis/medial-Golgi marker GS28 (Hanada et al., 2003).

Immunofluorescence analysis of GFP-tagged CERT expressed in COS7 cells shows that the protein localized to GS28-positive Golgi regions (FIG. 7C). By contrast, in addition to the partial colocalization with GS28 at the Golgi complex, the CERT-S132A mutant protein displays a dispersed, punctate staining. Of note, some of these vesicular structures are found to contain the cargo protein ss-HRP, providing evidence that these structures indeed represent Golgi-derived transport carriers (FIG. 7D). This finding is in accordance with the observed changes in Golgi membrane structure due to local increases in ceramide levels (Fukunaga et al., 2000; Weigert et al., 1999).

Example 6

CERT Downregulation by RNA Interference Inhibits Secretory Transport

The data presented so far in the present invention clearly demonstrated that overexpression of CERT enhances protein secretion. To investigate whether also the opposite is true, meaning that reduced CERT expression would result in diminished secretion, siRNA experiments are performed. COS7 cells are transfected with a vector encoding ssHRP-Flag, harvested after 8 hrs, replated into triplicate wells and then transfected with CERT-specific siRNA oligonucleotides (SEQ ID NO. 7 and 8) or either mock or lacZ-specific siRNA (SEQ ID NO. 9) as controls. 48 h later, cells are washed, covered with fresh medium and the amount of HRP secreted into the supernatant is measured after the indicated times.

As shown in FIG. 8A, activity of HRP is detected after 3 hours and showed equal comparable levels in both control cells. In contrast, a dramatic reduction of HRP activity is measured in cells that had been treated with any of the CERT-specific siRNA oligonucleotides. This indicates that reduced CERT levels lead to reduced HRP secretion from the cells and further underscores the important role of CERT in the secretory transport.

Interestingly, not only protein secretion, but also the abundance of the transmembrane protein transferrin receptor is affected by the reduction of CERT (FIG. 8B). When the cells from FIG. 8A are pooled and the lysates probed with transferrin receptor-specific antibodies in Western blot experiments, a strong decrease in the amount of transferrin receptor became apparent, whereas similar transferrin receptor levels are detected in both control cells.

This finding suggests, that the lipid transfer protein CERT is not only implicated in the transport of secreted but also of membrane-standing cell-surface proteins. This might not be surprising as both types of proteins are equally transported in lipid vesicles from the ER via the Golgi to the plasma membrane and thus use the same cellular export routes which—as we demonstrate in the present invention for the first time—are influenced by CERT.

Example 7

Overexpression of CERT Increases Biopharmaceutical Protein Production of an Antibody (a) An antibody producing CHO cell line (CHO DG44) secreting humanised anti-CD44v6 IgG antibody BIWA 4 is transfected with an empty vector (MOCK control) or expression constructs encoding wild type CERT (SEQ ID NO. 10 and 12) or a mutant of CERT bearing the point-mutation Ser132A (SEQ ID NO. 14) and subsequently subjected to selection to obtain stable cell pools. During six subsequent passages, supernatant is taken from seed-stock cultures of all stable cell pools, the IgG titer is determined by ELISA and divided by the mean number of cells to calculate the specific productivity (FIG. 10A). The highest values are seen in the cell pools harbouring the CERT mutant (SEQ ID No. 14), followed by wild type CERT (SEQ ID No. 10 or 12). In both, IgG expression is markedly enhanced compared to MOCK or untransfected cells. Very similar results can be obtained if the stable transfectants are subjected to batch or fed-batch fermentations (FIG. 10B). In each of these settings, overexpression of both wild type and mutant CERT leads to increased antibody secretion, indicating that CERT is able to enhance the specific production capacity of the cells grown in serial cultures or in bioreactor batch or fed batch cultures.

b) CHO host cells (CHO DG44) are first transfected with vectors encoding wild type CERT (SEQ ID NO. 10 or 12) or a mutant of CERT bearing the point-mutation Ser132A (SEQ ID NO. 14). Cells are subjected to selection pressure and cell lines are picked that demonstrate heterologous expression of CERT or the CERT mutant. Subsequently these cell lines and in parallel CHO DG 44 wild type cells are transfected with vectors encoding humanized anti-CD44v6 IgG antibody BIWA 4 as the gene of interest. After a second round of selection, supernatant is taken from seed-stock cultures of all stable cell pools over a period of six subsequent passages, the IgG titer is determined by ELISA and divided by the mean number of cells to calculate the specific productivity. The highest values are seen in the cell pools harbouring the CERT mutant (SEQ ID No. 14), followed by wild type CERT (SEQ ID NO. 10 or 12). In both, IgG expression is markedly enhanced compared to cells that don't have heterologous expression of CERT or CERT mutant. Very similar results can be obtained if the stable transfectants are subjected to batch or fed-batch fermentations. In each of these settings, overexpression of both wild type and mutant CERT leads to increased antibody secretion, indicating that CERT is able to enhance the specific production capacity of the cells grown in serial cultures or in bioreactor batch or fed batch cultures.

This indicates, that heterologous expression of CERT, and especially mutant CERT, can enhance antibody secretion in transiently as well as stably transfected CHO cell lines.

Example 8

Overexpression of CERT Increases Biopharmaceutical Protein Production of Monocyte Chemoattractant Protein 1 (MCP-1)

(a) A CHO cell line (CHO DG44) secreting monocyte chemoattractant protein 1 (MCP-1) is transfected with an empty vector (MOCK control) or expression constructs encoding wild type CERT (SEQ ID NO. 10 and 12) or a mutant of CERT bearing the point-mutation Ser132A (SEQ ID NO. 14) and subsequently subjected to selection to obtain stable cell pools. During six subsequent passages, supernatant is taken from seed-stock cultures of all stable cell pools, the MCP-1 titer is determined by ELISA and divided by the mean number of cells to calculate the specific productivity. The highest values are seen in the cell pools harbouring the CERT mutant, followed by wild type CERT. In both, IgG expression is markedly enhanced compared to MOCK or untransfected cells. Very similar results can be obtained if the stable transfectants are subjected to batch or fed-batch fermentations. In each of these settings, overexpression of both wild type and mutant CERT leads to increased MCP-1 secretion, indicating that CERT is able to enhance the specific production capacity of the cells grown in serial cultures or in bioreactor batch or fed batch cultures.

b) CHO host cells (CHO DG44) are first transfected with vectors encoding wild type CERT (SEQ ID NO. 10 or 12) or a mutant of CERT bearing the point-mutation Ser132A (SEQ ID NO. 14). Cells are subjected to selection pressure and cell lines are picked that demonstrate heterologous expression of CERT or the CERT mutant. Subsequently these cell lines and in parallel CHO DG 44 wild type cells are transfected with a vector encoding monocyte chemoattractant protein 1 (MCP-1) as the gene of interest. After a second round of selection, supernatant is taken from seed-stock cultures of all stable cell pools over a period of six subsequent passages, the MCP-1 titer is determined by ELISA and divided by the mean number of cells to calculate the specific productivity. The highest values are seen in the cell pools harbouring the CERT mutant, followed by wild type CERT. In both, MCP-1 expression is markedly enhanced compared to cells that don't have heterologous expression fo CERT or CERT mutant. Very similar results can be obtained if the stable transfectants are subjected to batch or fed-batch fermentations. In each of these settings, overexpression of both wild type and mutant CERT leads to increased antibody secretion, indicating that CERT is able to enhance the specific production capacity of the cells grown in serial cultures or in bioreactor batch or fed batch cultures.

This indicates, that heterologous expression of CERT, and especially mutant CERT, can enhance the secretion of single cell proteins in transiently as well as stably transfected CHO cell lines.

Example 9

Overexpression of CERT Increases Biopharmaceutical Protein Production of Transmembrane Protein Epithelial Growth Factor Receptor (EGFR)

(a) A CHO cell line (CHO DG44 expressing transmembrane protein epithelial growth factor receptor (EGFR) is transfected with an empty vector (MOCK control) or expression constructs encoding wild type CERT (SEQ ID NO. 10 and 12) or a mutant of CERT bearing the point-mutation Ser132A (SEQ ID NO. 14) and subsequently subjected to selection to obtain stable cell pools. During six subsequent passages, cells are taken from seed-stock cultures of all stable cell pools and the expression level of EGFR is determined by FACS or Western blotting. The highest values are seen in the cell pools harbouring the CERT mutant, followed by wild type CERT. In both, EGFR expression is markedly enhanced compared to MOCK or untransfected cells. Very similar results can be obtained if the stable transfectants are subjected to batch or fed-batch fermentations. In each of these settings, overexpression of both wild type and mutant CERT leads to increased EGFR expression, indicating that CERT is able to enhance the specific production capacity of the cells grown in serial cultures or in bioreactor batch or fed batch cultures.

b) CHO host cells (CHO DG44) are first transfected with vectors encoding wild type CERT (SEQ ID NO. 10 or 12) or a mutant of CERT bearing the point-mutation Ser132A (SEQ ID NO. 14). Cells are subjected to selection pressure and cell lines are picked that demonstrate heterologous expression of CERT or the CERT mutant. Subsequently these cell lines and in parallel CHO DG 44 wild type cells are transfected with a vector encoding EGFR as the gene of interest. After a second round of selection, cells are taken from seed-stock cultures of all stable cell pools for six consecutive passages and the expression level of EGFR is determined by FACS or Western blotting. The highest values are seen in the cell pools harbouring the CERT mutant, followed by wild type CERT. In both, EGFR expression is markedly enhanced compared to cells that don't have heterologous expression of CERT or CERT mutant. Very similar results can be obtained if the stable transfectants are subjected to batch or fed-batch fermentations. In each of these settings, overexpression of both wild type and mutant CERT leads to increased EGFR expression, indicating that CERT is able to enhance the specific production capacity of the cells grown in serial cultures or in bioreactor batch or fed batch cultures.

This indicates, that heterologous expression of CERT, and especially mutant CERT, can enhance expression of surface receptors in transiently as well as stably transfected CHO cell lines.

Example 10

Overexpression of STARD4 Increases Biopharmaceutical Protein Production of an Antibody (a) An antibody producing CHO cell line (CHO DG44) secreting humanised anti-CD44v6 IgG antibody BIWA 4 is transfected with an empty vector (MOCK control) or expression constructs encoding StarD4 (SEQ ID NO. 20) and subsequently subjected to selection to obtain stable cell pools. During six subsequent passages, supernatant is taken from seed-stock cultures of all stable cell pools, the IgG titer is determined by ELISA and divided by the mean number of cells to calculate the specific productivity. The highest values are seen in the cell pools harbouring StarD4. IgG expression is markedly enhanced compared to MOCK or untransfected cells. Very similar results can be obtained if the stable transfectants are subjected to batch or fed-batch fermentations. In each of these settings, overexpression of StarD4 is able to enhance the specific production capacity of the cells grown in serial cultures or in bioreactor batch or fed batch cultures.

b) CHO host cells (CHO DG44) are first transfected with vectors encoding StarD4. Cells are subjected to selection pressure and cell lines are picked that demonstrate heterologous expression of StarD4. Subsequently these cell lines and in parallel CHO DG 44 wild type cells are transfected with vectors encoding humanized anti-CD44v6 IgG antibody BIWA 4 as the gene of interest. After a second round of selection, supernatant is taken from seed-stock cultures of all stable cell pools over a period of six subsequent passages, the IgG titer is determined by ELISA and divided by the mean number of cells to calculate the specific productivity. The highest values are seen in the cell pools harbouring StarD4. IgG expression is markedly enhanced compared to cells that don't have heterologous expression of StarD4. Very similar results can be obtained if the stable transfectants are subjected to batch or fed-batch fermentations. In each of these settings, overexpression of StarD4 is able to enhance the specific production capacity of the cells grown in serial cultures or in bioreactor batch or fed batch cultures.

This indicates, that heterologous expression of StarD4, can enhance antibody secretion in transiently as well as stably transfected CHO cell lines.

Example 11

Overexpression of CERT Increases Biopharmaceutical Protein Production of Human Serum Albumin (HSA)

(a) A CHO cell line (CHO DG44) secreting the single chain protein HSA is transfected with an empty vector (Mock control) or expression constructs encoding wild type CERT (SEQ ID NO. 10 and 12) or a mutant of CERT bearing the point-mutation Ser132A (SEQ ID NO. 14) and subsequently subjected to selection to obtain stable cell pools. During 4 subsequent passages, supernatant is taken from seed-stock cultures of all stable cell pools, the HSA titer is determined by ELISA and divided by the mean number of cells to calculate the specific productivity (FIG. 11A).

Both, HSA titers and the specific productivity of the HSA producing cells is significantly enhanced by heterologous expression of both CERT variants compared to the Mock transfected control. The highest values are seen in the cell pools harbouring the CERT mutant, which leads to an increase in the specific productivity of 51% and an increase in HSA titer of 46% above the control, followed by wild type CERT, which increases the specific productivity by 49%.

Very similar results can be obtained if the stable transfectants are subjected to batch or fed-batch fermentations (FIG. 11B). In each of these settings, overexpression of both wild type and mutant CERT leads to increased HSA secretion, indicating that CERT is able to enhance the specific production capacity of the cells grown in serial cultures or under industrial production conditions such as in bioreactor batch or fed batch cultures.

(b) and (c) CHO host cells (CHO DG44) are first transfected with vectors encoding wild type CERT (SEQ ID NO. 10 or 12) or a mutant of CERT bearing the point-mutation Ser132A (SEQ ID NO. 14). Cells are subjected to selection pressure and cell lines are picked that demonstrate heterologous expression of CERT or the CERT mutant.

Figure 11:
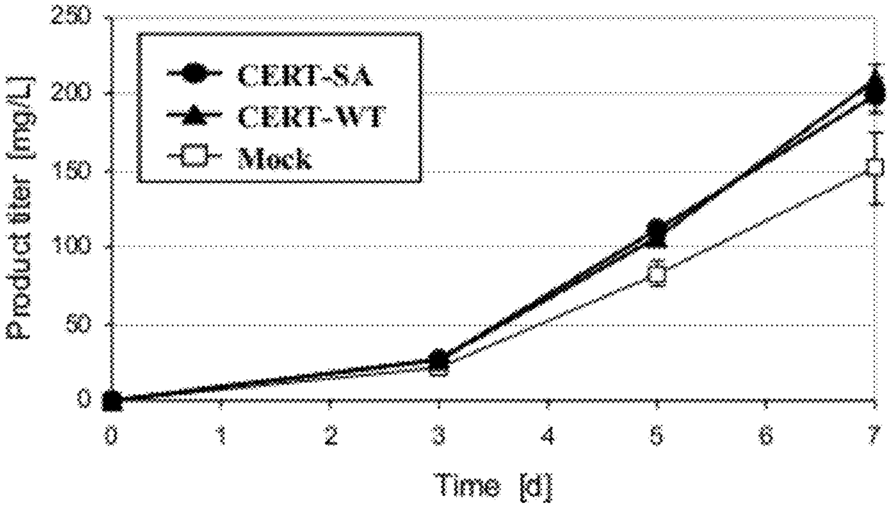

Subsequently these cell lines and in parallel CHO DG 44 wild type cells are transfected with a vector encoding human serum albumin as the gene of interest. After a second round of selection, supernatant is taken from seed-stock cultures of all stable cell pools over a period of six subsequent passages, the HSA titer is determined by ELISA (FIG. 11 C) and divided by the mean number of cells to calculate the specific productivity (FIG. 11B).

The highest values are seen in the cell pools harbouring the CERT mutant, followed by wild type CERT. In both, HSA expression is markedly enhanced compared to cells that don't have heterologous expression of CERT or CERT mutant. Very similar results can be obtained if the stable transfectants are subjected to batch or fed-batch fermentations. In each of these settings, overexpression of both wild type and mutant CERT leads to increased antibody secretion, indicating that CERT is able to enhance the specific production capacity of the cells grown in serial cultures or in bioreactor batch or fed batch cultures.

This indicates, that heterologous expression of CERT, and especially mutant CERT, can enhance the secretion of single-chain proteins in transiently as well as stably transfected CHO cell lines.

The invention claimed is:

1. A method of producing a secreted heterologous protein of interest in a cell comprising:

a. increasing the expression or activity of a ceramide transfer protein (CERT) having an amino acid sequence comprising a steroidogenic acute regulatory related lipid transfer (START) domain;

b. effecting the expression and secretion of said protein of interest, wherein said protein of interest is secreted into a culture medium; and c. isolating and purifying said protein of interest, wherein said isolating comprises recovering said protein of interest from the culture medium.

2. The method of claim 1, whereby the START domain comprises at least the 219 amino acids of SEQ ID NO. 19 (START domain of $CERT_L$, or at least the 223 amino acids of SEQ ID NO. 17 (START domain of CERT and CERT S132A).

3. The method of claim 1, whereby the ceramide transfer protein (CERT) comprises the amino acid sequence of SEQ ID NO. 11 or SEQ ID NO. 13.

4. The method of claim 3, whereby the ceramide transfer protein (CERT) is a mutated ceramide transfer protein (CERT) and said mutation disables and/or deletes the protein kinase D (PKD) phosphorylation site of CERT at position 132.

5. The method of claim 1, whereby the mutated CERT is CERT S132A comprising the amino acid sequence of SEQ ID NO. 15.

6. The method of claim 1, whereby said method results in increased specific cellular productivity of said protein of interest in said cell in comparison to a control cell expressing said protein of interest, but whereby said control cell does not have increased expression or activity of a ceramide transfer protein (CERT) having an amino acid sequence comprising a steroidogenic acute regulatory related lipid transfer (START) domain.

7. The method according to claim 6, whereby the increase in productivity is about 5% to about 10%, about 11% to about 20%, about 21% to about 30%, about 31% to about 40%, about 41% to about 50%, about 51% to about 60%, about 61% to about 70%, about 71% to about 80%, about 81% to about 90%, about 91% to about 100%, about 101% to about 149%, about 150% to about 199%, about 200% to about 299%, about 300% to about 499%, or about 500% to about 1000%.

8. The method of claim 1, whereby said cell is a eukaryotic cell is selected from a yeast, plant, worm, insect, avian, fish, reptile and mammalian cell.

9. The method of claim 8, whereby said eukaryotic cell is a mammalian cell.

10. The method of claim 9, whereby said mammalian cell is a Chinese Hamster Ovary (CHO), monkey kidney CV1, monkey kidney COS, human lens epithelium PER.C6TM, human embryonic kidney, HEK293, baby hamster kidney, African green monkey kidney, human cervical carcinoma, canine kidney, buffalo rat liver, human lung, human liver, mouse mammary tumor or myeloma cell, a dog, pig or macaque cell, rat, rabbit, cat, or goat.

11. The method of claim 10, whereby said CHO cell is CHO wild type, CHO K1, CHO DG44, CHO DUKX-B11, or CHO Pro-5.

12. The method of claim 1, whereby the protein of interest is an antibody or antibody fragment.

13. The method of claim 12, whereby the antibody is monoclonal, polyclonal, mammalian, murine, chimeric, humanized, primatized, primate, human or an antibody fragment or derivative thereof such as antibody, immunoglobulin light chain, immunoglobulin heavy chain, immunoglobulin light and heavy chains, Fab, F(ab')2, Fc, Fc-Fc fusion proteins, Fv, single chain Fv, single domain Fv, tetravalent single chain Fv, disulfide-linked Fv, domain deleted, minibody, diabody, a fusion polypeptide of one of the above fragments with another peptide or polypeptide, Fc-peptide fusion, Fc-toxine fusion, or scaffold proteins.

14. A method of increasing specific cellular productivity of a secreted protein of interest in a cell comprising the steps of:

i) introducing into a cell one or more vector systems comprising nucleic acid sequences encoding for at least two polypeptides whereby:

a. a first polynucleotide encodes a ceramide transfer protein (CERT) having an amino acid sequence comprising a steroidogenic acute regulatory related lipid transfer (START) domain; and b. a second polynucleotide encodes a secreted protein of interest;

ii) culturing the cell in a culture medium, whereby the protein of interest and the ceramide transfer protein (CERT) having an amino acid sequence comprising a steroidogenic acute regulatory related lipid transfer (START) domain are expressed by said cell and whereby the protein of interest is secreted into the culture medium; and iii) isolating and purifying said protein of interest, wherein said isolating comprises recovering the protein of interest from the culture medium.

15. A method of increasing secretion and/or production of a secreted protein of interest, comprising the step of:

a. transfecting said cell with a first polynucleotide encoding a ceramide transfer protein (CERT) having an amino acid sequence comprising a steroidogenic acute regulatory related lipid transfer (START) domain;

b. subsequently transfecting said cell with a second polynucleotide encoding a secreted protein of interest;

whereby said first and second polynucleotides are located on different vector systems;

c. culturing the cell in a culture medium to effect the expression and secretion of said protein of interest into the culture medium; and d. isolating and purifying said protein of interest, wherein said isolating comprises recovering said protein of interest from the culture medium.

16. A method of producing a secreted heterologous protein of interest in a cell comprising:

a. obtaining a cell comprising a first polynucleotide encoding a ceramide transfer protein (CERT) having an amino acid sequence comprising a steroidogenic acute regulatory related lipid transfer (START) domain;

b. transfecting said cell with a second polynucleotide encoding said secreted protein of interest;

c. culturing the cell in a culture medium to effect the expression of said protein of interest, whereby said protein of interest is secreted into the culture medium; and d. isolating and purifying said protein of interest, wherein said isolating comprises recovering said protein of interest from the culture medium.

17. A method of producing a secreted heterologous protein of interest in a cell comprising:

a. obtaining a cell comprising (i) a first polynucleotide encoding a ceramide transfer protein (CERT) having an amino acid sequence comprising a steroidogenic acute regulatory related lipid transfer (START) domain and (ii) a second polynucleotide encoding said secreted protein of interest;

b. culturing the cell in a culture medium to effect the expression of said protein of interest, whereby said protein of interest is secreted into the culture medium; and c. isolating and purifying said protein of interest, wherein said isolating comprises recovering said protein of interest from the culture medium.

18. The method according to claim 1, whereby the START domain comprises at least the 223 amino acids of SEQ ID NO. 17 (START domain of CERT and CERT S132A).

19. The method according to claim 18, whereby the ceramide transfer protein (CERT) comprises the amino acid sequence of SEQ ID NO. 11.

20. The method according to claim 18, whereby the ceramide transfer protein (CERT) comprises the amino acid sequence of SEQ ID NO. 15.

21. The method according to claim 1, whereby the START domain comprises at least the 219 amino acids of SEQ ID NO. 19 (START domain of $CERT_L$).

22. The method according to claim 21, whereby the ceramide transfer protein (CERT) comprises the amino acid sequence of SEQ ID NO. 13.

23. The method according to claim 16, whereby the START domain comprises at least the 223 amino acids of SEQ ID NO. 17 (START domain of CERT and CERT S132A).

24. The method according to claim 23, whereby the ceramide transfer protein (CERT) comprises the amino acid sequence of SEQ ID NO. 11.

25. The method according to claim 23, whereby the ceramide transfer protein (CERT) comprises the amino acid sequence of SEQ ID NO. 15.

26. The method according to claim 16, whereby the START domain comprises at least the 219 amino acids of SEQ ID NO. 19 (START domain of $CERT_L$).

27. The method according to claim 26, whereby the ceramide transfer protein (CERT) comprises the amino acid sequence of SEQ ID NO. 13.

28. The method according to claim 17, whereby the START domain comprises at least the 223 amino acids of SEQ ID NO. 17 (START domain of CERT and CERT S132A).

29. The method according to claim 28, whereby the ceramide transfer protein (CERT) comprises the amino acid sequence of SEQ ID NO. 11.

30. The method according to claim 28, whereby the ceramide transfer protein (CERT) comprises the amino acid sequence of SEQ ID NO. 15.

31. The method according to claim 17, whereby the START domain comprises at least the 219 amino acids of SEQ ID NO. 19 (START domain of $CERT_L$).

32. The method according to claim 31, whereby the ceramide transfer protein (CERT) comprises the amino acid sequence of SEQ ID NO. 13.

* * * * *